US009771352B2

(12) United States Patent
Schmeck et al.

(10) Patent No.: US 9,771,352 B2
(45) Date of Patent: Sep. 26, 2017

(54) HYDROXYALKYL-SUBSTITUTED PHENYLTRIAZOLE DERIVATIVES AND USES THEREOF

(71) Applicant: BAYER PHARMA AKTIENGESELLSCHAFT, Berlin (DE)

(72) Inventors: Carsten Schmeck, Mülheim (DE); Michael Gerisch, Wuppertal (DE); Nils Griebenow, Dormagen (DE); Peter Kolkhof, Wuppertal (DE); Florian Kölling, Wuppertal (DE); Anna Engelen, Essen (DE); Axel Kretschmer, Wuppertal (DE); Dieter Lang, Velbert (DE); Klemens Lustig, Wuppertal (DE); Thomas Mondritzki, Velbert (DE); Elisabeth Pook, Wuppertal (DE); Hartmut Beck, Wuppertal (DE); Frank Süßmeier, München (DE); Sonja Vollmer, Kleinmachnow (DE); Pierre Wasnaire, Düsseldorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 25 days.

(21) Appl. No.: 14/930,157

(22) Filed: Nov. 2, 2015

(65) Prior Publication Data
US 2016/0122325 A1    May 5, 2016

(30) Foreign Application Priority Data
Nov. 3, 2014  (EP) .................................... 14191491

(51) Int. Cl.
*C07D 403/06*  (2006.01)
*A61K 31/4196*  (2006.01)
*A61K 45/06*  (2006.01)

(52) U.S. Cl.
CPC ........ *C07D 403/06* (2013.01); *A61K 31/4196* (2013.01); *A61K 45/06* (2013.01)

(58) Field of Classification Search
None
See application file for complete search history.

(56) References Cited

U.S. PATENT DOCUMENTS

| 5,276,049 | A  | 1/1994  | Himmelsbach et al. |
| 5,281,614 | A  | 1/1994  | Ashton et al. |
| 5,326,776 | A  | 7/1994  | Winn et al. |
| 5,468,448 | A  | 11/1995 | Nicolson et al. |
| 5,585,394 | A  | 12/1996 | Di Malta et al. |
| 5,681,841 | A  | 10/1997 | Himmelsbach et al. |
| 6,469,012 | B1 | 10/2002 | Ellis et al. |
| 6,531,142 | B1 | 3/2003  | Rabe et al. |
| 6,693,102 | B2 | 2/2004  | Stasch et al. |
| 6,743,798 | B1 | 6/2004  | Straub et al. |
| 6,746,989 | B1 | 6/2004  | Muller et al. |
| 6,762,152 | B1 | 7/2004  | Muller et al. |
| 6,833,364 | B1 | 12/2004 | Straub et al. |
| 6,838,415 | B1 | 1/2005  | Muller et al. |
| 6,864,287 | B1 | 3/2005  | Alonso-Alija et al. |
| 6,924,251 | B1 | 8/2005  | Schwarz et al. |
| 6,969,697 | B2 | 11/2005 | Muller et al. |
| 7,080,644 | B2 | 7/2006  | Gumaste et al. |
| 7,642,275 | B2 | 1/2010  | Bressi et al. |
| 7,674,825 | B2 | 3/2010  | Alonso-Alija et al. |
| 8,084,481 | B2 | 12/2011 | Meier et al. |
| 8,202,895 | B2 | 6/2012  | Brüggemeier et al. |
| 2001/0020100 | A1 | 9/2001  | Manning et al. |
| 2002/0045651 | A1 | 4/2002  | Brenner et al. |
| 2002/0172644 | A1 | 11/2002 | Haslwanter et al. |
| 2003/0161790 | A1 | 8/2003  | Wahi et al. |
| 2004/0071757 | A1 | 4/2004  | Rolf et al. |
| 2004/0082798 | A1 | 4/2004  | Alonso-Alija et al. |
| 2004/0176446 | A1 | 9/2004  | Alonso-Alija et al. |
| 2006/0148779 | A1 | 7/2006  | Bell et al. |
| 2007/0225333 | A1 | 9/2007  | Bryans et al. |
| 2007/0281937 | A1 | 12/2007 | Zelle et al. |
| 2008/0058314 | A1 | 3/2008  | Alonso-Alija et al. |
| 2008/0139560 | A1 | 6/2008  | Zelle et al. |
| 2011/0245308 | A1 | 10/2011 | Bruggemeier et al. |
| 2012/0053218 | A1 | 3/2012  | Brüggemeier et al. |
| 2012/0208852 | A1 | 8/2012  | Fürstner et al. |
| 2012/0238607 | A1 | 9/2012  | Brüggemeier et al. |

(Continued)

FOREIGN PATENT DOCUMENTS

| EP | 0051829  | 5/1982 |
| WO | 99/31099 | 6/1999 |
| WO | 00/06568 | 2/2000 |

(Continued)

OTHER PUBLICATIONS

European Patent Office, International Search Report and Written Opinion for International Patent Application No. PCT/EP2015/075200, Dec. 4, 2015, 11 pages.

Arnswald, et al., "Unconventional Regiospecific Synthesis of Aromatic Carbonamides and Thiocarbonamides by Means of Tin-Mediated Friedel-Crafts Reactions", J. Org. Chem. 58(25), 1993, pp. 7022-7028.

Berge, et al., "Pharmaceutical Salts", J. Pharm. Sci. 66, Review Article, 1977, pp. 1-19.

Bronson, et al., "Discovery of the First Antibactrial Small Molecule Inhibitors of MurB", Bioorganic & Medicinal Chemistry Letters, 13, 2003, pp. 873-875.

Chan, et al., "Copper promoted C—N and C—O bond cross-coupling with pyridylboronates", Tetrahedron Letters 44, 2003, pp. 3863-3865.

(Continued)

*Primary Examiner* — Alicia L Otton
(74) *Attorney, Agent, or Firm* — Nixon & Vanderhye P.C.

(57) ABSTRACT

The present invention relates to novel 5-(hydroxyalkyl)-1-phenyl-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of cardiovascular and renal diseases.

15 Claims, No Drawings

(56) References Cited

U.S. PATENT DOCUMENTS

2013/0225646 A1   8/2013   Fürstner et al.

FOREIGN PATENT DOCUMENTS

| WO | 00/06569 | 2/2000 |
|---|---|---|
| WO | 00/59510 | 10/2000 |
| WO | 01/00595 | 1/2001 |
| WO | 01/19355 | 3/2001 |
| WO | 01/19776 | 3/2001 |
| WO | 01/19778 | 3/2001 |
| WO | 01/19780 | 3/2001 |
| WO | 02/42301 | 5/2002 |
| WO | 02/066447 | 8/2002 |
| WO | 02/070462 | 9/2002 |
| WO | 02/070510 | 9/2002 |
| WO | 03/095451 | 11/2003 |
| WO | 2005/006892 | 1/2005 |
| WO | 2005/063754 | 7/2005 |
| WO | 2005/105779 | 11/2005 |
| WO | 2006/117657 | 11/2006 |
| WO | 2011/104322 | 9/2011 |
| WO | 2011/147809 | 12/2011 |
| WO | 2012/004258 | 1/2012 |
| WO | 2012/028647 | 3/2012 |
| WO | 2012/059549 | 5/2012 |
| WO | 2013/138860 | 9/2013 |

OTHER PUBLICATIONS

Chang, et al., "Triazolinones as Nonpeptide Angiotensin II Antagonists. 1. Synthesis and Evaluation of Potent 2, 4, 5-Trisubstituted Triazoloinones", J. Med. Chem., vol. 36, Nr. 17, 1993, pp. 2558-2568.

DeLuca, et al., "Hyponatremia in Paitents with Heart Failure", Am. J. Cardiel, vol. 96 (suppl.), Dec. 19, 2005, pp. 19L-23L.

Dobosz, et al., "Synthesis and Some Pharmacological Properties of 3-(4-phenyl-5-oxo-1,2,4-triazolin-1-ylmethyl)-1,2,-triazolin-5-thione Derivatives", Acta Poloniae Pharmaceutica, vol. 59, No. 4, 2002, pp. 281-290.

Finley, et al., "Arginine Vasopressin Antagonists for the Treatment of Heart Failure and Hyponatremia", Circulation 118, col. 2, 2008, pp. 410-421.

Francis, et al., "Comparison of Neuroendocrine Activation in Patients with Left Ventricular Dysfunction with and without Congestive Heart Failure", Circulation 82(5), Downloaded from http://circ.ahajournals.org/ at Bayer Pharma AG on Aug. 26, 2015, Nov. 1990, pp. 1724-1729.

Gines, et al., "Effects of stavaptan, a selective vasopressin V2 receptor antagonist, on ascites and serum sodium cirrhosis with hyponatremia", Hepatology, 48(1), 2008, pp. 204-212.

Goldsmith, et al., "Current treatments and novel pharmacologic treatments for hyponatremia in congestive heart failure", Am. J. Cardiel, 95(suppl), 2005, pp. 14B-23B.

Hassan, et al., "Aryl-Aryl Bond Formation One Century after the Discovery of the Ulmann Reaction", Chem Rev 102, 2002, pp. 1359-1469.

Illarionov, et al., "Sequence of the cDNA encodeng the Ca2+-activated photoprotein obelin from the hydroid polyp Obelia longissima", Gene, 153, 1995, pp. 273-274.

Kahn, et al., "Management of cardiovascular disease in patients with kidney disease", Nature Reviews, Cardiology, vol. 10, May 2013, pp. 261-273.

Lemmens-Gruber, et al., "Vasopressin Antagonists", Cell. Mal. Life Sci. 63, 2006, pp. 1766-1779.

Milligan, et al., "$G_{16}$ as a universal G protein adapter:implications for agonist screening strategies", Trends in Pharmacological Sciences, vol. 17, Current Awareness, Jul. 1996, pp. 235-237.

Palm, et al., "Vasopressin Antagonists as Aquaretic Agents for the Treatment of Hyponatremia", Am. J. Med. 119(7A), 2006, pp. S87-S92.

Papadopoulos, et al., "Friedel-Crafts Thioacylation with Ethoxycarbonyl Isothiocyanate: A One-Step Synthesis of Aromatic Thioamides", J. Org. Chem. 41(6), 1976, pp. 962-965.

Patani, et al., "Bioisosterism: A Rational Approach in Drug Design", Chem. Rev., 96, 1996, pp. 3147-3176.

Qiao, et al., "Copper-Promoted Carbon-Heteroatom Bond Cross-Coupling with Boronic Acids and Derivatives", Synthesis, No. 6, 2011, pp. 829-856.

Rao, et al., "Chan-Lam coupling reactions: synthesis of heterocycles", Tetrahedron 68, Tetrahedron report No. 983, 2012, 7735-7754.

Rizzuto, et al., "Rapid changes of mitochondrial Ca2+ revealed by specifically targeted recombinant aequorin", Nature vol. 358, Jul. 23, 1992, pp. 325-327.

Sanghi, et al., "Vasopressin antagonism: a future treatment option in heart failure", European Heart Journal, 26, 2005, pp. 538-543.

Schrier, et al., "Hormones and Hemodynamics in Heart Failure", New Engl. J. Med 341(8), Aug. 19, 1999, pp. 577-585.

Schrier, "The sea within us: Disorders of body water homeostasis", Current Opinion in Investigational Drugs, 8(4), 2007, pp. 304-311.

Tang, et al., "Vasopressin Receptor Antagonists in the Management of Acute Heart Failure", Expert Opin. Investig. Drugs 14(5), 2005, pp. 593-600.

Verbalis, J.G, "AVP receptor antagonists as aquaretics: Review and assessment of clinical data", Cleveland Clinic Journal of Medicine, 73, Sep. 2009, pp. S24-S33.

HYDROXYALKYL-SUBSTITUTED PHENYLTRIAZOLE DERIVATIVES AND USES THEREOF

The present invention relates to novel 5-(hydroxyalkyl)-1-phenyl-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of cardiovascular and renal diseases.

The liquid content of the human body is subject to various physiological control mechanisms, the purpose of which is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centers in the brain regulates drinking behaviour and controls fluid excretion via the kidneys by means of humoral and neural signals. The peptide hormone vasopressin is of central importance in this [Schrier R. W., Abraham W. T., *New Engl. J. Med.* 341, 577-585 (1999)].

Vasopressin is produced in specialized endocrine neurons in the Nucleus supraopticus and N. paraventricularis in the wall of the third ventricle (hypothalamus) and is transported from there along the neural processes into the posterior lobes of the hypophysis (neurohypophysis). There the hormone is released into the bloodstream in response to stimulus. A loss of volume, e.g. as a result of acute bleeding, heavy sweating, prolonged thirst or diarrhoea, is a stimulus for intensified release of the hormone. Conversely, the secretion of vasopressin is inhibited by an increase in the intravascular volume, e.g. as a result of increased fluid intake.

Vasopressin exerts its action mainly via binding to three receptors, which are classified as V1a, V1b and V2 receptors and which belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this disease excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Consequently, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that with V2 antagonist drugs, volume homeostasis can be restored without affecting electrolyte homeostasis. Hence, drugs with V2 antagonistic activity appear particularly suitable for the treatment of all disease conditions which are associated with an overloading of the body with water, without the electrolytes being adequately increased in parallel.

A significant electrolyte abnormality is measurable in clinical chemistry as hyponatremia (sodium concentration <135 mmol/L); it is the most important electrolyte abnormality in hospital patients, with an incidence of about 5% or 250 000 cases per year in the US alone. If the plasma sodium concentration falls below 115 mmol/L, comatose states and death are imminent. Depending on the underlying cause, a distinction is made between hypovolemic, euvolemic and hypervolemic hyponatremia. The forms of hypervolemia with edema formation are clinically significant. Typical examples of these are the syndrome of inappropriate ADH/vasopressin secretion (SIADH) (e.g. after craniocerebral trauma or as paraneoplasia in carcinomas) and hypervolemic hyponatremia in liver cirrhosis, various renal diseases and heart failure [De Luca L. et al., *Am. J. Cardiol.* 96 (suppl.), 19L-23L (2005)]. In particular, patients with heart failure, in spite of their relative hyponatremia and hypervolemia, often display elevated vasopressin levels, which are seen as the consequence of a generally disturbed neurohumoral regulation in heart failure [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavourable hemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, agents which inhibit the action of vasopressin on the V2 and/or the V1a receptor appear suitable for the treatment of heart failure. In particular, compounds with combined activity on both vasopressin receptors (V1a and V2) should have both desirable renal as well as hemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and, as a result, may lead to a further compensatory increase in vasopressin release. Through this, in the absence of a component simultaneously blocking the V1a receptor, the harmful effects of vasopressin, such as for example vasoconstriction and heart muscle hypertrophy, could be further intensified [Saghi P. et al., *Europ. Heart J.* 26, 538-543 (2005)].

Certain 4-phenyl-1,2,4-triazol-3-yl derivatives have been described in WO 2005/063754-A1 and WO 2005/105779-A1 to act as vasopressin V1a receptor antagonists that are useful for the treatment of gynecological disorders, notably menstrual disorders such as dysmenorrhea.

In WO 2011/104322-A1, a particular group of bis-aryl-bonded 1,2,4-triazol-3-ones, including 5-phenyl-1,2,4-triazol-3-yl and 1-phenyl-1,2,3-triazol-4-yl derivatives thereof, has been disclosed as antagonists of vasopressin V1a and/or V2 receptors being useful for the treatment and/or prevention of cardiovascular diseases. During further investigation of this structural class it emerged, however, that candidate compounds were frequently compromised by an unsatisfactory aquaretic potency when evaluated in vivo following peroral administration to conscious rats. Yet, as outlined above, a robust aquaretic efficacy is a desirable prerequisite for the treatment of disease conditions that are associated with an overloading of the body with water, such as, for example, in congestive heart failure.

A significant increase in aquaretic potency would also help towards reducing the amount of substance which is going to be required to achieve and maintain the desired therapeutic effect, thus limiting the potential for unacceptable side effects and/or unwanted drug-drug interactions during the treatment of patients which might already be at high risk, such as, for example, in acute or chronic heart failure or renal failure.

The technical problem to be solved according to the present invention may therefore be seen in identifying and providing new compounds that act as potent antagonists of both vasopressin V1a and V2 receptors and, in addition, exhibit a substantial increase in aquaretic potency in vivo.

Surprisingly, it has now been found that certain 5-(hydroxyalkyl)-1-phenyl-1,2,4-triazole derivatives represent highly potent dual antagonists of vasopressin V1a and V2 receptors exhibiting significantly enhanced aquaretic potency in vivo after oral application. This improved activity profile renders the compounds of the present invention particularly useful for the treatment and/or prevention of cardiovascular and renal diseases.

In one aspect, the present invention relates to 5-(hydroxyalkyl)-1-phenyl-1,2,4-triazole derivatives of the general formula (I)

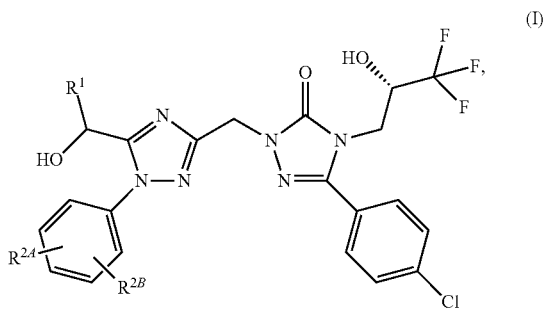

(I)

wherein
$R^1$ is hydrogen or methyl,
and
$R^{2A}$ and $R^{2B}$ are independently selected from the group consisting of hydrogen, fluoro, chloro, cyano, methyl, fluoromethyl, difluoromethyl, trifluoromethyl, ethyl, methoxy, difluoromethoxy and trifluoromethoxy.

The compounds according to this invention can also be present in the form of their salts, solvates and/or solvates of the salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as process products and/or embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation, purification or storage of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

In a distinct embodiment, the present invention relates to compounds of formula (I), wherein $R^1$ is methyl.

In a further distinct embodiment, the present invention relates to compounds of formula (I), wherein at least one of $R^{2A}$ and $R^{2B}$ is other than hydrogen.

In another distinct embodiment, the present invention relates to compounds of formula (I), wherein
$R^1$ is hydrogen or methyl,
and
$R^{2A}$ and $R^{2B}$ are independently selected from the group consisting of hydrogen, fluoro, chloro, methyl and methoxy, wherein at least one of $R^{2A}$ and $R^{2B}$ is other than hydrogen.

In a preferred embodiment, the present invention relates to compounds according to formula (I) selected from the group consisting of the following compounds 5-(4-chlorophenyl)-2-{[1-(3-chlorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one;

5-(4-chlorophenyl)-2-{[1-(3-fluorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one;

5-(4-chlorophenyl)-2-{[5-(hydroxymethyl)-1-(2-methylphenyl)-1H-1,2,4-triazol-3-yl]methyl}-4-[(2S)-3,3,3-trifluoro-2-hydroxypropyl]-2,4-dihydro-3H-1,2,4-triazol-3-one;

2-({1-(2-chloro-4-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one;

2-{[1-(2-chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1);

2-{[1-(2-chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2);

2-({1-(2-chloro-5-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one;

2-{[1-(2-chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1);

2-{[1-(2-chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2);

5-(4-chlorophenyl)-2-({1-(3-fluorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(3-fluorophenyl)-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

5-(4-chlorophenyl)-2-({1-(3-fluorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

5-(4-chlorophenyl)-2-({1-(3-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(3-chlorophenyl)-5-[(1R)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

5-(4-chlorophenyl)-2-({1-(2-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(2-chlorophenyl)-5-[(1R)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

and 5-(4-chlorophenyl)-2-({1-(2-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one.

In a particularly preferred embodiment, the present invention relates to compounds according to formula (I) selected from the group consisting of the following compounds 5-(4-chlorophenyl)-2-({1-(3-fluorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(3-fluorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

5-(4-chlorophenyl)-2-({1-(3-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

5-(4-chlorophenyl)-2-({1-(2-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one;

and 5-(4-chlorophenyl)-2-({1-(2-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one.

In a further embodiment, the present invention relates to a process for preparing the compounds of the general formula (I), characterized in that a compound of formula (II)

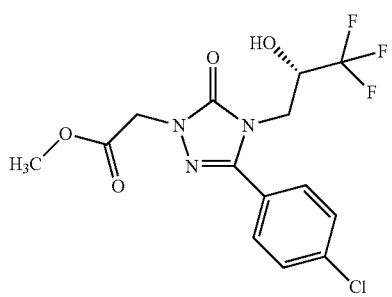

(II)

is first reacted with hydrazine to give the hydrazide of formula (III)

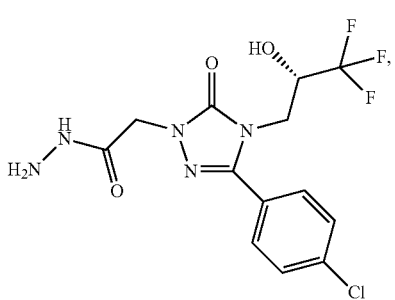

(III)

then condensed with an amidine of formula (IV)

(IV)

or a salt thereof,
wherein $R^1$ has the meaning described above,
in the presence of a base to give a 1,2,4-triazole derivative of formula (V)

(V)

and/or a tautomer thereof,
wherein $R^1$ has the meaning described above,
and subsequently coupled with a phenylboronic acid of formula (VI)

(VI)

wherein $R^{2A}$ and $R^{2B}$ have the meanings described above,
in the presence of a copper catalyst and an amine base to yield the target compound of formula (I)

(I)

wherein $R^1$, $R^{2A}$ and $R^{2B}$ have the meanings described above,
optionally followed, where appropriate, by (i) separating the compounds of formula (I) thus obtained into their respective diastereomers, preferably using chromatographic methods, and/or (ii) converting the compounds of formula (I) into their respective hydrates, solvates, salts and/or hydrates or solvates of the salts by treatment with the corresponding solvents and/or acids or bases.

Compounds of formula (I), wherein $R^1$ represents methyl, can also be obtained in diastereomerically pure form by employing the appropriate enantiomer of amidine (IV) [$R^1$=methyl], i.e. (IV-A) or (IV-B)

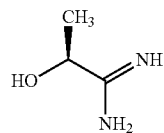

(IV-A)

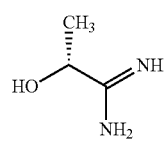

(IV-B)

or a salt thereof, in the condensation reaction described above.

The transformation (II)→(III) is carried out in the usual way by treating methyl ester (II) with hydrazine or hydrazine hydrate in an alcoholic solvent, such as methanol, ethanol, n-propanol, isopropanol or n-butanol, at a temperature in the range of +20° C. to +100° C.

The condensation reaction (III)+(IV)→(V) is usually carried out in an inert dipolar-aprotic solvent, such as N,N-dimethylformamide (DMF), N,N-dimethylacetamide (DMA), dimethylsulfoxide (DMSO), N-methylpyrrolidinone (NMP) or N,N'-dimethylpropylene urea (DMPU), in the presence of a sufficiently strong base, such as sodium hydride or a sodium or potassium alkoxide, for example sodium or potassium methoxide, sodium or potassium ethoxide, or sodium or potassium tert-butoxide. The amidine (IV) may be employed as such in this reaction or in salt form, e.g. as the hydrochloride salt. In the latter case, a proportional excess of base is used. The reaction is generally performed at a temperature between +80° C. and +150° C. Heating by means of a microwave reactor device may have a beneficial effect for this condensation reaction.

The 1,2,4-triazole derivative of formula (V) produced by this reaction may also be present in other tautomeric forms, such as (V-A) or (V-B)

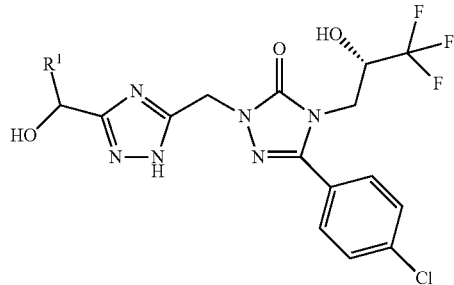

(V-A)

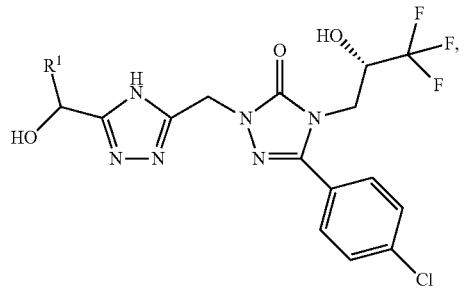

(V-B)

or as a mixture of tautomers.

The coupling reaction (V)+(VI)→(I) is typically carried out with the aid of a copper catalyst and an amine base ["Chan-Lam coupling" conditions; see, for instance, D. M. T. Chan et al., Tetrahedron Lett. 44 (19), 3863-3865 (2003); J. X. Qiao and P. Y. S. Lam, Synthesis, 829-856 (2011); K. S. Rao and T.-S. Wu, Tetrahedron 68, 7735-7754 (2012)]. Copper catalysts suitable for this process are in particular copper(II) salts, such as copper(II) acetate, copper(II) trifluoromethanesulfonate or copper(II) bromide. Practical amine bases include, for example, triethylamine, N,N-diisopropylethylamine, pyridine and 4-(N,N-dimethylamino) pyridine. The reaction is performed in an inert organic solvent, such as dichloromethane, 1,2-dichloroethane, methyl tert-butyl ether, tetrahydrofuran, 1,4-dioxane, 1,2-dimethoxyethane, toluene, pyridine, ethyl acetate, acetonitrile or N,N-dimethylformamide, or in a mixture of these solvents. Preferably, pyridine is used both as solvent and base. The coupling is generally carried out at a temperature in the range of +20° C. to +120° C., preferably at +20° C. to +70° C. Concomitant microwave irradiation may have a beneficial effect in this reaction as well.

Regioisomeric phenyltriazole derivatives which may arise from a coupling reaction occurring at other triazole nitrogen atoms [cf. tautomers (V-A), (V-B)] can, in the event, be readily separated from the target product (I) by conventional HPLC chromatography.

The compound of formula (II) can be synthesized by the procedures described in Int. Pat. Appl. WO 2011/104322-A1 (see also synthesis schemes 1a and 1b below).

The compounds of the formulae (IV), (IV-A), (IV-B) and (VI) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The preparation of the compounds of the invention may be illustrated by means of the following synthesis schemes:

Scheme 1a

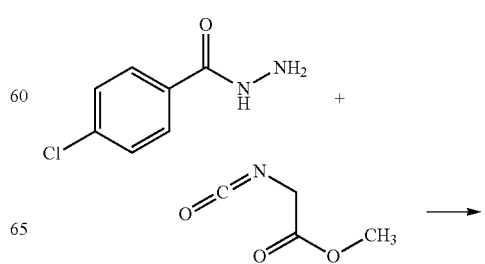

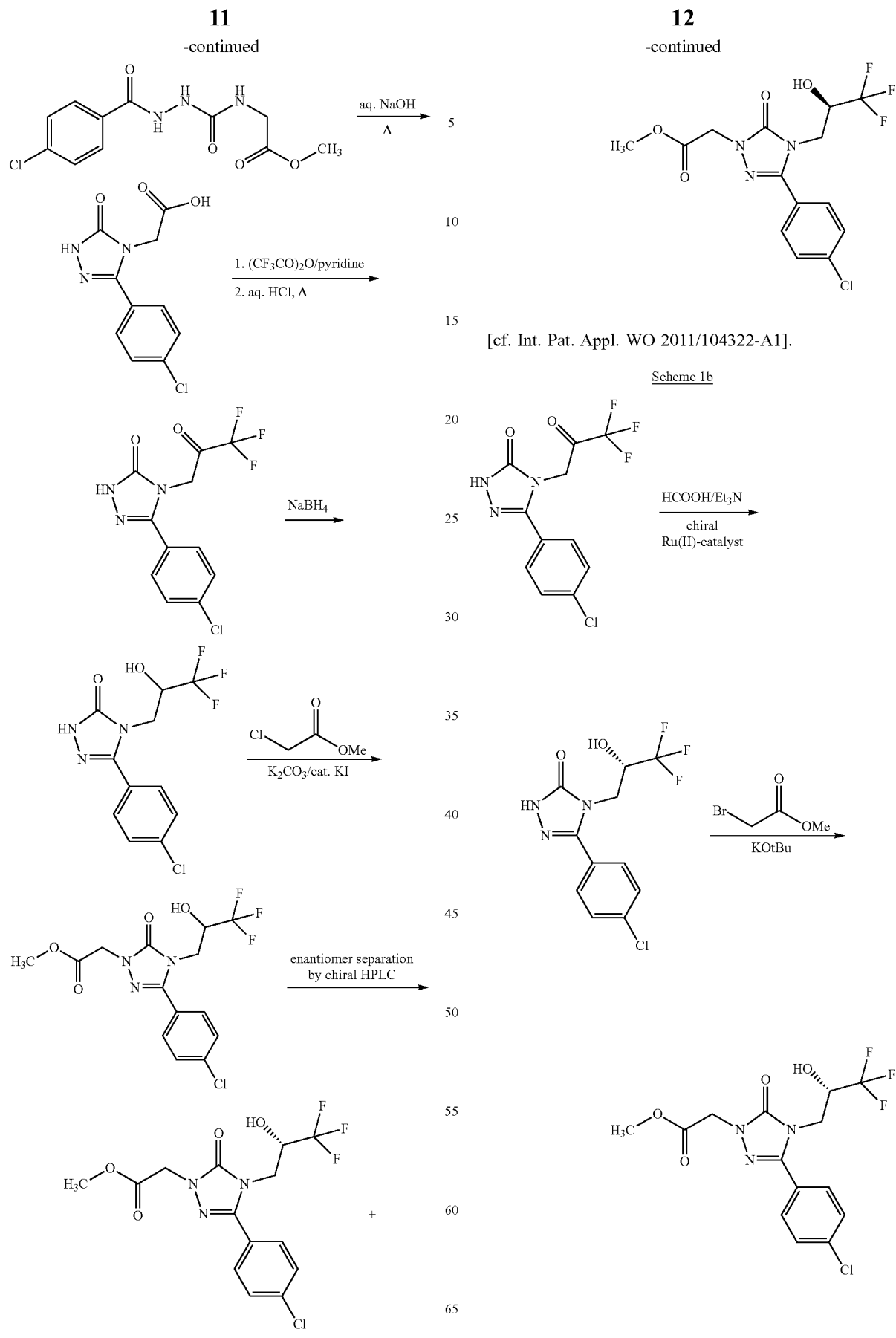
[cf. Int. Pat. Appl. WO 2011/104322-A1].

Scheme 2

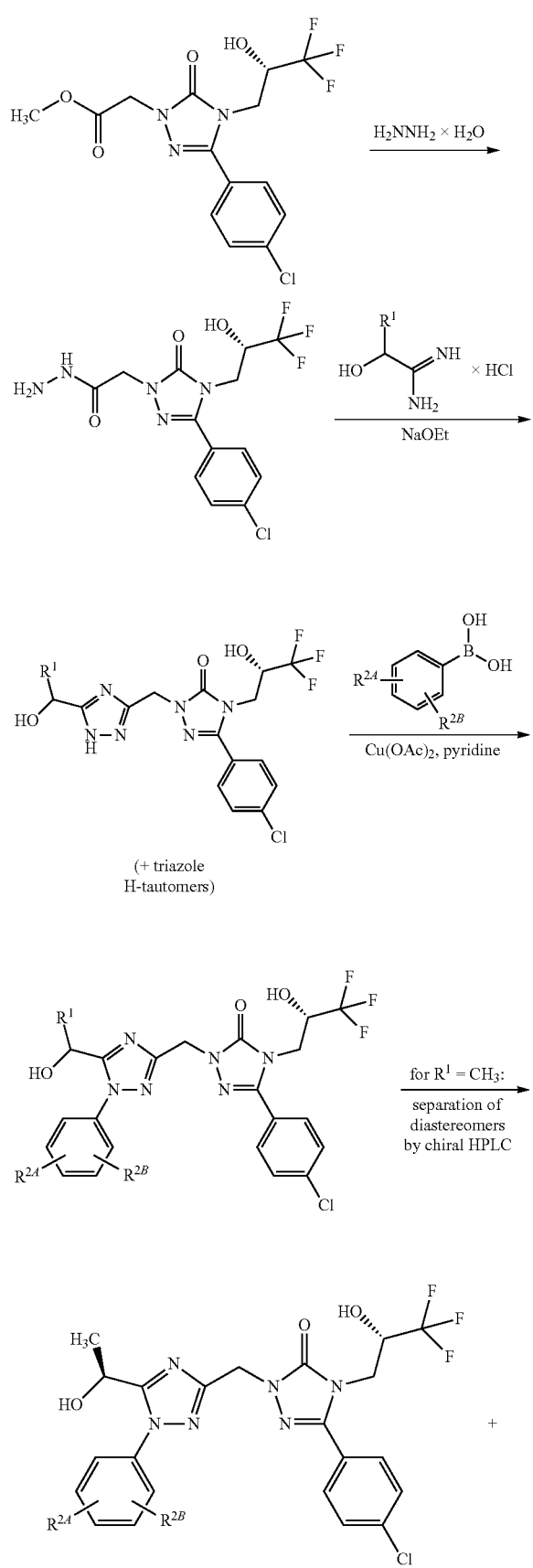

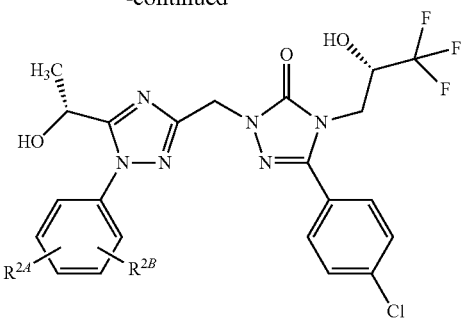

The compounds of the present invention have valuable pharmacological properties and can be used for the prevention and/or treatment of various diseases and disease-induced states in humans and other mammals.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

The compounds of the present invention are highly potent dual antagonists of vasopressin V1a and V2 receptors. In addition, the compounds of the invention exhibit a pronounced aquaretic effect in vivo after oral application. The compounds of the invention are therefore expected to be highly valuable as therapeutic agents for the treatment and/or prevention of diseases, in particular for the treatment and/or prevention of cardiovascular and renal diseases.

Cardiovascular diseases in this context that may be treated and/or prevented with the compounds of the invention include, but are not limited to, the following: acute and chronic heart failure including worsening chronic heart failure (or hospitalization for heart failure) and congestive heart failure, arterial hypertension, resistant hypertension, arterial pulmonary hypertension, coronary heart disease, stable and unstable angina pectoris, atrial and ventricular arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node re-entry tachycardia and Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction), furthermore thromboembolic diseases and ischaemias such as peripheral perfusion disturbances, reperfusion injury, arterial and venous thromboses, myocardial insufficiency, endothelial dysfunction, micro- and macrovascular damage (vasculitis) and for preventing restenoses such as after thrombolysis therapies, percutaneous transluminal angioplasty (PTA), percutaneous transluminal coronary angioplasty (PTCA), heart transplantation and bypass operations, arteriosclerosis, disturbances of lipid metabolism, hypolipoproteinaemias, dyslipidaemias, hypertriglyceridaemias, hyperlipidaemias and combined hyperlipidaemias, hypercholesterolaemias, abetalipoproteinaemia, sitosterolaemia, xanthomatosis, Tangier disease, adipositas, obesity, metabolic syndrome, transitory and ischaemic attacks, stroke, inflammatory cardiovascular diseases, peripheral and cardiac vascular diseases, peripheral circulation disorders, spasms of the coronary arteries and peripheral arteries, and edema such as, for example, pulmonary edema, cerebral edema, renal edema and heart failure-related edema.

In the sense of the present invention, the term heart failure also includes more specific or related disease forms such as right heart failure, left heart failure, global insufficiency, ischaemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, heart failure with preserved ejection fraction (HFpEF or diastolic heart failure), and heart failure with reduced ejection fraction (HFrEF or systolic heart failure).

The compounds according to the invention are also suitable for the treatment and/or prevention of renal diseases, in particular of acute and chronic renal insufficiency, and of acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism.

The compounds of the present invention may be particularly useful for the treatment and/or prevention of the cardiorenal syndrome (CRS) and its various subtypes. This term embraces certain disorders of the heart and kidneys whereby acute or chronic dysfunction in one organ may induce acute or chronic dysfunction of the other. CRS has been sub-classified into five types based upon the organ that initiated the insult as well as the acuity and chronicity of the disease (type 1: development of renal insufficiency resulting from acute decompensated heart failure; type 2: chronic congestive heart failure resulting in progressive renal dysfunction; type 3: acute cardiac dysfunction resulting from an abrupt fall in renal function; type 4: chronic kidney disease leading to cardiac remodeling; type 5: systemic disease involving both the heart and the kidneys) [see, for example, M. R. Kahn et al., *Nature Rev. Cardiol.* 10, 261-273 (2013)].

The compounds according to the invention are also suitable for the treatment and/or prevention of polycystic kidney disease (PCKD) and of the syndrome of inadequate ADH secretion (SIADH). Furthermore, the compounds of the invention are suitable for use as a diuretic for the treatment of edemas and in electrolyte disorders, in particular in hypervolemic and euvolemic hyponatremia.

Moreover, the compounds according to the invention may be used for the treatment and/or prevention of primary and secondary Raynaud's phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds of the invention are suitable for treating urological diseases and diseases of the male and female urogenital system such as, for example, benign prostatic syndrome (BPS), benign prostatic hyperplasia (BPH), benign prostatic enlargement (BPE), bladder outlet obstruction (BOO), lower urinary tract syndromes (LUTS), neurogenic overactive bladder (OAB), interstitial cystitis (IC), urinary incontinence (UI), for example mixed, urge, stress and overflow incontinence (MUI, UUI, SUI, OUI), pelvic pains, erectile dysfunction and female sexual dysfunction.

The compounds according to the invention may also be used for the treatment and/or prevention of inflammatory diseases, asthmatic diseases, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF). In addition, the compounds of the invention may be used for the treatment and/or prevention of pulmonary arterial hypertension (PAH) and other forms of pulmonary hypertension (PH), including pulmonary hypertension associated with left ventricular disease, HIV infection, sickle cell anaemia, thromboembolism (CTEPH), sarcoidosis, chronic obstructive pulmonary disease (COPD) or pulmonary fibrosis.

Additionally, the compounds according to the invention may be used for the treatment and/or prevention of liver cirrhosis, ascites, diabetes mellitus and diabetic complications such as, for example, neuropathy and nephropathy. Further, the compounds of the invention are suitable for the treatment and/or prevention of central nervous disorders such as anxiety states and depression, of glaucoma and of cancer, in particular of pulmonary tumors, and for the management of circadian rhythm misalignment such as jet lag and shift work.

Furthermore, the compounds according to the invention may be useful for the treatment and/or prevention of pain conditions, diseases of the adrenals such as, for example, pheochromocytoma and adrenal apoplexy, diseases of the intestine such as, for example, Crohn's disease and diarrhea, menstrual disorders such as, for example, dysmenorrhea, or of endometriosis, preterm labour and for tocolysis.

Due to their activity and selectivity profile, the compounds of the present invention are believed to be particularly suitable for the treatment and/or prevention of acute and chronic heart failure, cardiorenal syndrome (type 1-5), hypervolemic and euvolemic hyponatremia, liver cirrhosis, ascites, edema and the syndrome of inadequate ADH secretion (SIADH).

The diseases mentioned above have been well characterized in humans, but also exist with a comparable aetiology in other mammals, and may be treated in those with the compounds and methods of the present invention.

Thus, the present invention further relates to the use of the compounds according to the invention for the treatment and/or prevention of diseases, especially of the aforementioned diseases.

The present invention further relates to the use of the compounds according to the invention for preparing a pharmaceutical composition for the treatment and/or prevention of diseases, especially of the aforementioned diseases.

The present invention further relates to the use of the compounds according to the invention in a method for the treatment and/or prevention of diseases, especially of the aforementioned diseases.

The present invention further relates to a method for the treatment and/or prevention of diseases, especially of the aforementioned diseases, by using an effective amount of at least one of the compounds according to the invention.

Compounds of the present invention may be administered as the sole pharmaceutical agent or in combination with one or more additional therapeutic agents as long as this combination does not lead to undesirable and/or unacceptable side effects. Such combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single (fixed) oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil, tadalafil, udenafil, dasantafil, avanafil, mirodenafil or lodenafil;

positive-inotropic agents, such as for example cardiac glycosides (digoxin) and beta-adrenergic and dopaminergic agonists such as isoproterenol, adrenalin, noradrenalin, dopamine or dobutamine;

natriuretic peptides, such as for example atrial natriuretic peptide (ANP, anaritide), B-type natriuretic peptide or brain natriuretic peptide (BNP, nesiritide), C-type natriuretic peptide (CNP) or urodilatin;

calcium sensitizers, such as for example and preferably levosimendan;

NO- and heme-independent activators of soluble guanylate cyclase (sGC), such as in particular cinaciguat and also the compounds described in WO 01/19355, WO 01/19776, WO 01/19778, WO 01/19780, WO 02/070462 and WO 02/070510;

NO-independent, but heme-dependent stimulators of guanylate cyclase (sGC), such as in particular riociguat, vericiguat and also the compounds described in WO 00/06568, WO 00/06569, WO 02/42301, WO 03/095451, WO 2011/147809, WO 2012/004258, WO 2012/028647 and WO 2012/059549;

inhibitors of human neutrophil elastase (HNE), such as for example sivelestat or DX-890 (reltran);

compounds inhibiting the signal transduction cascade, in particular tyrosine and/or serine/threonine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds influencing the energy metabolism of the heart, such as for example and preferably etomoxir, dichloroacetate, ranolazine or trimetazidine, or full or partial adenosine A1 receptor agonists;

compounds influencing the heart rate, such as for example and preferably ivabradine;

cardiac myosin activators, such as for example and preferably omecamtiv mecarbil (CK-1827452);

antithrombotic agents, for example and preferably from the group of platelet aggregation inhibitors, anticoagulants and profibrinolytic substances;

blood pressure lowering agents, for example and preferably from the group of calcium antagonists, angiotensin AII antagonists, ACE inhibitors, vasopeptidase inhibitors, endothelin antagonists, renin inhibitors, alpha-blockers, beta-blockers, mineralocorticoid receptor antagonists and diuretics; and/or fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants and profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or enoxaparin.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

Blood pressure lowering agents are preferably to be understood as compounds from the group of calcium antagonists, angiotensin AII antagonists, ACE inhibitors, vasopeptidase inhibitors, endothelin antagonists, renin inhibitors, alpha-blockers, beta-blockers, mineralocorticoid receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin or tamsulosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII receptor antagonist, for example and preferably losartan, candesartan, valsartan, telmisartan, irbesartan, olmesartan, eprosartan or azilsartan.

In a preferred embodiment of the invention, the compounds according to the invention are administered in combination with a vasopeptidase inhibitor or inhibitor of neutral endopeptidase (NEP), such as for example and preferably sacubitril, omapatrilat or AVE-7688.

In a preferred embodiment of the invention, the compounds according to the invention are administered in combination with a dual angiotensin AII receptor antagonist/NEP inhibitor (ARNI), for example and preferably LCZ696.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan, tezosentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably finerenone, spironolactone, canrenone, potassium canrenoate or eplerenone.

In a preferred embodiment of the invention, the compounds according to the invention are administered in combination with a diuretic, such as for example and preferably furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorothalidone, metolazone, quinethazone, acetazolamide, dichlorophenamide, methazolamide, glycerine, isosorbide, mannitol, amiloride or triamterene.

Fat metabolism altering agents are preferably to be understood as compounds from the group of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, for example and preferably dalcetrapib, anacetrapib, BAY 60-5521 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, R-103757, BMS-201038 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

In a particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, organic nitrates, NO donors, activators of the soluble guanylate cyclase (sGC), stimulators of the soluble guanylate cyclase and positive-inotropic agents.

Thus, in a further embodiment, the present invention relates to pharmaceutical compositions comprising at least one of the compounds according to the invention and one or more additional therapeutic agents for the treatment and/or prevention of diseases, especially of the aforementioned diseases.

Furthermore, the compounds of the present invention may be utilized, as such or in compositions, in research and diagnostics, or as analytical reference standards and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically suitable excipients, and to the use thereof for the treatment and/or prevention of diseases, especially of the aforementioned diseases.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, otic or topical route, or as an implant or stent.

For these administration routes, the compounds of the invention can be administered in suitable application forms.

Suitable for oral administration are application forms which function according to the state of the art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g. hard or soft gelatin capsules), sugar-coated tablets, granules, pellets, powders, emulsions, suspensions, aerosols or solutions.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Suitable parenteral application forms include injection and infusion preparations in the form of solutions, suspensions, emulsions, lyophilisates and sterile powders.

Forms suitable for other application routes include, for example, inhalatory pharmaceutical forms (e.g. powder inhalers, nebulizers), nasal drops, solutions or sprays, tablets or capsules to be administered lingually, sublingually or buccally (e.g. troches, lozenges), suppositories, ear and eye preparations (e.g. drops, ointments), vaginal capsules, aqueous suspensions (lotions, shaking mixtures), lipophilic suspensions, ointments, creams, milks, pastes, foams, dusting powders, transdermal therapeutic systems (e.g. patches), implants and stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The compounds according to the invention can be converted into the recited application forms in a manner known per se by mixing with inert, non-toxic, pharmaceutically suitable excipients. These excipients include, inter alia, carriers (e.g. microcrystalline cellulose, lactose, mannitol), solvents (e.g. liquid polyethylene glycols), emulsifiers (e.g. sodium dodecyl sulfate), surfactants (e.g. polyoxysorbitan oleate), dispersants (e.g. polyvinylpyrrolidone), synthetic and natural polymers (e.g. albumin), stabilizers (e.g. antioxidants such as, for example, ascorbic acid), colorants (e.g. inorganic pigments such as, for example, iron oxides), and flavour and/or odour masking agents.

A preferred dose of the compound of the present invention is the maximum that a patient can tolerate and not develop serious side effects. Illustratively, the compound of the present invention may be administered parenterally at a dose of about 0.001 mg/kg to about 10 mg/kg, preferably of about 0.01 mg/kg to about 1 mg/kg of body weight. In oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, the bioavailability and pharmacodynamic characteristics of the particular compound and its mode and route of administration, the time or interval over which administration takes place, the dose regimen selected, the response of the individual patient to the active ingredient, the specific disease involved, the degree of or the involvement or severity of the disease, the kind of concurrent treatment (i.e., the interaction of the compound of the invention with other co-administered therapeutics), and other relevant circumstances.

Thus, it may be satisfactory in some cases to manage with less than the aforementioned minimum amount, whereas in other cases the stated upper limit must be exceeded. Treatment can be initiated with smaller dosages, which are less than the optimum dose of the compound. Thereafter, the dosage may be increased by small increments until the optimum effect under the circumstances is reached. For convenience, the total daily dosage may be divided and administered in individual portions spread over the day.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

A. EXAMPLES

Abbreviations and Acronyms:
Ac acetyl
aq. aqueous (solution)
br. broad ($^1$H NMR signal)
cat. catalytic
conc. concentrated
d doublet ($^1$H NMR signal)
DCI direct chemical ionization (MS)
d.e. diastereomeric excess
DMF N,N-dimethylformamide
DMSO dimethylsulfoxide
EI electron impact ionization (MS)
eq. equivalent(s)
ESI electro-spray ionization (MS)
Et ethyl
h hour(s)
$^1$H NMR proton nuclear magnetic resonance spectroscopy
HPLC high performance liquid chromatography
LC/MS liquid chromatography-coupled mass spectroscopy
m multiplet ($^1$H NMR signal)
Me methyl
min minute(s)
MS mass spectroscopy
MTBE methyl tert-butyl ether
m/z mass-to-charge ratio (MS)
of th. of theory (chemical yield)
q quartet ($^1$H NMR signal)
quant. quantitative (yield)
rac racemic
Rf TLC retention factor
RP reverse phase (HPLC)
rt room temperature
$R_t$ retention time (HPLC)
s singlet ($^1$H NMR signal)
sat. saturated (solution)
SFC supercritical fluid chromatography
t triplet ($^1$H NMR signal)
tBu tert-butyl
tert tertiary
TFA trifluoroacetic acid
THF tetrahydrofuran
TLC thin layer chromatography
UV ultraviolet LC/MS and HPLC Methods:

Method 1 (LC/MS):
Instrument: Waters Acquity SQD UPLC System; column: Waters Acquity UPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 208-400 nm.

Method 2 (LC/MS):
Instrument: Waters Acquity SQD UPLC System; column: Waters Acquity UPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 95% A→6.0 min 5% A→7.5 min 5% A; oven: 50° C.; flow rate: 0.35 mL/min; UV detection: 210-400 nm.

Method 3 (LC/MS):
Instrument MS: Agilent MS Quad 6150; Instrument HPLC: Agilent 1290; column: Waters Acquity UPLC HSS T3 1.8μ, 50 mm×2.1 mm; eluent A: 1 L water+0.25 mL 99% formic acid, eluent B: 1 L acetonitrile+0.25 mL 99% formic acid; gradient: 0.0 min 90% A→0.3 min 90% A→1.7 min 5% A→3.0 min 5% A; oven: 50° C.; flow rate: 1.20 mL/min; UV detection: 205-305 nm.

Method 4 (Preparative HPLC):
Column: Chromatorex C18 10 μm, 125 mm×30 mm; eluent A: water+0.05% TFA, eluent B: acetonitrile+0.05% TFA; gradient: 20% B→45% B, 45% B isocratic, 45% B→80% B; column temperature: room temperature; flow rate: 50 mL/min; UV detection: 210 nm.

Starting Materials and Intermediates:

Example 1A

Methyl{3-(4-chlorophenyl)-5-oxo-4-[(2S)-3,3,3-trifluoro-2-hydroxypropyl]-4,5-dihydro-1H-1,2,4-triazol-1-yl}acetate

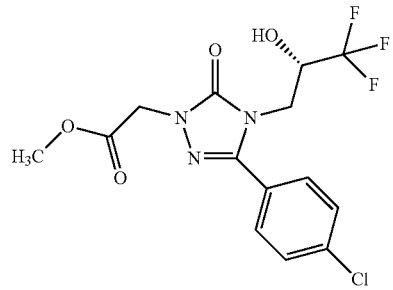

Under argon, potassium tert-butoxide (9.118 g, 81.26 mmol) was added portionwise at room temperature to a solution of 5-(4-chlorophenyl)-4-[(2S)-3,3,3-trifluoro-2-hydroxypropyl]-2,4-dihydro-3H-1,2,4-triazol-3-one (Example 5A in WO 2011/104322-A1; 20 g, 65.01 mmol) in THF (40 ml). To this solution was added methyl bromoacetate (10.939 g, 71.51 mmol), and the mixture was stirred at room temperature overnight. The reaction mixture was then diluted with water and extracted with ethyl acetate. The combined organic phases were dried over sodium sulfate, filtered, and concentrated in vacuo. 16.4 g (30.23 mmol) of the desired compound were obtained (46.5% yield, 70% purity).

LC/MS [method 1]: $R_t$=0.90 min; MS [ESIpos]: m/z=380 (M+H)$^+$ $^1$H NMR (400 MHz, DMSO-d$_6$): δ [ppm] 3.70 (s, 3H), 3.85 (dd, 1H), 4.00 (dd, 1H), 4.19-4.33 (m, 1H), 4.72 (s, 2H), 6.92 (d, 1H), 7.60-7.69 (m, 2H), 7.73-7.81 (m, 2H).

The title compound can also be synthesized via the procedure described in WO 2011/104322-A1 (Example 7A).

Example 2A

2-{3-(4-Chlorophenyl)-5-oxo-4-[(2S)-3,3,3-trifluoro-2-hydroxypropyl]-4,5-dihydro-1H-1,2,4-triazol-1-yl}acetohydrazide

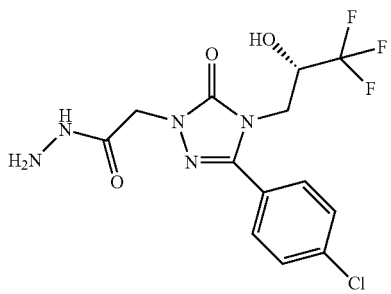 [SMILES: NNC(=O)Cn1nc(-c2ccc(Cl)cc2)n(C[C@H](O)C(F)(F)F)c1=O]

7.2 g (18.96 mmol) of methyl{3-(4-chlorophenyl)-5-oxo-4-[(2S)-3,3,3-trifluoro-2-hydroxypropyl]-4,5-dihydro-1H-1,2,4-triazol-1-yl}acetate were dissolved in 60 ml of absolute ethanol. To this solution were added 2.088 g (41.71 mmol) of hydrazine hydrate, and the mixture was stirred under reflux for 5 h and then at room temperature overnight. The resulting mixture was partially concentrated in vacuo and then diluted with water and extracted with ethyl acetate. The combined organic phases were dried over sodium sulfate, filtered, and concentrated in vacuo. The residue was dissolved in dichloromethane, and after crystallization the white solid was filtered off and dried under high vacuum. 7.02 g (18.49 mmol) of the desired compound were obtained (97.5% yield).

LC/MS [method 1]: $R_t$=0.73 min; MS [ESIpos]: m/z=380 (M+H)$^+$ $^1$H NMR (400 MHz, DMSO-d$_6$): δ [ppm] 3.82 (dd, 1H), 3.96 (dd, 1H), 4.24-4.34 (m, 3H), 4.38 (d, 2H), 6.90 (d, 1H), 7.61-7.66 (m, 2H), 7.73-7.78 (m, 2H), 9.23 (t, 1H).

Example 3A 5-(4-Chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one

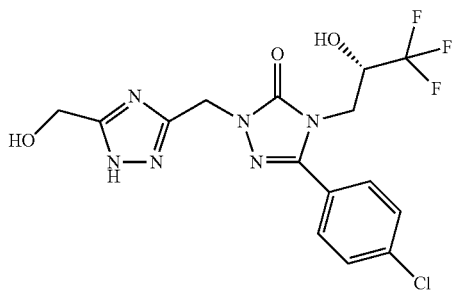 [SMILES: O=c1n(Cc2n[nH]c(CO)n2)nc(-c2ccc(Cl)cc2)n1C[C@H](O)C(F)(F)F]

Under argon, sodium ethoxide (2.987 g, 42.14 mmol, 96% purity) was added portionwise at room temperature to a solution of 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (8.0 g, 21.07 mmol) and 2-hydroxyacetamidine hydrochloride (2.329 g, 21.07 mmol) in DMF (200 ml). The reaction mixture was stirred at 100° C. overnight. After cooling, the reaction mixture was partially concentrated in vacuo and then diluted with ethyl acetate. The resulting mixture was washed with water, and after phase separation, the aqueous phase was extracted twice with ethyl acetate. The combined organic phases were dried over sodium sulfate, filtered, and concentrated under reduced pressure. The resulting solid was dried under high vacuum to give 8.69 g (89% purity, 18.47 mmol) of the desired compound which was used without further purification (~88% yield).

LC/MS [method 1]: $R_t$=0.74 min; MS [ESIpos]: m/z=419 (M+H)$^+$ $^1$H NMR (400 MHz, DMSO-d$_6$): δ [ppm] 3.83 (dd, 1H), 3.98 (dd, 1H), 4.24-4.36 (m, 1H), 4.53 (br. s, 2H), 4.96 (br. s, 2H), 5.64 (br. s, 1H), 6.91 (d, 1H), 7.58-7.67 (m, 2H), 7.72-7.78 (m, 2H), 13.75 (br. s, 1H).

Example 4A 5-(4-Chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

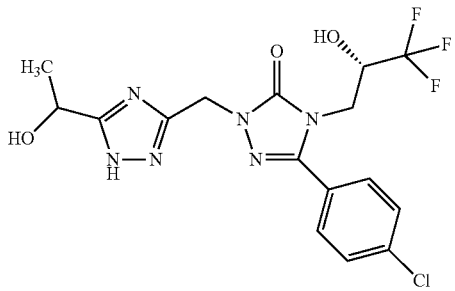 [SMILES: CC(O)c1nc(Cn2nc(-c3ccc(Cl)cc3)n(C[C@H](O)C(F)(F)F)c2=O)n[nH]1]

Under argon, sodium ethoxide (1.531 g, 21.59 mmol, 96% purity) was added portionwise at room temperature to a solution of 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (4.1 g, 10.80 mmol) and 2-hydroxypropanimidamide hydrochloride (1.480 g, 11.88 mmol) in DMF (110 ml). The reaction mixture was stirred at 120° C. for 4.5 h. After cooling, the reaction mixture was partially concentrated in vacuo and then diluted with ethyl acetate. The resulting mixture was washed with water, and after phase separation, the aqueous phase was extracted twice with ethyl acetate. The combined organic phases were dried over sodium sulfate, filtered, and concentrated under reduced pressure. The resulting solid was dried under high vacuum to give 4.90 g (92% purity, 10.42 mmol) of the desired compound as a mixture of diastereomers which was used without further purification.

LC/MS [method 1]: $R_t$=0.82 min; MS [ESIpos]: m/z=433 (M+H)$^+$ $^1$H NMR (400 MHz, DMSO-d$_6$): δ [ppm] 1.39 (d, 3H), 3.79-3.88 (m, 1H), 3.93-4.02 (m, 1H), 4.24-4.36 (m, 1H), 4.80 (quin, 1H), 4.89-5.00 (m, 2H), 5.73 (d, 1H), 6.93 (d, 1H), 7.58-7.65 (m, 2H), 7.70-7.77 (d, 2H), 13.68 (s, 1H).

Example 5A 5-(4-Chlorophenyl)-2-({5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one

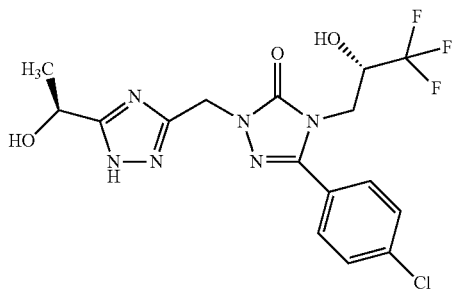 [SMILES: C[C@H](O)c1nc(Cn2nc(-c3ccc(Cl)cc3)n(C[C@H](O)C(F)(F)F)c2=O)n[nH]1]

The title compound was synthesized analogously to Example 4A starting from (2S)-2-hydroxypropanimidamide hydrochloride (1.1 eq.), using only 1.1 eq. of sodium ethoxide as base (reaction temperature: 100° C.).

LC/MS [method 1]: $R_t$=0.81 min; MS [ESIpos]: m/z=433 (M+H)$^+$.

(2S)-2-hydroxypropanimidamide hydrochloride, which is commercially available, was also synthesized from (2S)-2-hydroxypropanamide [L-(−)-lactamide] via the procedure described in WO 00/59510-A1 (Preparation 11, Step A) and WO 2013/138860-A1 (Intermediate to Precursor 82, p. 101-102).

Example 6A 5-(4-Chlorophenyl)-2-({5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one

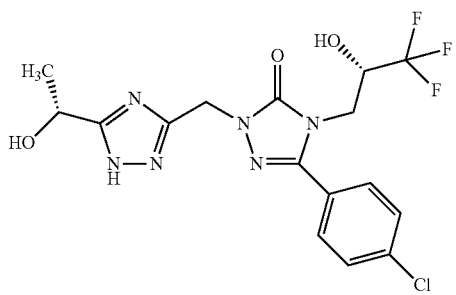

The title compound was synthesized analogously to Example 4A starting from (2R)-2-hydroxypropanimidamide hydrochloride (1.1 eq.), using only 1.1 eq. of sodium ethoxide as base (reaction temperature: 100° C.).

LC/MS [method 3]: $R_t$=1.00 min; MS [ESIpos]: m/z=433 (M+H)$^+$.

(2R)-2-hydroxypropanimidamide hydrochloride, which is commercially available, was also synthesized from (2R)-2-hydroxypropanamide [R-(+)-lactamide] via the procedure described in WO 00/59510-A1 (Preparation 11, Step A) and WO 2013/138860-A1 (Intermediate to Precursor 82, p. 101-102).

Preparation Examples

Example compounds bearing a 1-hydroxyethyl substituent [R$^1$ in formula (I)=CH$_3$] which in the following are termed "diastereomer 1" and "diastereomer 2", respectively, represent pairs of separated diastereomers whose absolute configuration with regard to the 1-hydroxyethyl moiety (1R or 1S) had not been determined.

Diastereomeric excess (d.e.) values were determined in the usual way by analysis of HPLC peak areas according to the following formula:

$$d.e. = \left| \frac{\text{diastereomer 1(\% peak area)} - \text{diastereomer 2(\% peak area)}}{\text{diastereomer 1(\% peak area)} + \text{diastereomer 2(\% peak area)}} \right| \times 100\%.$$

Example 1

5-(4-Chlorophenyl)-2-{[1-(3-chlorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one

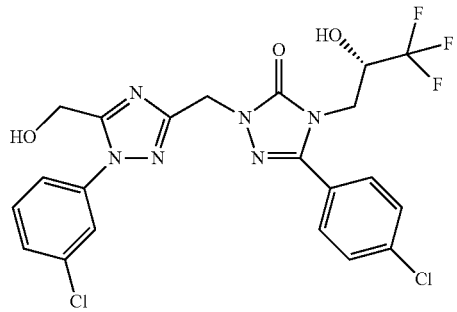

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (400 mg, 0.96 mmol) in pyridine (12 ml) were added (3-chlorophenyl)boronic acid (298.74 mg, 1.91 mmol) and copper(II) acetate (347 mg, 1.91 mmol). The reaction mixture was stirred at room temperature for 5 days, after which extra boronic acid (74.7 mg, 0.48 mmol, 0.5 eq.) was added due to incomplete conversion. After stirring for two additional days, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (113 mg, 0.21 mmol) was obtained (yield 22.4%).

LC/MS [method 2]: $R_t$=3.07 min; MS [ESIpos]: m/z=529 (M+H)$^+$ $^1$H NMR (400 MHz, DMSO-d$_6$): δ [ppm] 3.85 (dd, 1H), 4.01 (dd, 1H), 4.30 (br. s, 1H), 4.58 (s, 2H), 5.08 (s, 2H), 6.90 (br. d, 1H), 7.55-7.64 (m, 4H), 7.65-7.69 (m, 1H), 7.73-7.78 (m, 2H), 7.78-7.81 (m, 1H).

Example 2

5-(4-Chlorophenyl)-2-{[1-(3-fluorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one

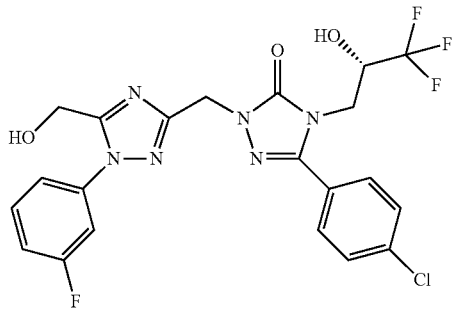 [SMILES: O=c1n(Cc2nc(CO)n(-c3cccc(Cl)c3)n2)nc(-c2ccc(Cl)cc2)n1C[C@H](O)C(F)(F)F]

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (100 mg, 0.24 mmol) in pyridine (3 ml) were added (3-fluorophenyl)boronic acid (66.83 mg, 0.48 mmol) and copper (II) acetate (86.75 mg, 0.48 mmol). The reaction mixture was stirred at room temperature for 5 days, after which extra boronic acid (16.72 mg, 0.12 mmol, 0.5 eq.) was added due to incomplete conversion. After stirring for two additional days, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (25 mg, 0.05 mmol) was obtained (yield 20.2%).

LC/MS [method 2]: $R_t$=2.87 min; MS [ESIpos]: m/z=513 (M+H)$^+$ $^1$H NMR (400 MHz, DMSO-d$_6$): δ [ppm] 3.85 (dd, 1H), 4.01 (dd, 1H), 4.30 (br. s, 1H), 4.59 (s, 2H), 5.08 (s, 2H), 6.90 (br. d, 1H), 7.37 (td, 1H), 7.51-7.66 (m, 5H), 7.72-7.79 (m, 2H).

Example 3

5-(4-Chlorophenyl)-2-{[5-(hydroxymethyl)-1-(2-methoxyphenyl)-1H-1,2,4-triazol-3-yl]methyl}-4-[(2S)-3,3,3-trifluoro-2-hydroxypropyl]-2,4-dihydro-3H-1,2,4-triazol-3-one

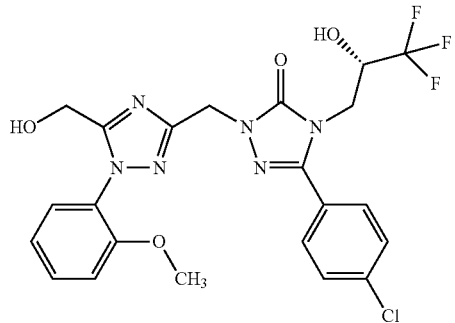 [SMILES: COc1ccccc1-n1nc(Cn2nc(-c3ccc(Cl)cc3)n(C[C@H](O)C(F)(F)F)c2=O)nc1CO]

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (300 mg, 0.72 mmol) in pyridine (9 ml) were added (2-methoxyphenyl)boronic acid (217.72 mg, 1.43 mmol) and copper(II) acetate (260.25 mg, 1.43 mmol). The reaction mixture was stirred at room temperature for 5 days, after which extra boronic acid (54.4 mg, 0.36 mmol, 0.5 eq.) was added due to incomplete conversion. After stirring for two additional days, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (73 mg, 0.14 mmol) was obtained (yield 22.4%, 98% purity).

LC/MS [method 3]: $R_t$=1.18 min; MS [ESIpos]: m/z=525 (M+H)$^+$ $^1$H NMR (400 MHz, DMSO-d$_6$): δ [ppm] 3.77 (s, 3H), 3.85 (dd, 1H), 4.01 (dd, 1H), 4.31 (br. s, 1H), 4.35 (s, 2H), 5.04 (s, 2H), 6.91 (br. s, 1H), 7.09 (t, 1H), 7.25 (d, 1H), 7.37 (dd, 1H), 7.52 (td, 1H), 7.63 (d, 2H), 7.76 (d, 2H).

Example 4

5-(4-Chlorophenyl)-2-{[1-(2-chlorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one

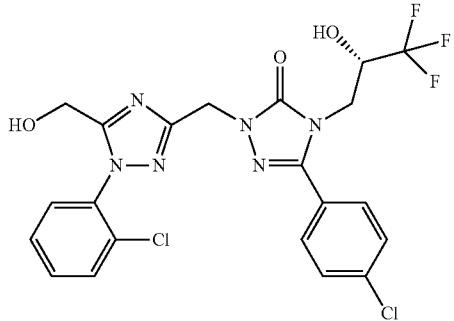 [SMILES: O=c1n(Cc2nc(CO)n(-c3ccccc3Cl)n2)nc(-c2ccc(Cl)cc2)n1C[C@H](O)C(F)(F)F]

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (3 g, 5.946 mmol, 83% purity) in pyridine (75 ml) were added (2-chlorophenyl)boronic acid (930 mg, 5.946 mmol) and copper(II) acetate (2.16 g, 11.89 mmol). The reaction mixture was stirred at room temperature overnight, after which extra boronic acid (500 mg, 3.20 mmol) was added due to incomplete conversion. The reaction mixture was further stirred at room temperature for 9 days. Over this time, three additional portions of boronic acid (1.5 g in total, 9.6 mmol) were added. After this, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (1.44 g, 2.72 mmol) was obtained (yield 45.7%).

LC/MS [method 2]: $R_t$=2.79 min; MS [ESIpos]: m/z=529 (M+H)$^+$ $^1$H NMR (400 MHz, DMSO-d$_6$): δ [ppm] 3.85 (dd, 1H), 4.01 (dd, 1H), 4.31 (br. s, 1H), 4.41 (s, 2H), 5.07 (s, 2H), 6.91 (d, 1H), 7.49-7.67 (m, 5H), 7.68-7.80 (m, 3H).

Example 5

5-(4-Chlorophenyl)-2-{[5-(hydroxymethyl)-1-(2-methylphenyl)-1H-1,2,4-triazol-3-yl]methyl}-4-[(2S)-3,3,3-trifluoro-2-hydroxypropyl]-2,4-dihydro-3H-1,2,4-triazol-3-one

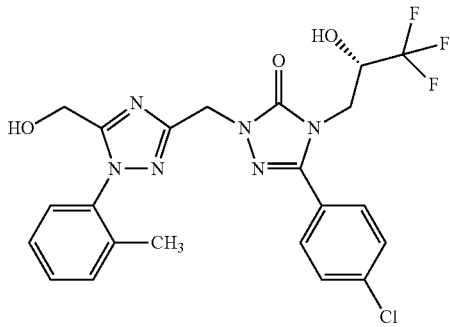 [SMILES: Cc1ccccc1-n1nc(Cn2nc(-c3ccc(Cl)cc3)n(C[C@H](O)C(F)(F)F)c2=O)nc1CO]

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (400 mg, 0.96 mmol) in pyridine (12 ml) were added (2-methylphenyl)boronic acid (259.7 mg, 1.91 mmol) and copper(II) acetate (347 mg, 1.91 mmol). The reaction mixture was stirred at room temperature for 5 days, after which extra boronic acid (64.9 mg, 0.48 mmol, 0.5 eq.) was added due to incomplete conversion. After stirring for two additional days, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (58 mg, 0.11 mmol) was obtained (yield 11.9%).

LC/MS [method 2]: $R_t$=2.85 min; MS [ESIpos]: m/z=509 (M+H)$^+$ $^1$H NMR (400 MHz, DMSO-d$_6$): δ [ppm] 2.01 (s, 3H), 3.85 (dd, 1H), 4.00 (dd, 1H), 4.30 (br. s, 1H), 4.34 (s, 2H), 5.07 (s, 2H), 6.90 (br. s, 1H), 7.32-7.50 (m, 4H), 7.62 (br. d, 2H), 7.75 (br. d, 2H).

Example 6

2-{[1-(3-Chloro-5-fluorophenyl)-5-(hydroxymethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

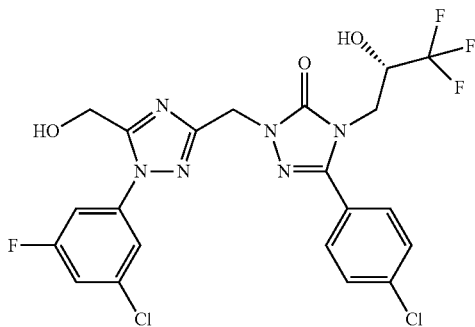 [SMILES: O=c1n(Cc2nc(CO)n(-c3cc(F)cc(Cl)c3)n2)nc(-c2ccc(Cl)cc2)n1C[C@H](O)C(F)(F)F]

To a solution of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one (400 mg, 0.96 mmol) in pyridine (12 ml) were added (3-chloro-5-fluorophenyl)boronic acid (333.1 mg, 1.91 mmol) and copper(II) acetate (347 mg, 1.91 mmol). The reaction mixture was stirred at room temperature for 5 days, after which extra boronic acid (83.2 mg, 0.48 mmol, 0.5 eq.) was added due to incomplete conversion. After stirring for two additional days, the reaction mixture was diluted with MTBE and then quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (91 mg, 0.17 mmol) was obtained (yield 17.4%).

LC/MS [method 3]: $R_t$=1.31 min; MS [ESIpos]: m/z=547 (M+H)$^+$ $^1$H NMR (400 MHz, DMSO-d$_6$): δ [ppm] 3.85 (dd, 1H), 4.01 (dd, 1H), 4.30 (br. s, 1H), 4.63 (s, 2H), 5.08 (s, 2H), 6.90 (br. s, 1H), 7.59-7.66 (m, 4H), 7.67-7.71 (m, 1H), 7.72-7.78 (m, 2H).

Example 7

5-(4-Chlorophenyl)-2-{[1-(3,5-difluorophenyl)-5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one

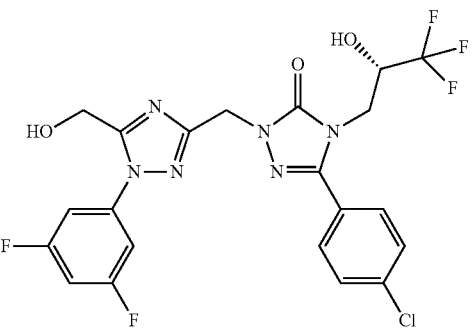 [SMILES: O=c1n(Cc2nc(CO)n(-c3cc(F)cc(F)c3)n2)nc(-c2ccc(Cl)cc2)n1C[C@H](O)C(F)(F)F]

The title compound was prepared analogously to Example 1 starting from 360 mg (0.86 mmol) of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one. 61 mg (0.11 mmol) of the desired compound were obtained (13.4% yield).

LC/MS [method 3]: $R_t$=1.25 min; MS [ESIpos]: m/z=531 (M+H)$^+$ $^1$H NMR (500 MHz, DMSO-d$_6$): δ [ppm] 3.86 (dd, 1H), 4.01 (dd, 1H), 4.25-4.38 (m, 1H), 4.64 (d, 2H), 5.08 (s, 2H), 5.94 (t, 1H), 6.92 (d, 1H), 7.46 (tt, 1H), 7.49-7.55 (m, 2H), 7.62 (br. d, 2H), 7.76 (br. d, 2H).

Example 8

5-(4-Chlorophenyl)-2-({5-(hydroxymethyl)-1-[2-(trifluoromethyl)phenyl]-1H-1,2,4-triazol-3-yl}-methyl)-4-[(2S)-3,3,3-trifluoro-2-hydroxypropyl]-2,4-dihydro-3H-1,2,4-triazol-3-one

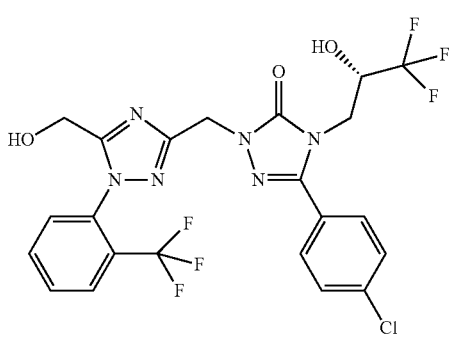 [SMILES: O=c1n(Cc2nc(CO)n(-c3ccccc3C(F)(F)F)n2)nc(-c2ccc(Cl)cc2)n1C[C@H](O)C(F)(F)F]

The title compound was prepared analogously to Example 1 starting from 500 mg (1.19 mmol) of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one. 104 mg (0.18 mmol) of the desired compound were obtained (15.5% yield).

LC/MS [method 3]: $R_t$=1.24 min; MS [ESIpos]: m/z=563 (M+H)$^+$ $^1$H NMR (400 MHz, DMSO-d$_6$): δ [ppm] 3.85 (dd, 1H), 4.00 (dd, 1H), 4.30 (br. s, 1H), 4.39 (s, 2H), 5.01-5.12 (m, 2H), 5.53 (br. s, 1H), 6.92 (d, 1H), 7.63 (d, 2H), 7.70 (d, 1H), 7.75 (d, 2H), 7.78-7.91 (m, 2H), 7.97 (d, 1H).

Example 9

2-{[1-(2-Chloro-5-fluorophenyl)-5-(hydroxymethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

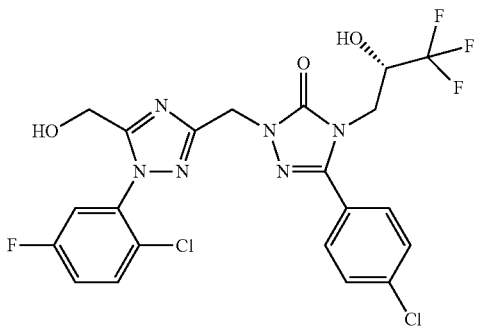 [SMILES: O=c1n(Cc2nc(CO)n(-c3cc(F)ccc3Cl)n2)nc(-c2ccc(Cl)cc2)n1C[C@H](O)C(F)(F)F]

The title compound was prepared analogously to Example 1 starting from 500 mg (1.19 mmol) of 5-(4-chlorophenyl)-2-{[5-(hydroxymethyl)-1H-1,2,4-triazol-3-yl]methyl}-4-[(2S)-3,3,3-trifluoro-2-hydroxypropyl]-2,4-dihydro-3H-1,2,4-triazol-3-one. 8.7 mg (0.02 mmol) of the desired compound were obtained (1.3% yield, 95% purity).

LC/MS [method 3]: $R_t$=1.23 min; MS [ESIpos]: m/z=547 (M+H)$^+$ $^1$H NMR (500 MHz, DMSO-d$_6$): δ [ppm] 3.86 (dd, 1H), 4.01 (dd, 1H), 4.30 (br. s, 1H), 4.46 (s, 2H), 5.03-5.11 (m, 2H), 6.92 (br. d, 1H), 7.53 (td, 1H), 7.61-7.65 (m, 2H), 7.68 (dd, 1H), 7.73-7.80 (m, 3H).

Example 10

5-(4-Chlorophenyl)-2-({5-[(1RS)-1-hydroxyethyl]-1-(2-methoxyphenyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

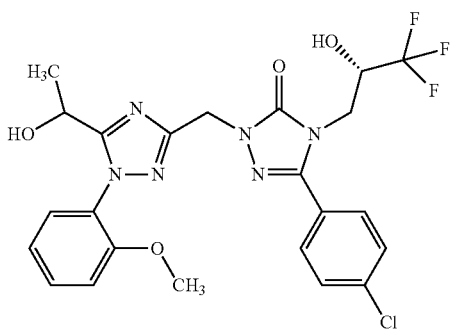

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (500 mg, 1.16 mmol) in pyridine (15 ml) were added (2-methoxyphenyl)boronic acid (351.1 mg, 2.31 mmol) and copper(II) acetate (419.7 mg, 2.31 mmol). The reaction mixture was stirred at room temperature for 5 days, after which extra boronic acid (87 mg, 0.58 mmol, 0.5 eq.) was added due to incomplete conversion. After stirring for two additional days, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (132 mg, 0.22 mmol) was obtained as a mixture of diastereomers (yield 19.1%, 90% purity).

LC/MS [method 2]: $R_t$=2.87 min; MS [ESIpos]: m/z=539 (M+H)$^+$ $^1$H NMR (400 MHz, DMSO-d$_6$): δ [ppm] 1.36 (d, 3H), 3.76 (s, 3H), 3.85 (dd, 1H), 4.00 (dd, 1H), 4.30 (br. s, 1H), 4.47-4.61 (m, 1H), 4.98-5.10 (m, 2H), 6.90 (br. s, 1H), 7.09 (td, 1H), 7.24 (dd, 1H), 7.35 (dd, 1H), 7.49-7.55 (m, 1H), 7.60-7.65 (m, 2H), 7.73-7.79 (m, 2H).

The two diastereomers were separated by preparative chiral HPLC [sample preparation: 128 mg dissolved in 10 ml methanol; injection volume: 0.3 ml; column: Daicel Chiralcel® OX-H 5 µm, 250×20 mm; eluent: isohexane/methanol 70:30; flow rate: 80 ml/min; temperature: 40° C.; UV detection: 210 nm]. After separation, 43.6 mg of diastereomer 1 (Example 11), which eluted first, and 45.1 mg of diastereomer 2 (Example 12), which eluted later, were isolated.

Example 11

5-(4-Chlorophenyl)-2-{[5-(1-hydroxyethyl)-1-(2-methoxyphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC (SFC): $R_t$=3.08 min, d.e.=100% [column: Daicel Chiralcel OX-3 250×4 mm; eluent: carbon dioxide/methanol (5%→60%); flow rate: 3 ml/min; UV detection: 220 nm].

$^1$H NMR (400 MHz, DMSO-$d_6$): δ [ppm] 1.36 (d, 3H), 3.76 (s, 3H), 3.85 (dd, 1H), 4.00 (dd, 1H), 4.30 (br. s, 1H), 4.52 (quin, 1H), 4.96-5.11 (m, 2H), 5.37 (d, 1H), 6.90 (d, 1H), 7.09 (td, 1H), 7.24 (d, 1H), 7.35 (dd, 1H), 7.52 (td, 1H), 7.60-7.65 (m, 2H), 7.73-7.79 (m, 2H).

Example 12

5-(4-Chlorophenyl)-2-{[5-(1-hydroxyethyl)-1-(2-methoxyphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC (SFC): $R_t$=3.38 min, d.e.=91.1% [column: Daicel Chiralcel® OX-3 250×4 mm; eluent: carbon dioxide/methanol (5%→60%); flow rate: 3 ml/min; UV detection: 220 nm].

$^1$H NMR (400 MHz, DMSO-$d_6$): δ [ppm] 1.36 (d, 3H), 3.76 (s, 3H), 3.84 (dd, 1H), 4.00 (dd, 1H), 4.31 (br. s, 1H), 4.52 (quin, 1H), 4.99-5.09 (m, 2H), 5.37 (d, 1H), 6.91 (d, 1H), 7.09 (td, 1H), 7.24 (d, 1H), 7.35 (dd, 1H), 7.52 (td, 1H), 7.60-7.65 (m, 2H), 7.74-7.79 (m, 2H).

Example 13

2-({1-(3-Chloro-5-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (diastereomeric mixture)

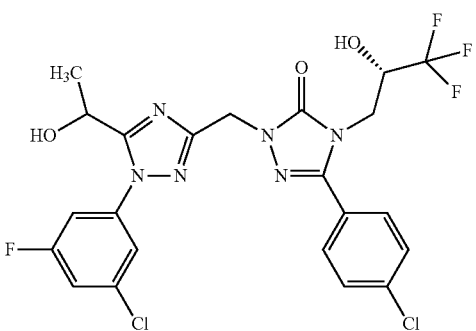

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (430 mg, 0.99 mmol) in pyridine (12.5 ml) were added (3-chloro-5-fluorophenyl)boronic acid (346.49 mg, 1.99 mmol) and copper(II) acetate (360.9 mg, 1.99 mmol). The reaction mixture was stirred at room temperature for 5 days, after which extra boronic acid (86.7 mg, 0.497 mmol, 0.5 eq.) was added due to incomplete conversion. After stirring for two additional days, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (148 mg, 0.26 mmol) was obtained as a mixture of diastereomers (yield 26.5%).

LC/MS [method 2]: $R_t$=3.28 min; MS [ESIpos]: m/z=561 (M+H)$^+$ $^1$H NMR (400 MHz, DMSO-$d_6$): δ [ppm] 1.48 (d, 3H), 3.85 (dd, 1H), 4.01 (dd, 1H), 4.29 (br. s, 1H), 4.83-4.91 (m, 1H), 5.01-5.13 (m, 2H), 6.89 (br. s, 1H), 7.55-7.70 (m, 5H), 7.72-7.78 (m, 2H).

The two diastereomers were separated by preparative chiral HPLC (SFC) [sample preparation: 143 mg dissolved in 15 ml methanol; injection volume: 0.5 ml; column: Daicel Chiralcel® OX-H 5 µm, 250×20 mm; eluent: carbon dioxide/methanol 80:20; flow rate: 80 ml/min; temperature: 40° C.; UV detection: 210 nm]. After separation, 70 mg of diastereomer 1 (Example 14), which eluted first, and 60 mg of diastereomer 2 (Example 15), which eluted later, were isolated.

Example 14

2-{[1-(3-Chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

Analytical chiral HPLC (SFC): $R_t$=4.45 min, d.e.=100% [column: Daicel Chiralcel OX-3 250×4 mm; eluent: carbon dioxide/methanol (5%→60%); flow rate: 3 ml/min; UV detection: 220 nm].

$^1$H NMR (400 MHz, DMSO-$d_6$): δ [ppm] 1.48 (d, 3H), 3.85 (dd, 1H), 4.01 (dd, 1H), 4.24-4.36 (m, 1H), 4.87 (quin, 1H), 5.07 (s, 2H), 5.83 (d, 1H), 6.89 (d, 1H), 7.58-7.69 (m, 5H), 7.71-7.79 (m, 2H).

Example 15

2-{[1-(3-Chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

Analytical chiral HPLC (SFC): $R_t$=4.80 min, d.e.=100% [column: Daicel Chiralcel OX-3 250×4 mm; eluent: carbon dioxide/methanol (5%→60%); flow rate: 3 ml/min; UV detection: 220 nm].

$^1$H NMR (400 MHz, DMSO-$d_6$): δ [ppm] 1.48 (d, 3H), 3.85 (dd, 1H), 4.01 (dd, 1H), 4.23-4.36 (m, 1H), 4.87 (quin, 1H), 5.02-5.12 (m, 2H), 5.83 (d, 1H), 6.89 (d, 1H), 7.57-7.70 (m, 5H), 7.71-7.79 (m, 2H).

Example 16

5-(4-Chlorophenyl)-2-({5-[(1RS)-1-hydroxyethyl]-1-phenyl-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

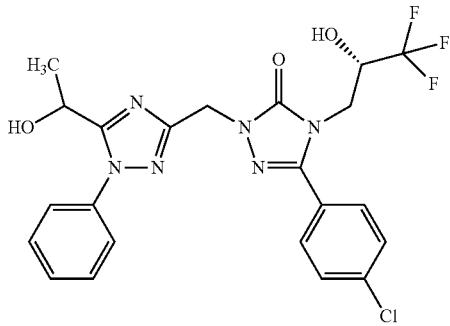 [SMILES: CC(O)c1nc(Cn2nc(-c3ccc(Cl)cc3)n(C[C@H](O)C(F)(F)F)c2=O)nn1-c1ccccc1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (250 mg, 0.462 mmol, 80% purity) in pyridine (6 ml) were added phenylboronic acid (112.69 mg, 0.92 mmol) and copper-(II) acetate (167.9 mg, 0.92 mmol). The reaction mixture was heated to 60° C. for 2 h and then stirred at room temperature for 4 days, after which extra boronic acid (28.2 mg, 0.23 mmol, 0.5 eq.) was added due to incomplete conversion. After further 4 h at 60° C. followed by stirring at room temperature for two additional days, the reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (42.5 mg, 0.08 mmol) was obtained as a mixture of diastereomers (yield 18.1%).

LC/MS [method 3]: $R_t$=1.21 min; MS [ESIpos]: m/z=509 (M+H)$^+$ $^1$H NMR (400 MHz, DMSO-d$_6$): δ [ppm] 1.45 (d, 3H), 3.85 (dd, 1H), 4.00 (dd, 1H), 4.30 (br. s, 1H), 4.77 (q, 1H), 4.99-5.13 (m, 2H), 6.90 (br. s, 1H), 7.47-7.66 (m, 7H), 7.72-7.79 (m, 2H).

The two diastereomers were separated by preparative chiral HPLC [sample preparation: 38.9 mg dissolved in 1 ml ethanol/isohexane (1:1); injection volume: 1 ml; column: Daicel Chiralcel® OX-H 5 μm, 250×20 mm; eluent: isohexane/ethanol 75:25; flow rate: 15 ml/min; temperature: 30° C.; UV detection: 220 nm]. After separation, 13 mg of diastereomer 1 (Example 17), which eluted first, and 14 mg of diastereomer 2 (Example 18), which eluted later, were isolated.

Example 17

5-(4-Chlorophenyl)-2-{[5-(1-hydroxyethyl)-1-phenyl-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=8.18 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-d$_6$): δ [ppm] 1.45 (d, 3H), 3.85 (dd, 1H), 4.00 (dd, 1H), 4.30 (br. s, 1H), 4.77 (quin, 1H), 4.98-5.14 (m, 2H), 5.68 (d, 1H), 6.89 (d, 1H), 7.48-7.65 (m, 7H), 7.72-7.80 (m, 2H).

Example 18

5-(4-Chlorophenyl)-2-{[5-(1-hydroxyethyl)-1-phenyl-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=11.40 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-d$_6$): δ [ppm] 1.45 (d, 3H), 3.85 (dd, 1H), 4.00 (dd, 1H), 4.30 (br. s, 1H), 4.77 (quin, 1H), 5.07 (s, 2H), 5.68 (d, 1H), 6.90 (d, 1H), 7.47-7.65 (m, 7H), 7.72-7.79 (m, 2H).

Example 19

5-(4-Chlorophenyl)-2-({1-[3-(difluoromethyl)phenyl]-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

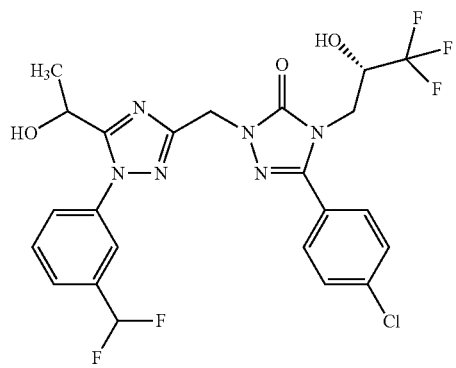 [SMILES: CC(O)c1nc(Cn2nc(-c3ccc(Cl)cc3)n(C[C@H](O)C(F)(F)F)c2=O)nn1-c1cccc(C(F)F)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.74 mmol, 80% purity) in pyridine (9.6 ml) were added [3-(difluoromethyl)phenyl]boronic acid (254.26 mg, 1.48 mmol) and copper(II) acetate (268.6 mg, 1.48 mmol). The reaction mixture was heated to 60° C. for 2 h and then stirred at room temperature for 5 days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (47 mg, 0.08 mmol) was obtained as a mixture of diastereomers (yield 11.3%).

LC/MS [method 1]: $R_t$=1.04 min; MS [ESIpos]: m/z=559 (M+H)$^+$ $^1$H NMR (400 MHz, DMSO-d$_6$): δ [ppm] 1.47 (d, 3H), 3.85 (dd, 1H), 4.01 (dd, 1H), 4.24-4.36 (m, 1H), 4.81 (q, 1H), 5.02-5.13 (m, 2H), 5.74 (br. s, 1H), 6.89 (br. s, 1H), 7.14 (t, 1H), 7.59-7.65 (m, 2H), 7.69-7.78 (m, 4H), 7.81-7.87 (m, 2H).

The two diastereomers were separated by preparative chiral HPLC [sample preparation: 45 mg dissolved in 1 ml ethanol/isohexane (1:1); injection volume: 1 ml; column: Daicel Chiralcel® OX-H 5 μm, 250×20 mm; eluent: isohexane/ethanol 75:25; flow rate: 15 ml/min; temperature: 30° C.; UV detection: 220 nm]. After separation, 20 mg of diastereomer 1 (Example 20), which eluted first, and 20 mg of diastereomer 2 (Example 21), which eluted later, were isolated.

Example 20

5-(4-Chlorophenyl)-2-({1-[3-(difluoromethyl)phenyl]-5-(1-hydroxyethyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomer 1)

Analytical chiral HPLC: $R_t$=6.72 min, d.e.=99% [column: LUX Cellulose-4, 5 μm, 250×4.6 mm; eluent: isohexane/ethanol 70:30; flow rate: 1 ml/min; temperature: 40° C.; UV detection: 220 nm].
$^1$H NMR (400 MHz, DMSO-$d_6$): δ [ppm] 1.47 (d, 3H), 3.85 (dd, 1H), 4.01 (dd, 1H), 4.23-4.36 (m, 1H), 4.81 (quin, 1H), 5.02-5.14 (m, 2H), 5.74 (d, 1H), 6.88 (d, 1H), 7.14 (t, 1H), 7.59-7.64 (m, 2H), 7.69-7.79 (m, 4H), 7.80-7.87 (m, 2H).

Example 21

5-(4-Chlorophenyl)-2-({1-[3-(difluoromethyl)phenyl]-5-(1-hydroxyethyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomer 2)

Analytical chiral HPLC: $R_t$=9.36 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].
$^1$H NMR (400 MHz, DMSO-$d_6$): δ [ppm] 1.47 (d, 3H), 3.85 (dd, 1H), 4.01 (dd, 1H), 4.24-4.37 (m, 1H), 4.81 (quin, 1H), 5.08 (s, 2H), 5.74 (d, 1H), 6.89 (d, 1H), 7.13 (t, 1H), 7.58-7.66 (m, 2H), 7.69-7.79 (m, 4H), 7.81-7.87 (m, 2H).

Example 22

5-(4-Chlorophenyl)-2-({5-[(1RS)-1-hydroxyethyl]-1-[3-(trifluoromethyl)phenyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

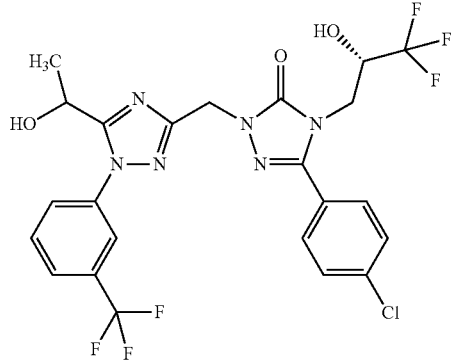 [SMILES: CC(O)c1nc(Cn2nc(-c3ccc(Cl)cc3)n(C[C@H](O)C(F)(F)F)c2=O)nn1-c1cccc(C(F)(F)F)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.74 mmol, 80% purity) in pyridine (9.6 ml) were added [3-(trifluoromethyl)phenyl]boronic acid (280.86 mg, 1.48 mmol) and copper(II) acetate (268.6 mg, 1.48 mmol). The reaction mixture was heated to 60° C. for 2 h and then stirred at room temperature for 5 days, after which extra boronic acid (70.2 mg, 0.37 mmol, 0.5 eq.) was added due to incomplete conversion. After further 4 h at 60° C. followed by stirring at room temperature overnight, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (58.2 mg, 0.10 mmol) was obtained as a mixture of diastereomers (yield 13.6%).
LC/MS [method 1]: $R_t$=1.06 min; MS [ESIpos]: m/z=577 (M+H)$^+$
$^1$H NMR (400 MHz, DMSO-$d_6$): δ [ppm] 1.48 (d, 3H), 3.85 (dd, 1H), 4.01 (dd, 1H), 4.30 (br. s, 1H), 4.83 (q, 1H), 5.02-5.15 (m, 2H), 5.79 (br. s, 1H), 6.85-6.94 (m, 1H), 7.58-7.66 (m, 2H), 7.71-7.85 (m, 3H), 7.86-7.92 (m, 1H), 7.94-8.01 (m, 1H), 8.04 (s, 1H).

The two diastereomers were separated by preparative chiral HPLC [sample preparation: 58 mg dissolved in 2 ml ethanol/isohexane (1:1); injection volume: 1 ml; column: Daicel Chiralcel® OX-H 5 μm, 250×20 mm; eluent: isohexane/ethanol 75:25; flow rate: 15 ml/min; temperature: 30° C.; UV detection: 220 nm]. After separation, 19.5 mg of diastereomer 1 (Example 23), which eluted first, and 19.2 mg of diastereomer 2 (Example 24), which eluted later, were isolated.

Example 23

5-(4-Chlorophenyl)-2-({5-(1-hydroxyethyl)-1-[3-(trifluoromethyl)phenyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomer 1)

Analytical chiral HPLC: $R_t$=4.94 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].
$^1$H NMR (400 MHz, DMSO-$d_6$): δ [ppm] 1.48 (d, 3H), 3.85 (dd, 1H), 4.01 (dd, 1H), 4.30 (br. s, 1H), 4.83 (q, 1H), 5.03-5.13 (m, 2H), 5.79 (br. s, 1H), 6.88 (d, 1H), 7.59-7.65 (m, 2H), 7.72-7.85 (m, 3H), 7.86-7.92 (m, 1H), 7.95-8.01 (m, 1H), 8.04 (br. s, 1H).

Example 24

5-(4-Chlorophenyl)-2-({5-(1-hydroxyethyl)-1-[3-(trifluoromethyl)phenyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomer 2)

Analytical chiral HPLC: $R_t$=6.13 min, d.e.=98.6% [column: LUX Cellulose-4, 5 μm, 250×4.6 mm; eluent: isohexane/ethanol 70:30; flow rate: 1 ml/min; temperature: 40° C.; UV detection: 220 nm].
$^1$H NMR (400 MHz, DMSO-$d_6$): δ [ppm] 1.48 (d, 3H), 3.85 (dd, 1H), 4.01 (dd, 1H), 4.24-4.36 (m, 1H), 4.83 (quin, 1H), 5.09 (s, 2H), 5.78 (d, 1H), 6.89 (d, 1H), 7.62 (d, 2H), 7.71-7.77 (m, 2H), 7.78-7.85 (m, 1H), 7.86-7.92 (m, 1H), 7.94-8.01 (m, 1H), 8.04 (br. s, 1H).

Example 25

5-(4-Chlorophenyl)-2-({1-(3,5-difluorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

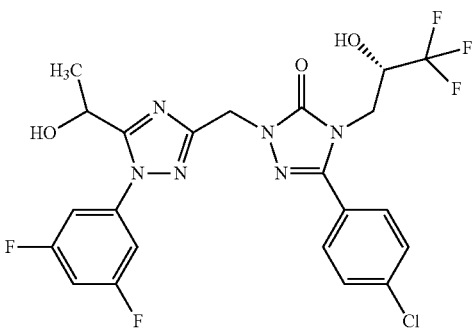 [SMILES: CC(O)c1nc(Cn2nc(-c3ccc(Cl)cc3)n(C[C@H](O)C(F)(F)F)c2=O)nn1-c1cc(F)cc(F)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (3,5-difluorophenyl)boronic acid (291.9 mg, 1.85 mmol) and copper(II) acetate (335.7 mg, 1.85 mmol). The reaction mixture was heated to 60° C. for 2 h and then stirred at room temperature for 4 days, after which extra boronic acid (72.98 mg, 0.46 mmol, 0.5 eq.) was added due to incomplete conversion. After further 2 h at 60° C. followed by stirring at room temperature for three additional days, the reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (114.3 mg, 0.21 mmol) was obtained as a mixture of diastereomers (yield 22.7%).

LC/MS [method 3]: $R_t$=1.28 min; MS [ESIpos]: m/z=545 (M+H)$^+$ $^1$H NMR (400 MHz, DMSO-$d_6$): δ [ppm] 1.49 (d, 3H), 3.85 (dd, 1H), 4.01 (dd, 1H), 4.30 (br. s, 1H), 4.88 (q, 1H), 5.02-5.13 (m, 2H), 6.89 (br. s, 1H), 7.41-7.54 (m, 3H), 7.62 (d, 2H), 7.75 (d, 2H).

The two diastereomers were separated by preparative chiral HPLC [sample preparation: 110 mg dissolved in 7 ml ethanol/isohexane (1:1); injection volume: 0.6 ml; column: Daicel Chiralcel® OX-H 5 μm, 250×20 mm; eluent: isohexane/ethanol 70:30; flow rate: 20 ml/min; temperature: 40° C.; UV detection: 220 nm]. After separation, 42 mg of diastereomer 1 (Example 26), which eluted first, and 44 mg of diastereomer 2 (Example 27), which eluted later, were isolated.

Example 26

5-(4-Chlorophenyl)-2-{[1-(3,5-difluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 2]: $R_t$=3.10 min; MS [ESIpos]: m/z=545 (M+H)$^+$

Analytical chiral HPLC: $R_t$=1.09 min, d.e.=100% [column: Daicel Chiralpack OX-3 3 μm, 50×4.6 mm; eluent: isohexane/ethanol 70:30; flow rate: 1 ml/min; UV detection: 220 nm].

$^1$H NMR (400 MHz, DMSO-$d_6$): δ [ppm] 1.49 (d, 3H), 3.85 (dd, 1H), 4.01 (dd, 1H), 4.23-4.36 (m, 1H), 4.88 (quin, 1H), 5.02-5.13 (m, 2H), 5.84 (d, 1H), 6.89 (d, 1H), 7.41-7.54 (m, 3H), 7.59-7.65 (m, 2H), 7.73-7.76 (m, 2H).

Example 27

5-(4-Chlorophenyl)-2-{[1-(3,5-difluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 2]: $R_t$=3.09 min; MS [ESIpos]: m/z=545 (M+H)$^+$

Analytical chiral HPLC: $R_t$=1.28 min, d.e.=99% [column: Daicel Chiralpack OX-3 3 μm, 50×4.6 mm; eluent: isohexane/ethanol 70:30; flow rate: 1 ml/min; UV detection: 220 nm].

$^1$H NMR (400 MHz, DMSO-$d_6$): δ [ppm] 1.48 (d, 3H), 3.85 (dd, 1H), 4.01 (dd, 1H), 4.24-4.36 (m, 1H), 4.88 (quin, 1H), 5.07 (s, 2H), 5.83 (d, 1H), 6.90 (d, 1H), 7.42-7.54 (m, 3H), 7.59-7.65 (m, 2H), 7.72-7.79 (m, 2H).

Example 28

5-(4-Chlorophenyl)-2-({5-[(1RS)-1-hydroxyethyl]-1-(3-methylphenyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

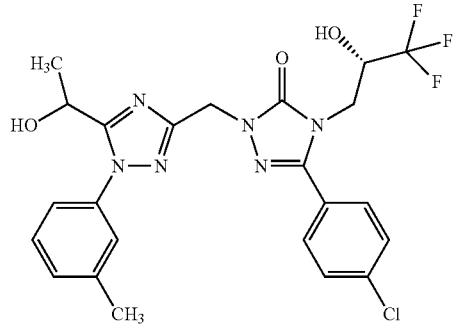 [SMILES: Cc1cccc(-n2nc(Cn3nc(-c4ccc(Cl)cc4)n(C[C@H](O)C(F)(F)F)c3=O)nc2C(C)O)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (3-methylphenyl)boronic acid (251.32 mg, 1.85 mmol) and copper(II) acetate (335.7 mg, 1.85 mmol). The reaction mixture was heated to 60° C. for 2 h and then stirred at room temperature for three days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (59.6 mg, 0.11 mmol) was obtained as a mixture of diastereomers (yield 12.3%).

$^1$H NMR (400 MHz, DMSO-$d_6$): δ [ppm] 1.44 (d, 3H), 2.38 (s, 3H), 3.85 (dd, 1H), 4.00 (dd, 1H), 4.29 (br. s, 1H), 4.76 (q, 1H), 5.01-5.11 (m, 2H), 5.66 (br. s, 1H), 6.90 (t, 1H), 7.29-7.35 (m, 1H), 7.38-7.47 (m, 3H), 7.59-7.65 (m, 2H), 7.72-7.78 (m, 2H).

The two diastereomers were separated by preparative chiral HPLC [sample preparation: 56 mg dissolved in 2 ml ethanol/isohexane (1:1); injection volume: 0.5 ml; column: Daicel Chiralcel® OX-H 5 μm, 250×20 mm; eluent: isohexane/ethanol 70:30; flow rate: 15 ml/min; temperature: 25° C.; UV detection: 220 nm]. After separation, 22 mg of diastereomer 1 (Example 29), which eluted first, and 24 mg of diastereomer 2 (Example 30), which eluted later, were isolated.

Example 29

5-(4-Chlorophenyl)-2-{[5-(1-hydroxyethyl)-1-(3-methylphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=7.97 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.44 (d, 3H), 2.38 (s, 3H), 3.85 (dd, 1H), 4.01 (dd, 1H), 4.24-4.36 (m, 1H), 4.76 (quin, 1H), 5.00-5.11 (m, 2H), 5.67 (d, 1H), 6.89 (d, 1H), 7.30-7.35 (m, 1H), 7.38-7.47 (m, 3H), 7.59-7.65 (m, 2H), 7.72-7.78 (m, 2H).

Example 30

5-(4-Chlorophenyl)-2-{[5-(1-hydroxyethyl)-1-(3-methylphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=11.44 min, d.e.=99.1% [column: LUX Cellulose-4, 5 rim, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.44 (d, 3H), 2.38 (s, 3H), 3.85 (dd, 1H), 4.00 (dd, 1H), 4.24-4.36 (m, 1H), 4.77 (quin, 1H), 5.01-5.10 (m, 2H), 5.67 (d, 1H), 6.90 (d, 1H), 7.29-7.35 (m, 1H), 7.38-7.47 (m, 3H), 7.59-7.65 (m, 2H), 7.73-7.78 (m, 2H).

Example 31

5-(4-Chlorophenyl)-2-({1-(2-ethylphenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

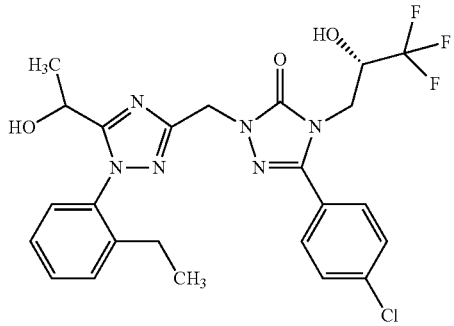 [SMILES: CCc1ccccc1-n1nc(Cn2nc(-c3ccc(Cl)cc3)n(C[C@H](O)C(F)(F)F)c2=O)nc1C(C)O]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (600 mg, 1.39 mmol) in pyridine (18 ml) were added (2-ethylphenyl)boronic acid (415.87 mg, 2.77 mmol) and copper(II) acetate (503.6 mg, 2.77 mmol). The reaction mixture was heated to 60° C. for 2 h and then stirred at room temperature for three days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (69.4 mg, 0.13 mmol) was obtained as a mixture of diastereomers (yield 9.1%).

LC/MS [method 2]: $R_t$=3.16 min; MS [ESIpos]: m/z=537 (M+H)$^+$ $^1$H NMR (400 MHz, DMSO-$d_6$): δ [ppm] 0.98 (t, 3H), 1.37 (d, 3H), 2.27 (qd, 2H), 3.84 (dd, 1H), 4.00 (dd, 1H), 4.21-4.37 (m, 1H), 4.52 (q, 1H), 5.00-5.13 (m, 2H), 5.48 (br. s, 1H), 6.90 (dd, 1H), 7.32-7.40 (m, 2H), 7.41-7.54 (m, 2H), 7.58-7.65 (m, 2H), 7.70-7.77 (m, 2H).

The two diastereomers were separated by preparative chiral HPLC [sample preparation: 65 mg dissolved in 4 ml ethanol/isohexane (1:1); injection volume: 0.5 ml; column: Daicel Chiralcel® OX-H 5 μm, 250×20 mm; eluent: isohexane/ethanol 50:50; flow rate: 20 ml/min; temperature: 40° C.; UV detection: 220 nm]. After separation, 25 mg of diastereomer 1 (Example 32), which eluted first, and 25 mg of diastereomer 2 (Example 33), which eluted later, were isolated.

Example 32

5-(4-Chlorophenyl)-2-{[1-(2-ethylphenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 2]: $R_t$=3.15 min; MS [ESIpos]: m/z=537 (M+H)$^+$

Analytical chiral HPLC: $R_t$=0.96 min, d.e.=100% [column: Daicel Chiralpack OX-3 3 μm, 50×4.6 mm; eluent: isohexane/ethanol 50:50; flow rate: 1 ml/min; UV detection: 220 nm].

¹H NMR (400 MHz, DMSO-d₆): δ [ppm] 0.98 (t, 3H), 1.37 (d, 3H), 2.27 (qd, 2H), 3.84 (dd, 1H), 4.00 (dd, 1H), 4.23-4.35 (m, 1H), 4.52 (quin, 1H), 5.00-5.12 (m, 2H), 5.48 (d, 1H), 6.89 (d, 1H), 7.32-7.40 (m, 2H), 7.42-7.53 (m, 2H), 7.59-7.66 (m, 2H), 7.71-7.78 (m, 2H).

Example 33

5-(4-Chlorophenyl)-2-{[1-(2-ethylphenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 2]: $R_t$=3.15 min; MS [ESIpos]: m/z=537 (M+H)⁺

Analytical chiral HPLC: $R_t$=1.09 min, d.e.=100% [column: Daicel Chiralpack OX-3 3 μm, 50×4.6 mm; eluent: isohexane/ethanol 50:50; flow rate: 1 ml/min; UV detection: 220 nm].

¹H NMR (400 MHz, DMSO-d₆): δ [ppm] 0.98 (t, 3H), 1.37 (d, 3H), 2.27 (qd, 2H), 3.84 (dd, 1H), 4.00 (dd, 1H), 4.23-4.36 (m, 1H), 4.52 (quin, 1H), 5.07 (s, 2H), 5.48 (d, 1H), 6.90 (d, 1H), 7.32-7.40 (m, 2H), 7.42-7.54 (m, 2H), 7.59-7.66 (m, 2H), 7.71-7.78 (m, 2H).

Example 34

2-({1-(2-Chloro-4-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (diastereomeric mixture)

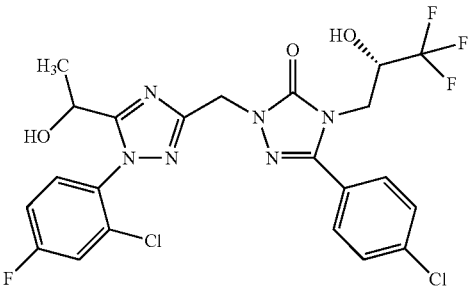 [SMILES: CC(O)c1nc(Cn2nc(-c3ccc(Cl)cc3)n(C[C@H](O)C(F)(F)F)c2=O)nn1-c1ccc(F)cc1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (600 mg, 1.39 mmol) in pyridine (18 ml) were added (2-chloro-4-fluorophenyl)boronic acid (483 mg, 2.77 mmol) and copper(II) acetate (503.6 mg, 2.77 mmol). The reaction mixture was heated to 60° C. for 2 h and then stirred at room temperature for 5 days, after which extra boronic acid (242 mg, 1.39 mmol) was added due to incomplete conversion. The reaction mixture was further stirred at room temperature for 4 days. Over this time, two additional portions of boronic acid (483 mg in total, 2.77 mmol) were added. After this, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (107 mg, 0.19 mmol) was obtained as a mixture of diastereomers (yield 13.7%).

LC/MS [method 2]: $R_t$=3.02 min; MS [ESIpos]: m/z=561 (M+H)⁺

¹H NMR (400 MHz, DMSO-d₆): δ [ppm] 1.38 (d, 3H), 3.85 (dd, 1H), 4.00 (dd, 1H), 4.23-4.36 (m, 1H), 4.57-4.67 (m, 1H), 5.00-5.12 (m, 2H), 6.90 (br. s, 1H), 7.42 (td, 1H), 7.57-7.79 (m, 6H).

The two diastereomers were separated by preparative chiral HPLC [sample preparation: 104 mg dissolved in 5 ml ethanol/isohexane (1:1); injection volume: 0.5 ml; column: Daicel Chiralcel® OX-H 5 μm, 250×20 mm; eluent: isohexane/ethanol 70:30; flow rate: 20 ml/min; temperature: 40° C.; UV detection: 220 nm]. After separation, 56 mg of diastereomer 1 (Example 35), which eluted first, and 29 mg of diastereomer 2 (Example 36), which eluted later, were isolated.

Example 35

2-{[1-(2-Chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

Analytical chiral HPLC: $R_t$=1.36 min, d.e.=100% [column: Daicel Chiralpack OX-3 3 μm, 50×4.6 mm; eluent: isohexane/ethanol 70:30; flow rate: 1 ml/min; UV detection: 220 nm].

¹H NMR (400 MHz, DMSO-d₆): δ [ppm] 1.38 (d, 3H), 3.85 (dd, 1H), 4.00 (dd, 1H), 4.23-4.36 (m, 1H), 4.61 (quin, 1H), 5.01-5.11 (m, 2H), 5.51 (d, 1H), 6.89 (d, 1H), 7.42 (td, 1H), 7.60-7.65 (m, 2H), 7.66-7.72 (m, 1H), 7.72-7.78 (m, 3H).

Example 36

2-{[1-(2-Chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

Analytical chiral HPLC: $R_t$=1.72 min, d.e.=100% [column: Daicel Chiralpack OX-3 3 μm, 50×4.6 mm; eluent: isohexane/ethanol 70:30; flow rate: 1 ml/min; UV detection: 220 nm].

¹H NMR (400 MHz, DMSO-d₆): δ [ppm] 1.38 (d, 3H), 3.85 (dd, 1H), 4.00 (dd, 1H), 4.23-4.37 (m, 1H), 4.61 (quin, 1H), 5.06 (s, 2H), 5.51 (d, 1H), 6.90 (d, 1H), 7.42 (td, 1H), 7.60-7.65 (m, 2H), 7.66-7.72 (m, 1H), 7.72-7.78 (m, 3H).

Example 37

5-(4-Chlorophenyl)-2-({1-(5-fluoro-2-methoxyphenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

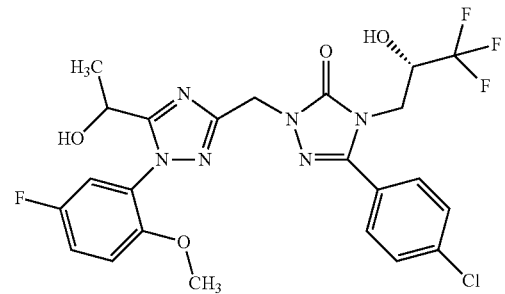 [SMILES: COc1ccc(F)cc1-n1nc(Cn2nc(-c3ccc(Cl)cc3)n(C[C@H](O)C(F)(F)F)c2=O)nc1C(C)O]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (600 mg, 1.39 mmol) in pyridine (18 ml) were added (5-fluoro-2-methoxyphenyl)boronic acid (471.22 mg, 2.77 mmol) and copper(II) acetate (503.6 mg, 2.77 mmol). The reaction mixture was heated to 60° C. for 2 h and then stirred at room temperature for three days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (62.2 mg, 0.11 mmol) was obtained as a mixture of diastereomers (yield 8.1%).

LC/MS [method 2]: $R_t$=2.93 min; MS [ESIpos]: m/z=557 (M+H)$^+$ $^1$H NMR (400 MHz, DMSO-d$_6$): δ [ppm] 1.37 (d, 3H), 3.75 (s, 3H), 3.80-3.89 (m, 1H), 4.00 (dd, 1H), 4.24-4.36 (m, 1H), 4.52-4.62 (m, 1H), 4.99-5.04 (m, 2H), 6.90 (t, 1H), 7.26 (dd, 1H), 7.33 (dd, 1H), 7.37-7.44 (m, 1H), 7.60-7.65 (m, 2H), 7.73-7.78 (m, 2H).

The two diastereomers were separated by preparative chiral HPLC [sample preparation: 55.4 mg dissolved in 6 ml ethanol/isohexane (1:1); injection volume: 2 ml; column: Daicel Chiralcel® OX-H 5 μm, 250×20 mm; eluent: isohexane/ethanol 80:20; flow rate: 20 ml/min; temperature: 40° C.; UV detection: 220 nm]. After separation, 23 mg of diastereomer 1 (Example 38), which eluted first, and 21 mg of diastereomer 2 (Example 39), which eluted later, were isolated.

Example 38

5-(4-Chlorophenyl)-2-{[1-(5-fluoro-2-methoxyphenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 2]: $R_t$=2.91 min; MS [ESIpos]: m/z=557 (M+H)$^+$

Analytical chiral HPLC: $R_t$=2.13 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 1.37 (d, 3H), 3.75 (s, 3H), 3.81-3.89 (m, 1H), 4.00 (dd, 1H), 4.25-4.35 (m, 1H), 4.53-4.62 (m, 1H), 4.99-5.10 (m, 2H), 5.40 (d, 1H), 6.89 (d, 1H), 7.26 (dd, 1H), 7.33 (dd, 1H), 7.41 (td, 1H), 7.60-7.66 (m, 2H), 7.73-7.79 (m, 2H).

Example 39

5-(4-Chlorophenyl)-2-{[1-(5-fluoro-2-methoxyphenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 2]: $R_t$=2.90 min; MS [ESIpos]: m/z=557 (M+H)$^+$

Analytical chiral HPLC: $R_t$=2.75 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 1.37 (d, 3H), 3.75 (s, 3H), 3.85 (dd, 1H), 4.00 (dd, 1H), 4.24-4.36 (m, 1H), 4.57 (quin, 1H), 4.99-5.10 (m, 2H), 5.40 (d, 1H), 6.91 (d, 1H), 7.26 (dd, 1H), 7.33 (dd, 1H), 7.41 (td, 1H), 7.60-7.65 (m, 2H), 7.73-7.78 (m, 2H).

Example 40

5-(4-Chlorophenyl)-2-({1-(2-fluorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

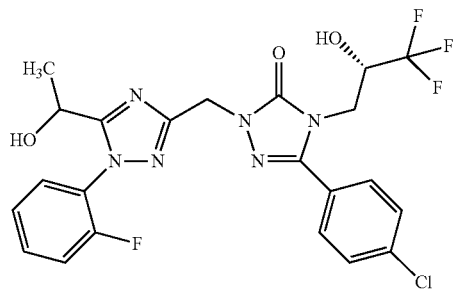 [SMILES: CC(O)c1nc(Cn2nc(-c3ccc(Cl)cc3)n(C[C@H](O)C(F)(F)F)c2=O)nn1-c1ccccc1F]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (600 mg, 1.39 mmol) in pyridine (18 ml) were added (2-fluorophenyl)boronic acid (387.96 mg, 2.77 mmol) and copper(II) acetate (503.6 mg, 2.77 mmol). The reaction mixture was heated to 60° C. for 2 h and then stirred at room temperature for 3 days. Over this time, two additional portions of boronic acid (387.96 mg in total, 2.77 mmol) were added. After this, the resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (30.1 mg, 0.06 mmol) was obtained as a mixture of diastereomers (yield 4.1%).

LC/MS [method 2]: $R_t$=2.84 min; MS [ESIpos]: m/z=527 (M+H)$^+$ $^1$H NMR (400 MHz, DMSO-d$_6$): δ [ppm] 1.40 (d, 3H), 3.85 (dd, 1H), 4.00 (dd, 1H), 4.29 (br. s, 1H), 4.69 (q, 1H), 5.01-5.12 (m, 2H), 6.89 (br. s, 1H), 7.38 (t, 1H), 7.48 (t, 1H), 7.57-7.66 (m, 4H), 7.71-7.80 (m, 2H).

The two diastereomers were separated by preparative chiral HPLC [sample preparation: 26 mg dissolved in 4 ml ethanol/isohexane (1:1); injection volume: 2 ml; column: Daicel Chiralcel® OX-H 5 μm, 250×20 mm; eluent: isohexane/ethanol 80:20; flow rate: 25 ml/min; temperature: 40° C.; UV detection: 220 nm]. After separation, 11 mg of diastereomer 1 (Example 41), which eluted first, and 9 mg of diastereomer 2 (Example 42), which eluted later, were isolated.

Example 41

5-(4-Chlorophenyl)-2-{[1-(2-fluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 2]: $R_t$=2.83 min; MS [ESIpos]: m/z=527 (M+H)$^+$

Analytical chiral HPLC: $R_t$=2.32 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

¹H NMR (400 MHz, DMSO-d₆): δ [ppm] 1.40 (d, 3H), 3.85 (dd, 1H), 4.00 (dd, 1H), 4.24-4.36 (m, 1H), 4.69 (quin, 1H), 5.01-5.12 (m, 2H), 5.53 (d, 1H), 6.89 (d, 1H), 7.38 (t, 1H), 7.48 (t, 1H), 7.57-7.66 (m, 4H), 7.72-7.78 (m, 2H).

Example 42

5-(4-Chlorophenyl)-2-{[1-(2-fluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 2]: R$_t$=2.82 min; MS [ESIpos]: m/z=527 (M+H)⁺

Analytical chiral HPLC: R$_t$=3.23 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

¹H NMR (400 MHz, DMSO-d₆): δ [ppm] 1.40 (d, 3H), 3.84 (dd, 1H), 4.00 (dd, 1H), 4.24-4.35 (m, 1H), 4.69 (quin, 1H), 5.07 (s, 2H), 5.53 (d, 1H), 6.90 (d, 1H), 7.38 (t, 1H), 7.48 (t, 1H), 7.57-7.67 (m, 4H), 7.72-7.79 (m, 2H).

Example 43

2-({1-(3-Chloro-4-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (diastereomeric mixture)

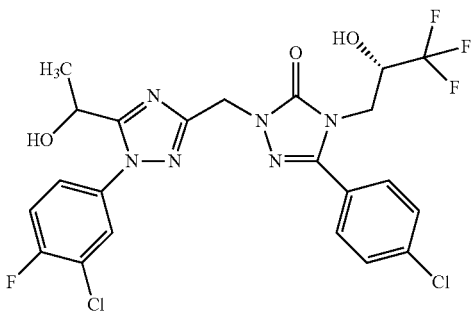 [SMILES: CC(O)c1nc(Cn2nc(-c3ccc(Cl)cc3)n(C[C@H](O)C(F)(F)F)c2=O)nn1-c1ccc(F)c(Cl)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (3-chloro-4-fluorophenyl)boronic acid (322.6 mg, 1.85 mmol) and copper(II) acetate (335.7 mg, 1.85 mmol). The reaction mixture was heated to 60° C. for 2 h and then stirred at room temperature for 6 days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (99.1 mg, 0.18 mmol) was obtained as a mixture of diastereomers (yield 19.1%).

LC/MS [method 3]: R$_t$=1.31 min; MS [ESIpos]: m/z=561 (M+H)⁺

¹H NMR (400 MHz, DMSO-d₆): δ [ppm] 1.46 (d, 3H), 3.85 (dd, 1H), 4.01 (dd, 1H), 4.30 (br. s, 1H), 4.80 (q, 1H), 5.01-5.13 (m, 2H), 6.90 (br. s, 1H), 7.59-7.70 (m, 4H), 7.72-7.78 (m, 2H), 7.93 (dd, 1H).

The two diastereomers were separated by preparative chiral HPLC [sample preparation: 97.1 mg dissolved in 3 ml ethanol; injection volume: 0.3 ml; column: Daicel Chiralcel® OX-H 5 μm, 250×20 mm; eluent: isohexane/ethanol 80:20; flow rate: 15 ml/min; temperature: 25° C.; UV detection: 220 nm]. After separation, 40 mg of diastereomer 1 (Example 44), which eluted first, and 42 mg of diastereomer 2 (Example 45), which eluted later, were isolated.

Example 44

2-{[1-(3-Chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

LC/MS [method 2]: R$_t$=3.22 min; MS [ESIpos]: m/z=561 (M+H)⁺

Preparative chiral HPLC: R$_t$=9.97 min, d.e.=100% [column: Daicel Chiralcel OX-H 5 μm, 250×20 mm; eluent: isohexane/ethanol 80:20; flow rate: 15 ml/min; temperature: 25° C.; UV detection: 220 nm].

¹H NMR (400 MHz, DMSO-d₆): δ [ppm] 1.46 (d, 3H), 3.85 (dd, 1H), 4.01 (dd, 1H), 4.22-4.36 (m, 1H), 4.80 (quin, 1H), 5.01-5.12 (m, 2H), 5.75 (d, 1H), 6.89 (d, 1H), 7.58-7.70 (m, 4H), 7.71-7.78 (m, 2H), 7.93 (dd, 1H).

Example 45

2-{[1-(3-Chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

LC/MS [method 2]: R$_t$=3.22 min; MS [ESIpos]: m/z=561 (M+H)⁺

Preparative chiral HPLC: R$_t$=11.35 min, d.e.=100% [column: Daicel Chiralcel OX-H 5 μm, 250×20 mm; eluent: isohexane/ethanol 80:20; flow rate: 15 ml/min; temperature: 25° C.; UV detection: 220 nm].

¹H NMR (400 MHz, DMSO-d₆): δ [ppm] 1.46 (d, 3H), 3.85 (dd, 1H), 4.00 (dd, 1H), 4.25-4.35 (m, 1H), 4.81 (quin, 1H), 5.06 (s, 2H), 5.74 (d, 1H), 6.90 (d, 1H), 7.59-7.70 (m, 4H), 7.73-7.78 (m, 2H), 7.93 (dd, 1H).

Example 46

5-(4-Chlorophenyl)-2-({1-(3,5-dichlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

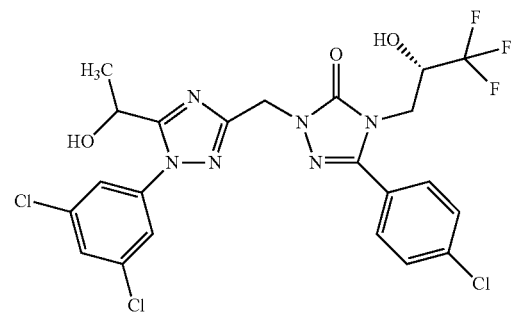 [SMILES: CC(O)c1nc(Cn2nc(-c3ccc(Cl)cc3)n(C[C@H](O)C(F)(F)F)c2=O)nn1-c1cc(Cl)cc(Cl)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (3,5-dichlorophenyl)boronic acid (352.73 mg, 1.85 mmol) and copper(II) acetate (335.7 mg, 1.85 mmol). The reaction mixture was heated to 60° C. for 2 h and then stirred at room temperature for 6 days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (105.5 mg, 0.18 mmol) was obtained as a mixture of diastereomers (yield 19.8%).

LC/MS [method 3]: $R_t$=1.39 min; MS [ESIpos]: m/z=577 (M+H)$^+$ $^1$H NMR (400 MHz, DMSO-d$_6$): δ [ppm] 1.48 (d, 3H), 3.85 (dd, 1H), 4.01 (dd, 1H), 4.23-4.36 (m, 1H), 4.82-4.90 (m, 1H), 5.02-5.12 (m, 2H), 6.84-6.94 (m, 1H), 7.59-7.65 (m, 2H), 7.72-7.82 (m, 5H).

The two diastereomers were separated by preparative chiral HPLC [sample preparation: 103.5 mg dissolved in 14 ml ethanol/isohexane (1:1); injection volume: 2 ml; column: Daicel Chiralcel® OX-H 5 μm, 250×20 mm; eluent: isohexane/ethanol 80:20; flow rate: 20 ml/min; temperature: 30° C.; UV detection: 220 nm]. After separation, 29.2 mg of diastereomer 1 (Example 47), which eluted first, and 28.9 mg of diastereomer 2 (Example 48), which eluted later, were isolated.

Example 47

5-(4-Chlorophenyl)-2-{[1-(3,5-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=1.49 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 1.48 (d, 3H), 3.85 (dd, 1H), 4.01 (dd, 1H), 4.24-4.35 (m, 1H), 4.86 (quin, 1H), 5.01-5.12 (m, 2H), 5.82 (d, 1H), 6.88 (d, 1H), 7.58-7.66 (m, 2H), 7.72-7.82 (m, 5H).

Example 48

5-(4-Chlorophenyl)-2-{[1-(3,5-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=2.02 min, d.e.=99.8% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 1.48 (d, 3H), 3.85 (dd, 1H), 4.01 (dd, 1H), 4.23-4.36 (m, 1H), 4.86 (quin, 1H), 5.07 (s, 2H), 5.82 (d, 1H), 6.89 (d, 1H), 7.59-7.65 (m, 2H), 7.72-7.81 (m, 5H).

Example 49

5-(4-Chlorophenyl)-2-({1-(2,5-dichlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

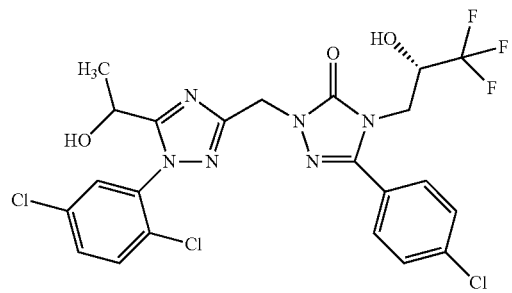 [SMILES: CC(O)c1nc(Cn2nc(-c3ccc(Cl)cc3)n(C[C@H](O)C(F)(F)F)c2=O)nn1-c1cc(Cl)ccc1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (2,5-dichlorophenyl)boronic acid (352.73 mg, 1.85 mmol) and copper(II) acetate (335.75 mg, 1.85 mmol). The reaction mixture was heated to 60° C. for 2 h and then stirred at room temperature for three days, after which extra boronic acid (100 mg, 0.52 mmol) was added due to incomplete conversion. The reaction mixture was further stirred at room temperature for 6 days. Over this time, another portion of boronic acid (100 mg, 0.52 mmol) was added. After this, the resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (52.8 mg, 0.09 mmol, 97% purity) was obtained as a mixture of diastereomers (yield 9.6%).

LC/MS [method 3]: $R_t$=1.33 min; MS [ESIpos]: m/z=577 (M+H)$^+$ $^1$H NMR (400 MHz, DMSO-d$_6$): δ [ppm] 1.40 (d, 3H), 3.85 (dd, 1H), 4.00 (dd, 1H), 4.23-4.35 (m, 1H), 4.63-4.72 (m, 1H), 5.01-5.12 (m, 2H), 6.89 (br. s, 1H), 7.60-7.65 (m, 2H), 7.67-7.78 (m, 4H), 7.81 (br. d, 1H).

The two diastereomers were separated by preparative chiral HPLC (SFC) [sample preparation: 50 mg dissolved in 10 ml methanol; injection volume: 0.5 ml; column: Daicel Chiralcel® OX-H 5 μm, 250×20 mm; eluent: carbon dioxide/methanol 82:18; flow rate: 80 ml/min; temperature: 40° C.; UV detection: 210 nm]. After separation, 20.3 mg of diastereomer 1 (Example 50), which eluted first, and 24.1 mg of diastereomer 2 (Example 51), which eluted later, were isolated.

Example 50

5-(4-Chlorophenyl)-2-{[1-(2,5-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 3]: $R_t$=1.30 min; MS [ESIpos]: m/z=577 (M+H)$^+$

Analytical chiral HPLC (SFC): $R_t$=2.87 min, d.e.=100% [column: Daicel Chiralcel OX-3, 250×4 mm; eluent: carbon dioxide/methanol (5%→60%); flow rate: 3 ml/min; UV detection: 220 nm].

$^1$H NMR (400 MHz, DMSO-d$_6$): δ [ppm] 1.40 (d, 3H), 3.85 (dd, 1H), 4.00 (dd, 1H), 4.23-4.36 (m, 1H), 4.67 (quin, 1H), 5.01-5.12 (m, 2H), 5.53 (d, 1H), 6.89 (d, 1H), 7.60-7.65 (m, 2H), 7.67-7.78 (m, 4H), 7.81 (br. d, 1H).

Example 51

5-(4-Chlorophenyl)-2-{[1-(2,5-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 3]: R$_t$=1.30 min; MS [ESIpos]: m/z=577 (M+H)$^+$

Analytical chiral HPLC (SFC): R$_t$=3.11 min, d.e.=100% [column: Daicel Chiralcel OX-3, 250×4 mm; eluent: carbon dioxide/methanol (5%→60%); flow rate: 3 ml/min; UV detection: 220 nm].

$^1$H NMR (400 MHz, DMSO-d$_6$): δ [ppm] 1.40 (d, 3H), 3.85 (dd, 1H), 4.00 (dd, 1H), 4.23-4.35 (m, 1H), 4.67 (quin, 1H), 5.01-5.12 (m, 2H), 5.53 (d, 1H), 6.89 (d, 1H), 7.59-7.65 (m, 2H), 7.66-7.78 (m, 4H), 7.81 (br. d, 1H).

Example 52

2-({1-(3-Chloro-2-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (diastereomeric mixture)

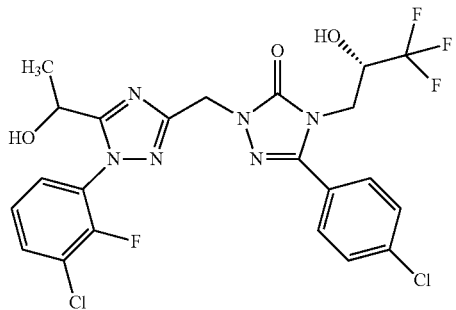 [SMILES: CC(O)c1nc(Cn2nc(-c3ccc(Cl)cc3)n(C[C@H](O)C(F)(F)F)c2=O)nn1-c1cccc(Cl)c1F]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (3-chloro-2-fluorophenyl)boronic acid (322.31 mg, 1.85 mmol) and copper(II) acetate (335.75 mg, 1.85 mmol). The reaction mixture was heated to 60° C. for 2 h and then stirred at room temperature for 12 days. Over this time, extra boronic acid (322.31 mg in total, 1.85 mmol) was added portionwise in a daily fashion. After this, the resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (15.9 mg, 0.03 mmol, 97% purity) was obtained as a mixture of diastereomers (yield 3%).

LC/MS [method 2]: R$_t$=3.12 min; MS [ESIpos]: m/z=561 (M+H)$^+$ $^1$H NMR (500 MHz, DMSO-d$_6$): δ [ppm] 1.42 (d, 3H), 3.85 (dd, 1H), 4.00 (dd, 1H), 4.23-4.35 (m, 1H), 4.75 (q, 1H), 5.02-5.12 (m, 2H), 5.57 (br. s, 1H), 6.89 (br. d, 1H), 7.40 (td, 1H), 7.60-7.65 (m, 3H), 7.72-7.77 (m, 2H), 7.81 (ddd, 1H).

The two diastereomers were separated by preparative chiral HPLC [sample preparation: 14 mg dissolved in 1 ml ethanol/isohexane (1:1); injection volume: 1 ml; column: Daicel Chiralcel® OX-H 5 μm, 250×20 mm; eluent: isohexane/ethanol 80:20; flow rate: 15 ml/min; temperature: 25° C.; UV detection: 220 nm]. After separation, 6 mg of diastereomer 1 (Example 53), which eluted first, and 6 mg of diastereomer 2 (Example 54), which eluted later, were isolated.

Example 53

2-{[1-(3-Chloro-2-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

LC/MS [method 2]: R$_t$=3.14 min; MS [ESIpos]: m/z=561 (M+H)$^+$

Analytical chiral HPLC: R$_t$=5.49 min, d.e.=100% [column: Daicel Chiralcel OX-H 5 μm, 250×4.6 mm; eluent: isohexane/ethanol 70:30+0.2% TFA and 1% water; flow rate: 1 ml/min; temperature: 40° C.; UV detection: 220 nm].

$^1$H NMR (500 MHz, DMSO-d$_6$): δ [ppm] 1.42 (d, 3H), 3.85 (dd, 1H), 4.00 (dd, 1H), 4.24-4.34 (m, 1H), 4.75 (quin, 1H), 5.03-5.11 (m, 2H), 5.57 (d, 1H), 6.89 (d, 1H), 7.40 (td, 1H), 7.60-7.65 (m, 3H), 7.73-7.77 (m, 2H), 7.81 (ddd, 1H).

Example 54

2-{[1-(3-Chloro-2-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

LC/MS [method 2]: R$_t$=3.13 min; MS [ESIpos]: m/z=561 (M+H)$^+$

Analytical chiral HPLC: R$_t$=6.16 min, d.e.=100% [column: Daicel Chiralcel OX-H 5 μm, 250×4.6 mm; eluent: isohexane/ethanol 70:30+0.2% TFA and 1% water; flow rate: 1 ml/min; temperature: 40° C.; UV detection: 220 nm].

$^1$H NMR (500 MHz, DMSO-d$_6$): δ [ppm] 1.42 (d, 3H), 3.85 (dd, 1H), 4.00 (dd, 1H), 4.25-4.34 (m, 1H), 4.75 (quin, 1H), 5.07 (s, 2H), 5.57 (d, 1H), 6.89 (d, 1H), 7.40 (td, 1H), 7.60-7.65 (m, 3H), 7.73-7.77 (m, 2H), 7.81 (ddd, 1H).

Example 55

5-(4-Chlorophenyl)-2-({1-[3-(difluoromethoxy)phenyl]-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

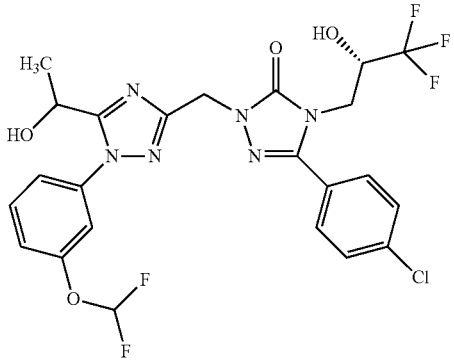 [SMILES: CC(O)c1nc(Cn2nc(-c3ccc(Cl)cc3)n(C[C@H](O)C(F)(F)F)c2=O)nn1-c1cccc(OC(F)F)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added [3-(difluoromethoxy)phenyl]boronic acid (347.40 mg, 1.85 mmol) and copper(II) acetate (335.75 mg, 1.85 mmol). The reaction mixture was heated to 60° C. for 2 h and then stirred at room temperature for 6 days, after which extra boronic acid (100 mg, 0.53 mmol) was added due to incomplete conversion. The reaction mixture was stirred at room temperature for two additional days. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (60.3 mg, 0.10 mmol) was obtained as a mixture of diastereomers (yield 11.4%).

LC/MS [method 3]: $R_t$=1.28 min; MS [ESIpos]: m/z=575 $(M+H)^+$ $^1$H NMR (400 MHz, DMSO-$d_6$): δ [ppm] 1.47 (d, 3H), 3.85 (dd, 1H), 4.01 (dd, 1H), 4.25-4.35 (m, 1H), 4.78-4.85 (m, 1H), 5.03-5.12 (m, 2H), 6.89 (br. s, 1H), 7.33 (t, 1H), 7.31-7.35 (m, 1H), 7.48-7.56 (m, 2H), 7.59-7.65 (m, 3H), 7.72-7.78 (m, 2H).

The two diastereomers were separated by preparative chiral HPLC [sample preparation: 58 mg dissolved in 2 ml ethanol; injection volume: 0.7 ml; column: Daicel Chiralcel® OX-H 5 μm, 250×20 mm; eluent: isohexane/ethanol 80:20; flow rate: 15 ml/min; temperature: 35° C.; UV detection: 220 nm]. After separation, 20.7 mg of diastereomer 1 (Example 56), which eluted first, and 17.7 mg of diastereomer 2 (Example 57), which eluted later, were isolated.

Example 56

5-(4-Chlorophenyl)-2-({1-[3-(difluoromethoxy)phenyl]-5-(1-hydroxyethyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomer 1)

Analytical chiral HPLC: $R_t$=5.57 min, d.e.=98.7% [column: Daicel Chiralcel OX-H 5, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.47 (d, 3H), 3.85 (dd, 1H), 4.01 (dd, 1H), 4.30 (br. s, 1H), 4.81 (q, 1H), 5.02-5.13 (m, 2H), 6.88 (br. s, 1H), 7.33 (t, 1H), 7.30-7.35 (m, 1H), 7.48-7.56 (m, 2H), 7.59-7.65 (m, 3H), 7.72-7.78 (m, 2H).

Example 57

5-(4-Chlorophenyl)-2-({1-[3-(difluoromethoxy)phenyl]-5-(1-hydroxyethyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomer 2)

Analytical chiral HPLC: $R_t$=6.70 min, d.e.=100% [column: Daicel Chiralcel OX-H 5, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.47 (d, 3H), 3.85 (dd, 1H), 4.01 (dd, 1H), 4.23-4.35 (m, 1H), 4.82 (quin, 1H), 5.07 (s, 2H), 5.75 (d, 1H), 6.90 (d, 1H), 7.33 (t, 1H), 7.30-7.35 (m, 1H), 7.48-7.56 (m, 2H), 7.59-7.65 (m, 3H), 7.72-7.78 (m, 2H).

Example 58

2-({1-(2-Chloro-5-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (diastereomeric mixture)

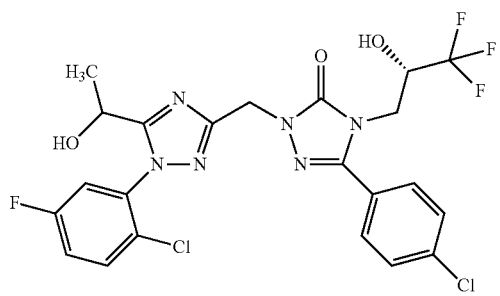 [SMILES: CC(O)c1nc(Cn2nc(-c3ccc(Cl)cc3)n(C[C@H](O)C(F)(F)F)c2=O)nn1-c1cc(F)ccc1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (2-chloro-5-fluorophenyl)boronic acid (322.31 mg, 1.85 mmol) and copper(II) acetate (335.75 mg, 1.85 mmol). The reaction mixture was heated to 60° C. for 2 h and then stirred at room temperature for 10 days. Over this time, extra boronic acid (322.31 mg in total, 1.85 mmol) was added portionwise in a daily fashion. The resulting reaction mixture was concentrated in vacuo, then diluted with ethyl acetate and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [method 4], and the desired compound (61 mg, 0.11 mmol, 98% purity) was obtained as a mixture of diastereomers (yield 11.5%).

LC/MS [method 2]: $R_t$=3.02 min; MS [ESIpos]: m/z=561 $(M+H)^+$ $^1$H NMR (400 MHz, DMSO-$d_6$): δ [ppm] 1.40 (d, 3H), 3.85 (dd, 1H), 4.00 (dd, 1H), 4.24-4.36 (m, 1H), 4.63-4.72 (m, 1H), 5.01-5.13 (m, 2H), 5.52 (br. s, 1H), 6.90 (dd, 1H), 7.52 (td, 1H), 7.60-7.69 (m, 3H), 7.73-7.79 (m, 3H).

The two diastereomers were separated by preparative chiral HPLC [sample preparation: 58 mg dissolved in 3 ml ethanol/isohexane (2:1); injection volume: 1 ml; column: Daicel Chiralcel® OX-H 5 μm, 250×20 mm; eluent: isohexane/ethanol 80:20; flow rate: 15 ml/min; temperature: 25° C.; UV detection: 220 nm]. After separation, 25 mg of diastereomer 1 (Example 59), which eluted first, and 25 mg of diastereomer 2 (Example 60), which eluted later, were isolated.

Example 59

2-{[1-(2-Chloro-5-fluorophenyl)-5-(1-hydroxy-ethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

LC/MS [method 2]: $R_t$=3.02 min; MS [ESIpos]: m/z=561 (M+H)$^+$

Analytical chiral HPLC: $R_t$=5.43 min, d.e.=100% [column: Daicel Chiralcel OX-H 5 µm, 250×4.6 mm; eluent: isohexane/ethanol 70:30+0.2% TFA and 1% water; flow rate: 1 ml/min; temperature: 40° C.; UV detection: 220 nm].

$^1$H NMR (400 MHz, DMSO-d$_6$): δ [ppm] 1.40 (d, 3H), 3.85 (dd, 1H), 4.00 (dd, 1H), 4.23-4.35 (m, 1H), 4.67 (quin, 1H), 5.01-5.12 (m, 2H), 5.53 (d, 1H), 6.89 (d, 1H), 7.52 (td, 1H), 7.60-7.68 (m, 3H), 7.72-7.79 (m, 3H).

Example 60

2-{[1-(2-Chloro-5-fluorophenyl)-5-(1-hydroxy-ethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

LC/MS [method 2]: $R_t$=3.02 min; MS [ESIpos]: m/z=561 (M+H)$^+$

Analytical chiral HPLC: $R_t$=6.11 min, d.e.=100% [column: Daicel Chiralcel OX-H 5 µm, 250×4.6 mm; eluent: isohexane/ethanol 70:30+0.2% TFA and 1% water; flow rate: 1 ml/min; temperature: 40° C.; UV detection: 220 nm].

$^1$H NMR (400 MHz, DMSO-d$_6$): δ [ppm] 1.40 (d, 3H), 3.85 (dd, 1H), 4.00 (dd, 1H), 4.30 (br. s, 1H), 4.67 (quin, 1H), 5.07 (s, 2H), 5.53 (d, 1H), 6.90 (d, 1H), 7.52 (td, 1H), 7.60-7.68 (m, 3H), 7.73-7.79 (m, 3H).

Example 61

5-(4-Chlorophenyl)-2-({1-(2,3-dichlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

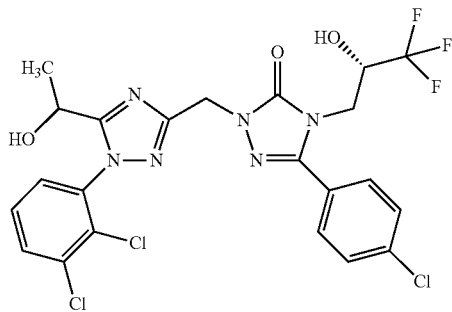 [SMILES: CC(O)c1nc(Cn2nc(-c3ccc(Cl)cc3)n(C[C@H](O)C(F)(F)F)c2=O)nn1-c1cccc(Cl)c1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (500 mg, 0.92 mmol, 80% purity) in pyridine (12 ml) were added (2,3-dichlorophenyl)boronic acid (176.36 mg, 0.92 mmol) and copper(II) acetate (335.75 mg, 1.85 mmol). The reaction mixture was heated to 60° C. for 1 h and then stirred at room temperature for 24 h, after which extra boronic acid (80 mg, 0.42 mmol) was added due to incomplete conversion. The reaction mixture was further stirred at room temperature for 5 days. Over this time, two additional portions of boronic acid (160 mg in total, 0.84 mmol) were added. After this, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (148 mg, 0.25 mmol, 97.3% purity) was obtained as a mixture of diastereomers (yield 27%).

LC/MS [method 2]: $R_t$=3.19 min; MS [ESIpos]: m/z=577 (M+H)$^+$ $^1$H NMR (400 MHz, DMSO-d$_6$): δ [ppm] 1.39 (d, 3H), 3.85 (dd, 1H), 4.00 (dd, 1H), 4.24-4.35 (m, 1H), 4.60-4.71 (m, 1H), 5.02-5.13 (m, 2H), 5.52 (br. s, 1H), 6.89 (dd, 1H), 7.55 (t, 1H), 7.59-7.66 (m, 3H), 7.73-7.78 (m, 2H), 7.87 (dd, 1H).

The two diastereomers were separated by preparative chiral HPLC (SFC) [sample preparation: 141 mg dissolved in 18 ml methanol; injection volume: 0.3 ml; column: Daicel Chiralcel® OX-H 5 µm, 250×20 mm; eluent: carbon dioxide/methanol 70:30; flow rate: 80 ml/min; temperature: 40° C.; UV detection: 210 nm]. After separation, 58.5 mg of diastereomer 1 (Example 62), which eluted first, and 53 mg of diastereomer 2 (Example 63), which eluted later, were isolated.

Example 62

5-(4-Chlorophenyl)-2-{[1-(2,3-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 2]: $R_t$=3.21 min; MS [ESIpos]: m/z=577 (M+H)$^+$; 95% purity

Analytical chiral HPLC (SFC): $R_t$=3.09 min, d.e.=100% [column: Daicel Chiralcel OX-3 250×4 mm; eluent: carbon dioxide/methanol (5%→60%); flow rate: 3 ml/min; UV detection: 220 nm].

$^1$H NMR (400 MHz, DMSO-d$_6$): δ [ppm] 1.39 (d, 3H), 3.85 (dd, 1H), 4.00 (dd, 1H), 4.24-4.36 (m, 1H), 4.65 (br. s, 1H), 5.01-5.13 (m, 2H), 5.52 (d, 1H), 6.89 (d, 1H), 7.55 (t, 1H), 7.59-7.66 (m, 3H), 7.72-7.78 (m, 2H), 7.87 (dd, 1H).

Example 63

5-(4-Chlorophenyl)-2-{[1-(2,3-dichlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

LC/MS [method 2]: $R_t$=3.20 min; MS [ESIpos]: m/z=577 (M+H)$^+$; 95% purity

Analytical chiral HPLC (SFC): $R_t$=3.38 min, d.e.=100% [column: Daicel Chiralcel OX-3 250×4 mm; eluent: carbon dioxide/methanol (5%→60%); flow rate: 3 ml/min; UV detection: 220 nm].

$^1$H NMR (400 MHz, DMSO-d$_6$): δ [ppm] 1.39 (d, 3H), 3.85 (dd, 1H), 4.00 (dd, 1H), 4.24-4.35 (m, 1H), 4.65 (br. s, 1H), 5.07 (s, 2H), 5.52 (d, 1H), 6.90 (d, 1H), 7.55 (t, 1H), 7.59-7.66 (m, 3H), 7.72-7.79 (m, 2H), 7.87 (dd, 1H).

Example 64

5-(4-Chlorophenyl)-2-({1-(2,3-difluorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

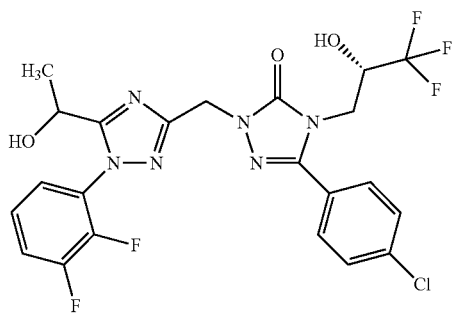 [SMILES: CC(O)c1nc(Cn2nc(-c3ccc(Cl)cc3)n(C[C@H](O)C(F)(F)F)c2=O)nn1-c1cccc(F)c1F]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (430 mg, 0.99 mmol) in pyridine (12.5 ml) were added (2,3-difluorophenyl)boronic acid (156.89 mg, 0.99 mmol) and copper(II) acetate (360.94 mg, 1.99 mmol). The reaction mixture was heated to 60° C. for 1 h and then stirred at room temperature for 24 h, after which extra boronic acid (80 mg, 0.51 mmol) was added due to incomplete conversion. The reaction mixture was further stirred at room temperature for five days. Over this time, five additional portions of boronic acid (400 mg in total, 2.54 mmol) were added. After this, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (44 mg, 0.08 mmol) was obtained as a mixture of diastereomers (yield 8.1%).

LC/MS [method 2]: $R_t$=2.97 min; MS [ESIpos]: m/z=545 $(M+H)^+$ $^1$H NMR (400 MHz, DMSO-$d_6$): δ [ppm] 1.42 (d, 3H), 3.85 (dd, 1H), 4.00 (dd, 1H), 4.30 (br. s, 1H), 4.76 (q, 1H), 5.02-5.13 (m, 2H), 6.89 (br. s, 1H), 7.35-7.43 (m, 1H), 7.45-7.51 (m, 1H), 7.59-7.71 (m, 3H), 7.72-7.79 (m, 2H).

The two diastereomers were separated by preparative chiral HPLC [sample preparation: 40 mg dissolved in 1 ml ethanol; injection volume: 0.5 ml; column: Daicel Chiralcel® OX-H 5 μm, 250×20 mm; eluent: isohexane/ethanol 80:20; flow rate: 15 ml/min; temperature: 35° C.; UV detection: 220 nm]. After separation, 18 mg of diastereomer 1 (Example 65), which eluted first, and 16 mg of diastereomer 2 (Example 66), which eluted later, were isolated.

Example 65

5-(4-Chlorophenyl)-2-{[1-(2,3-difluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=5.74 min, d.e.=100% [column: Daicel Chiralcel OX-H 5 μm, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.42 (d, 3H), 3.85 (dd, 1H), 4.00 (dd, 1H), 4.24-4.35 (m, 1H), 4.76 (quin, 1H), 5.02-5.13 (m, 2H), 5.58 (d, 1H), 6.89 (d, 1H), 7.35-7.44 (m, 1H), 7.45-7.52 (m, 1H), 7.59-7.72 (m, 3H), 7.72-7.78 (m, 2H).

Example 66

5-(4-Chlorophenyl)-2-{[1-(2,3-difluorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=6.59 min, d.e.=99.2% [column: Daicel Chiralcel OX-H 5 μm, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.42 (d, 3H), 3.85 (dd, 1H), 4.00 (dd, 1H), 4.23-4.36 (m, 1H), 4.76 (quin, 1H), 5.07 (s, 2H), 5.58 (d, 1H), 6.90 (d, 1H), 7.35-7.43 (m, 1H), 7.44-7.51 (m, 1H), 7.59-7.72 (m, 3H), 7.72-7.78 (m, 2H).

Example 67

2-{[1-(2-Chloro-3-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 1)

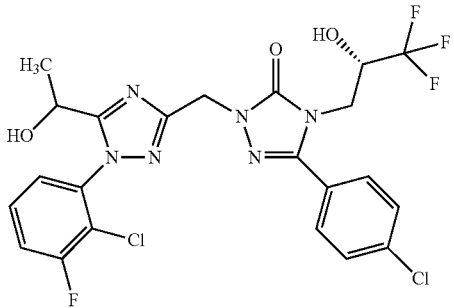 [SMILES: CC(O)c1nc(Cn2nc(-c3ccc(Cl)cc3)n(C[C@H](O)C(F)(F)F)c2=O)nn1-c1cccc(F)c1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (500 mg, 0.92 mmol, 80% purity) in pyridine (12 ml) were added (2-chloro-3-fluorophenyl)boronic acid (161.15 mg, 0.92 mmol) and copper(II) acetate (335.75 mg, 1.85 mmol). The reaction mixture was heated to 60° C. for 1 h and then stirred at room temperature for 24 h, after which extra boronic acid (75 mg, 0.43 mmol) was added due to incomplete conversion. The reaction mixture was further stirred at room temperature for six days. Over this time, five additional portions of boronic acid (375 mg in total, 2.15 mmol) were added. After this, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and 91 mg of the desired compound as a diastereomeric mixture still containing some impurities were isolated.

A further purification by preparative chiral HPLC yielded the two pure, separated diastereomers [sample preparation: 90 mg dissolved in 3 ml ethanol; injection volume: 0.3 ml; column: Daicel Chiralcel® OX-H 5 μm, 250×20 mm; eluent: isohexane/ethanol 80:20; flow rate: 15 ml/min; temperature: 35° C.; UV detection: 220 nm]. After separation, 20 mg of diastereomer 1 (Example 67), which eluted first, and 21 mg of diastereomer 2 (Example 68), which eluted later, were isolated.

LC/MS [method 2]: $R_t$=3.01 min; MS [ESIpos]: m/z=561 (M+H)$^+$

Analytical chiral HPLC: $R_t$=6.22 min, d.e.=100% [column: Daicel Chiralcel OX-H 5 μm, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.39 (d, 3H), 3.85 (dd, 1H), 4.00 (dd, 1H), 4.23-4.36 (m, 1H), 4.66 (quin, 1H), 5.01-5.14 (m, 2H), 5.53 (d, 1H), 6.89 (d, 1H), 7.48-7.70 (m, 5H), 7.72-7.78 (m, 2H).

Example 68

2-{[1-(2-Chloro-3-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (diastereomer 2)

LC/MS [method 2]: $R_t$=3.01 min; MS [ESIpos]: m/z=561 (M+H)$^+$

Analytical chiral HPLC: $R_t$=7.94 min, d.e.=100% [column: Daicel Chiralcel OX-H 5 μm, 250×4.6 mm; eluent: isohexane/ethanol 70:30+0.2% TFA and 1% water; flow rate: 1 ml/min; temperature: 35° C.; UV detection: 220 nm].

$^1$H NMR (400 MHz, DMSO-$d_6$): δ [ppm] 1.40 (d, 3H), 3.85 (dd, 1H), 4.00 (dd, 1H), 4.24-4.36 (m, 1H), 4.66 (quin, 1H), 5.07 (s, 2H), 5.53 (d, 1H), 6.90 (d, 1H), 7.49-7.70 (m, 5H), 7.72-7.78 (m, 2H).

Example 69

5-(4-Chlorophenyl)-2-({5-[(1RS)-1-hydroxyethyl]-1-(2-methylphenyl)-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

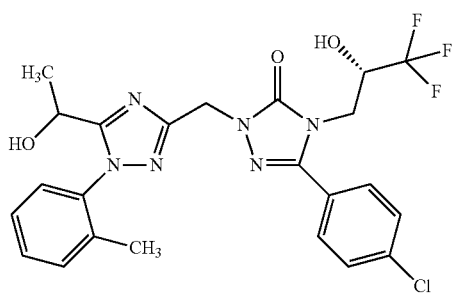 [SMILES: Cc1ccccc1-n1nc(Cn2nc(-c3ccc(Cl)cc3)n(C[C@H](O)C(F)(F)F)c2=O)nc1C(C)O]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (400 mg, 0.92 mmol) in pyridine (12 ml) were added (2-methylphenyl)boronic acid (251.32 mg, 1.85 mmol) and copper(II) acetate (335.75 mg, 1.85 mmol). The reaction mixture was stirred at room temperature for 5 days, after which extra boronic acid (62.8 mg, 0.46 mmol, 0.5 eq.) was added due to incomplete conversion. After stirring for two additional days, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (100 mg, 0.17 mmol) was obtained as a mixture of diastereomers (yield 17.2%, 90% purity).

LC/MS [method 3]: $R_t$=1.24 min; MS [ESIpos]: m/z=523 (M+H)$^+$

The two diastereomers were separated by preparative chiral HPLC [sample preparation: 98 mg dissolved in 2 ml ethanol/isohexane (1:1); injection volume: 1 ml; column: Daicel Chiralcel® OX-H 5 μm, 250×20 mm; eluent: isohexane/ethanol 75:25; flow rate: 15 ml/min; temperature: 30° C.; UV detection: 220 nm]. After separation, 37 mg of diastereomer 1 (Example 70), which eluted first, and 39 mg of diastereomer 2 (Example 71), which eluted later, were isolated.

Example 70

5-(4-Chlorophenyl)-2-{[5-(1-hydroxyethyl)-1-(2-methylphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 3]: $R_t$=1.24 min; MS [ESIpos]: m/z=523 (M+H)$^+$

Analytical chiral HPLC: $R_t$=7.65 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.36 (d, 3H), 1.98 (s, 3H), 3.85 (dd, 1H), 4.00 (dd, 1H), 4.23-4.35 (m, 1H), 4.54 (quin, 1H), 5.00-5.12 (m, 2H), 5.48 (d, 1H), 6.89 (d, 1H), 7.31-7.49 (m, 4H), 7.59-7.65 (m, 2H), 7.71-7.77 (m, 2H).

Example 71

5-(4-Chlorophenyl)-2-{[5-(1-hydroxyethyl)-1-(2-methylphenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=10.27 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.37 (d, 3H), 1.98 (s, 3H), 3.84 (dd, 1H), 4.00 (dd, 1H), 4.24-4.35 (m, 1H), 4.54 (quin, 1H), 5.06 (s, 2H), 5.48 (d, 1H), 6.90 (d, 1H), 7.31-7.49 (m, 4H), 7.58-7.66 (m, 2H), 7.71-7.78 (m, 2H).

Example 72

5-(4-Chlorophenyl)-2-({5-[(1RS)-1-hydroxyethyl]-1-[2-(trifluoromethyl)phenyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

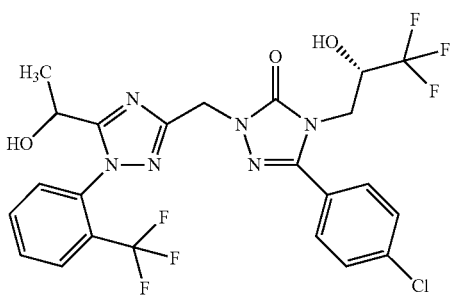 [SMILES: CC(O)c1nc(Cn2nc(-c3ccc(Cl)cc3)n(C[C@H](O)C(F)(F)F)c2=O)nn1-c1ccccc1C(F)(F)F]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (600 mg, 1.11 mmol, 80% purity) in pyridine (14.5 ml) were added [2-(trifluoromethyl)phenyl]boronic acid (421.30 mg, 2.22 mmol) and copper(II) acetate (402.9 mg, 2.22 mmol). The reaction mixture was heated to 60° C. for 2 h and then stirred at room temperature for 5 days, after which extra boronic acid (105 mg, 0.55 mmol, 0.5 eq.) was added due to incomplete conversion. After further stirring at room temperature overnight, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (80 mg) was obtained as a mixture of diastereomers (yield 12.4%).

LC/MS [method 2]: $R_t$=3.19 min; MS [ESIpos]: m/z=577 (M+H)$^+$

The two diastereomers were separated by preparative chiral HPLC [sample preparation: 78 mg dissolved in 2 ml ethanol/isohexane (1:1); injection volume: 1 ml; column: Daicel Chiralcel® OX-H 5 μm, 250×20 mm; eluent: isohexane/ethanol 75:25; flow rate: 15 ml/min; temperature: 30° C.; UV detection: 220 nm]. After separation, 34 mg of diastereomer 1 (Example 73), which eluted first, and 30 mg of diastereomer 2 (Example 74), which eluted later, were isolated.

Example 73

5-(4-Chlorophenyl)-2-({5-(1-hydroxyethyl)-1-[2-(trifluoromethyl)phenyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomer 1)

Analytical chiral HPLC: $R_t$=6.16 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.36 (d, 3H), 3.84 (dd, 1H), 4.00 (dd, 1H), 4.24-4.35 (m, 1H), 4.57 (quin, 1H), 4.99-5.12 (m, 2H), 5.50 (d, 1H), 6.89 (d, 1H), 7.59-7.65 (m, 2H), 7.66-7.71 (m, 1H), 7.72-7.76 (m, 2H), 7.77-7.90 (m, 2H), 7.93-7.99 (m, 1H).

Example 74

5-(4-Chlorophenyl)-2-({5-(1-hydroxyethyl)-1-[2-(trifluoromethyl)phenyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomer 2)

Analytical chiral HPLC: $R_t$=8.67 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.36 (d, 3H), 3.84 (dd, 1H), 3.99 (dd, 1H), 4.24-4.35 (m, 1H), 4.54-4.62 (m, 1H), 5.05 (s, 2H), 5.50 (d, 1H), 6.90 (d, 1H), 7.60-7.65 (m, 2H), 7.67-7.71 (m, 1H), 7.72-7.90 (m, 4H), 7.93-7.98 (m, 1H).

Example 75

5-(4-Chlorophenyl)-2-({1-(3-fluorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

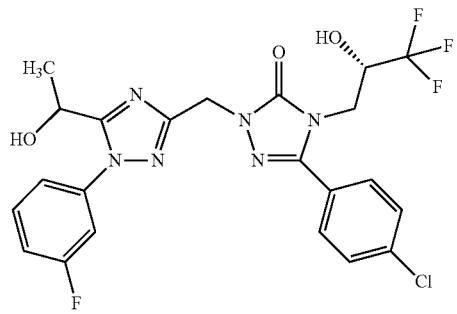 [SMILES: CC(O)c1nc(Cn2nc(-c3ccc(Cl)cc3)n(C[C@H](O)C(F)(F)F)c2=O)nn1-c1cccc(F)c1]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (430 mg, 0.795 mmol, 80% purity) in pyridine (10 ml) were added (3-fluorophenyl)boronic acid (222.432 mg, 1.59 mmol) and copper(II) acetate (288.75 mg, 1.59 mmol). The reaction mixture was heated to 60° C. for 2 h and then stirred at room temperature for 5 days, after which extra boronic acid (55.6 mg, 0.40 mmol) was added due to incomplete conversion. The reaction mixture was again heated to 60° C. for 2 h, followed by stirring at room temperature overnight. The resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (100 mg, 0.19 mmol) was obtained as a mixture of diastereomers (yield 23.9%).

LC/MS [method 2]: $R_t$=2.99 min; MS [ESIpos]: m/z=527 (M+H)$^+$

¹H NMR (400 MHz, DMSO-d₆): δ [ppm] 1.47 (d, 3H), 3.85 (dd, 1H), 4.01 (dd, 1H), 4.30 (br. s, 1H), 4.83 (q, 1H), 5.02-5.13 (m, 2H), 6.89 (br. s, 1H), 7.38 (td, 1H), 7.48-7.66 (m, 5H), 7.72-7.78 (m, 2H).

The two diastereomers were separated by preparative chiral HPLC [sample preparation: 97 mg dissolved in 4 ml ethanol/isohexane (1:1); injection volume: 1 ml; column: Daicel Chiralcel® OX-H 5 μm, 250×20 mm; eluent: isohexane/ethanol 80:20; flow rate: 15 ml/min; temperature: 30° C.; UV detection: 220 nm]. After separation, 36 mg of (1S)-diastereomer (Example 76), which eluted first, and 40 mg of (1R)-diastereomer (Example 77), which eluted later, were isolated.

Example 76

5-(4-Chlorophenyl)-2-({1-(3-fluorophenyl)-5-[(1S)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one

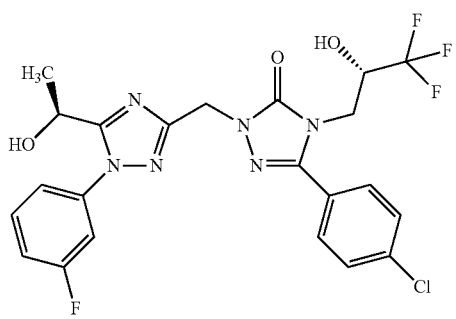 [SMILES: C[C@H](O)c1nc(Cn2nc(-c3ccc(Cl)cc3)n(C[C@H](O)C(F)(F)F)c2=O)nn1-c1cccc(F)c1]

LC/MS [method 3]: R_t=1.24 min; MS [ESIpos]: m/z=527 (M+H)⁺

Analytical chiral HPLC: R_t=9.71 min, d.e.=100% [column: LUX Cellulose-4, 5 μm, 250×4.6 mm; eluent: isohexane/ethanol 80:20; flow rate: 1 ml/min; temperature: 40° C.; UV detection: 220 nm].

¹H NMR (400 MHz, DMSO-d₆): δ [ppm] 1.47 (d, 3H), 3.85 (dd, 1H), 4.00 (dd, 1H), 4.23-4.37 (m, 1H), 4.82 (quin, 1H), 5.01-5.13 (m, 2H), 5.76 (d, 1H), 6.89 (d, 1H), 7.38 (td, 1H), 7.48-7.66 (m, 5H), 7.72-7.79 (m, 2H).

The absolute stereochemistry of the compound was determined by additionally performing the same reaction with enantiopure diastereomer 5-(4-chlorophenyl)-2-({5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 5A) as the starting material and comparison of the two respective products by analytical chiral HPLC.

Example 77

5-(4-Chlorophenyl)-2-({1-(3-fluorophenyl)-5-[(1R)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one

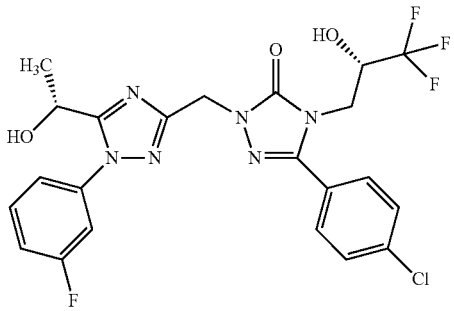

LC/MS [method 2]: R_t=2.93 min; MS [ESIpos]: m/z=527 (M+H)⁺

Analytical chiral HPLC: R_t=13.60 min, d.e.=100% [column: LUX Cellulose-4, 5 μm, 250×4.6 mm; eluent: isohexane/ethanol 80:20; flow rate: 1 ml/min; temperature: 40° C.; UV detection: 220 nm].

¹H NMR (400 MHz, DMSO-d₆): δ [ppm] 1.47 (d, 3H), 3.85 (dd, 1H), 4.01 (dd, 1H), 4.24-4.36 (m, 1H), 4.83 (quin, 1H), 5.07 (s, 2H), 5.76 (d, 1H), 6.90 (d, 1H), 7.38 (td, 1H), 7.48-7.65 (m, 5H), 7.72-7.78 (m, 2H).

The absolute stereochemistry of the compound was determined by additionally performing the same reaction with enantiopure diastereomer 5-(4-chlorophenyl)-2-({5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 6A) as the starting material and comparison of the two respective products by analytical chiral HPLC.

Example 78

5-(4-Chlorophenyl)-2-({1-(3-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

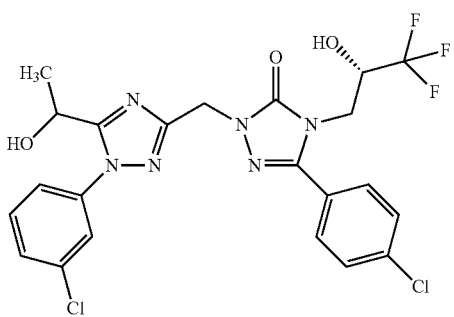

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (430 mg, 0.795 mmol, 80% purity) in pyridine (10 ml)

were added (3-chlorophenyl)boronic acid (248.59 mg, 1.59 mmol) and copper(II) acetate (288.75 mg, 1.59 mmol). The reaction mixture was heated to 60° C. for 2 h and then stirred at room temperature for 5 days, after which extra boronic acid (62.1 mg, 0.40 mmol) was added due to incomplete conversion. The reaction mixture was again heated to 60° C. for 2 h, followed by stirring at room temperature overnight. The resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (130 mg, 0.24 mmol) was obtained as a mixture of diastereomers (yield 30.1%).

LC/MS [method 2]: $R_t$=3.19 min; MS [ESIpos]: m/z=543 $(M+H)^+$ $^1$H NMR (400 MHz, DMSO-$d_6$): δ [ppm] 1.47 (d, 3H), 3.85 (dd, 1H), 4.01 (dd, 1H), 4.30 (br. s, 1H), 4.81 (q, 1H), 5.02-5.13 (m, 2H), 6.89 (br. s, 1H), 7.56-7.67 (m, 5H), 7.72-7.79 (m, 3H).

The two diastereomers were separated by preparative chiral HPLC [sample preparation: 128 mg dissolved in 4 ml ethanol/isohexane (1:1); injection volume: 1 ml; column: Daicel Chiralcel® OX-H 5 µm, 250×20 mm; eluent: isohexane/ethanol 80:20; flow rate: 15 ml/min; temperature: 30° C.; UV detection: 220 nm]. After separation, 52 mg of (1S)-diastereomer (Example 79), which eluted first, and 49 mg of (1R)-diastereomer (Example 80), which eluted later, were isolated.

Example 79

5-(4-Chlorophenyl)-2-({1-(3-chlorophenyl)-5-[(1S)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one

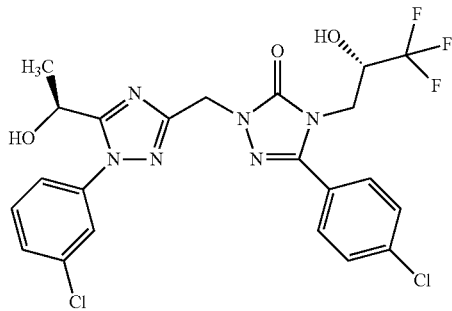 [SMILES: C[C@H](O)c1nc(Cn2nc(-c3ccc(Cl)cc3)n(C[C@H](O)C(F)(F)F)c2=O)nn1-c1cccc(Cl)c1]

LC/MS [method 2]: $R_t$=3.14 min; MS [ESIpos]: m/z=543 $(M+H)^+$

Analytical chiral HPLC: $R_t$=9.96 min, d.e.=100% [column: LUX Cellulose-4, 5 µm, 250×4.6 mm; eluent: isohexane/ethanol 80:20; flow rate: 1 ml/min; temperature: 35° C.; UV detection: 220 nm].

$^1$H NMR (400 MHz, DMSO-$d_6$): δ [ppm] 1.47 (d, 3H), 3.85 (dd, 1H), 4.01 (dd, 1H), 4.23-4.36 (m, 1H), 4.81 (quin, 1H), 5.01-5.13 (m, 2H), 5.76 (d, 1H), 6.89 (d, 1H), 7.56-7.66 (m, 5H), 7.71-7.79 (m, 3H).

$^{13}$C NMR (125 MHz, DMSO-$d_6$): δ [ppm] 21.3, 42.1, 42.2, 59.6, 65.5, 123.0, 124.5, 124.6, 125.3, 128.5, 128.9 (2×), 130.0 (2×), 130.7, 133.0, 135.2, 138.2, 144.8, 153.1, 157.8, 158.6.

The absolute stereochemistry of the compound was determined by additionally performing the same reaction with enantiopure diastereomer 5-(4-chlorophenyl)-2-({5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 5A) as the starting material and comparison of the two respective products by analytical chiral HPLC.

Example 80

5-(4-Chlorophenyl)-2-({1-(3-chlorophenyl)-5-[(1R)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one

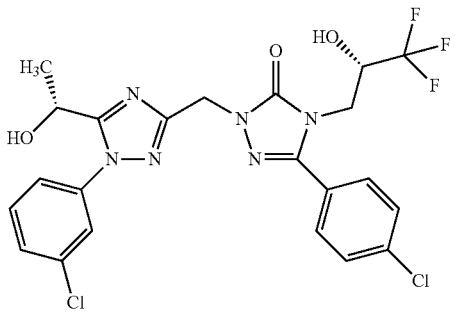

LC/MS [method 2]: $R_t$=3.15 min; MS [ESIpos]: m/z=543 $(M+H)^+$

Analytical chiral HPLC: $R_t$=14.41 min, d.e.=100% [column: LUX Cellulose-4, 5 µm, 250×4.6 mm; eluent: isohexane/ethanol 80:20; flow rate: 1 ml/min; temperature: 35° C.; UV detection: 220 nm].

$^1$H NMR (400 MHz, DMSO-$d_6$): δ [ppm] 1.47 (d, 3H), 3.85 (dd, 1H), 4.01 (dd, 1H), 4.24-4.37 (m, 1H), 4.81 (quin, 1H), 5.07 (s, 2H), 5.76 (d, 1H), 6.90 (d, 1H), 7.56-7.66 (m, 5H), 7.71-7.79 (m, 3H).

The absolute stereochemistry of the compound was determined by additionally performing the same reaction with enantiopure diastereomer 5-(4-chlorophenyl)-2-({5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 6A) as the starting material and comparison of the two respective products by analytical chiral HPLC.

Example 81

5-(4-Chlorophenyl)-2-({1-(2-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

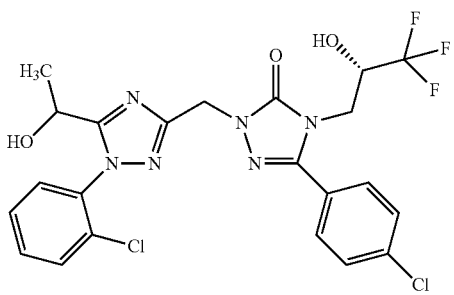 [SMILES: CC(O)c1nc(Cn2nc(-c3ccc(Cl)cc3)n(C[C@H](O)C(F)(F)F)c2=O)nn1-c1ccccc1Cl]

To a solution of 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (2.10 g, 3.88 mmol, 80% purity) in pyridine (50 ml) were added (2-chlorophenyl)boronic acid (1.214 g, 7.76 mmol) and copper(II) acetate (1.410 g, 7.76 mmol). The reaction mixture was heated to 60° C. for 1 h and then stirred at room temperature for 5 days, after which extra boronic acid (303 mg, 1.94 mmol) was added due to incomplete conversion. After stirring at room temperature for two additional days, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 4], and the desired compound (580 mg, 1.01 mmol, 95% purity) was obtained as a mixture of diastereomers (yield 26.1%).

LC/MS [method 3]: $R_t$=1.24 min; MS [ESIpos]: m/z=543 $(M+H)^+$ $^1$H NMR (400 MHz, DMSO-$d_6$): δ [ppm] 1.38 (d, 3H), 3.85 (dd, 1H), 4.00 (dd, 1H), 4.30 (br. s, 1H), 4.55-4.64 (m, 1H), 5.01-5.13 (m, 2H), 6.85-6.94 (m, 1H), 7.50-7.65 (m, 5H), 7.67-7.78 (m, 3H).

The two diastereomers were separated by preparative chiral HPLC (SFC) [sample preparation: 575 mg dissolved in 35 ml methanol; injection volume: 0.4 ml; column: Daicel Chiralcel® OX-H 5 μm, 250×20 mm; eluent: carbon dioxide/methanol 70:30; flow rate: 80 ml/min; temperature: 40° C.; UV detection: 210 nm]. After separation, 206 mg of (1S)-diastereomer (Example 82), which eluted first, and 189 mg of (1R)-diastereomer (Example 83), which eluted later, were isolated.

Example 82

5-(4-Chlorophenyl)-2-({1-(2-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one

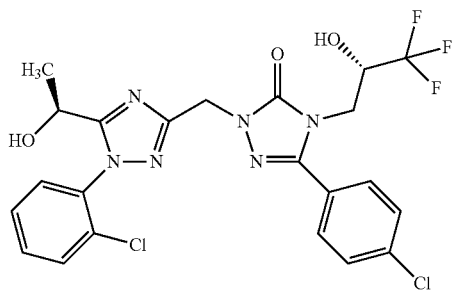 [SMILES: C[C@H](O)c1nc(Cn2nc(-c3ccc(Cl)cc3)n(C[C@H](O)C(F)(F)F)c2=O)nn1-c1ccccc1Cl]

LC/MS [method 3]: $R_t$=1.24 min; MS [ESIpos]: m/z=543 $(M+H)^+$

Analytical chiral HPLC: $R_t$=8.34 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.38 (d, 3H), 3.85 (dd, 1H), 4.00 (dd, 1H), 4.30 (br. s, 1H), 4.59 (q, 1H), 5.01-5.13 (m, 2H), 5.50 (br. s, 1H), 6.90 (d, 1H), 7.50-7.65 (m, 5H), 7.67-7.78 (m, 3H).

The absolute stereochemistry of the compound was determined by additionally performing the same reaction with enantiopure diastereomer 5-(4-chlorophenyl)-2-({5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 5A) as the starting material and comparison of the two respective products by analytical chiral HPLC.

Example 83

5-(4-Chlorophenyl)-2-({1-(2-chlorophenyl)-5-[(1R)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one

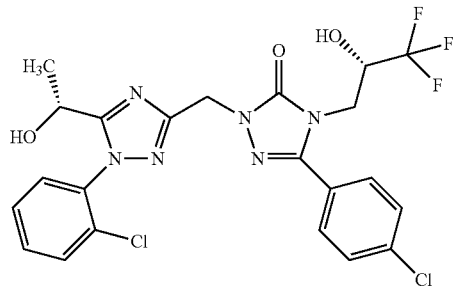 [SMILES: C[C@@H](O)c1nc(Cn2nc(-c3ccc(Cl)cc3)n(C[C@H](O)C(F)(F)F)c2=O)nn1-c1ccccc1Cl]

Analytical chiral HPLC: $R_t$=11.88 min, d.e.=98.1% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-$d_6$): δ [ppm] 1.38 (d, 3H), 3.85 (dd, 1H), 4.00 (dd, 1H), 4.24-4.36 (m, 1H), 4.54-4.65 (m, 1H), 5.07 (s, 2H), 5.51 (br. s, 1H), 6.90 (d, 1H), 7.50-7.65 (m, 5H), 7.68-7.79 (m, 3H).

The absolute stereochemistry of the compound was determined by additionally performing the same reaction with enantiopure diastereomer 5-(4-chlorophenyl)-2-({5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 6A) as the starting material and comparison of the two respective products by analytical chiral HPLC.

B. EVALUATION OF BIOLOGICAL ACTIVITY

Abbreviations and Acronyms:
Acc. No. accession number
AVP arginine vasopressin
$B_{max}$ maximal ligand binding capacity
BSA bovine serum albumin
cAMP cyclic adenosine monophosphate
Cat. No. catalogue number
cDNA complementary deoxyribonucleic acid
CHO chinese hamster ovary
CRE cAMP response element
Ct cycle threshold
DMEM/F12 Dulbecco's modified Eagle's medium/Ham's F12 medium (1:1)
DNA deoxyribonucleic acid
DTT dithiothreitol
$EC_{50}$ half-maximal effective concentration
EDTA ethylenediamine-tetraacetic acid
FAM carboxyfluorescein succinimidyl ester
f.c. final concentration
FCS fetal calf serum HEPES 4-(2-hydroxyethyl)piperazine-1-ethanesulfonic acid
$IC_{50}$ half-maximal inhibitory concentration
$K_d$ dissociation constant
$K_i$ dissociation constant of an inhibitor
mRNA messenger ribonucleic acid
PBS phosphate buffered saline
p.o. per os, peroral
RNA ribonucleic acid
RTPCR real-time polymerase chain reaction
SPA scintillation proximity assay
TAMRA carboxytetramethylrhodamine
TRIS 2-amino-2-hydroxymethylpropane-1,3-diol Demonstration of the activity of the compounds of the present invention may be accomplished through in vitro, ex vivo, and in vivo assays that are well known in the art. For example, to demonstrate the activity of the compounds of the present invention, the following assays may be used.

B-1. Cellular in Vitro Assay for Determining Vasopressin Receptor Activity

The identification of agonists and antagonists of the V1a and V2 vasopressin receptors from humans, rats and dogs as well as the quantification of the activity of the compounds of the invention is carried out using recombinant cell lines. These cell lines originally derive from a hamster's ovary epithelial cell (Chinese Hamster Ovary, CHO K1, ATCC: American Type Culture Collection, Manassas, Va. 20108, USA). The test cell lines constitutively express the human, rat or dog V1a or V2 receptors. In case of the $G_{\alpha y}$-coupled V1a receptors, cells are also stably transfected with a modified form of the calcium-sensitive photoproteins aequorin (human and rat V1a) or obelin (dog V1a), which, after reconstitution with the cofactor coelenterazine, emit light when there are increases in free calcium concentrations [Rizzuto R, Simpson A W, Brini M, Pozzan T, *Nature* 358, 325-327 (1992); Illarionov B A, Bondar V S, Illarionova V A, Vysotski E S, *Gene* 153 (2), 273-274 (1995)]. The resulting vasopressin receptor cells react to stimulation of the recombinantly expressed V1a receptors by intracellular release of calcium ions, which can be quantified by the resulting photoprotein luminescence. The $G_s$-coupled V2 receptors are stably transfected into cell lines expressing the gene for firefly luciferase under control of a CRE-responsible promoter. Activation of V2 receptors induces the activation of the CRE-responsive promoter via cAMP increase, thereby inducing the expression of firefly luciferase. The light emitted by photoproteins of V1a cell lines as well as the light emitted by firefly luciferase of V2 cell lines corresponds to the activation or inhibition of the respective vasopressin receptor. The bioluminescence of the cell lines is detected using a suitable luminometer [Milligan G, Marshall F, Rees S, *Trends in Pharmacological Sciences* 17, 235-237 (1996)].

Test Procedure:

Vasopressin V1a Receptor Cell Lines:

On the day before the assay, the cells are plated out in culture medium (DMEM/F12, 2% FCS, 2 mM glutamine, 10 mM HEPES, 5 µg/ml coelenterazine) in 384-well microtiter plates and kept in a cell incubator (96% humidity, 5% v/v $CO_2$, 37° C.). On the day of the assay, test compounds in various concentrations are placed for 10 minutes in the wells of the microtiter plate before the agonist [Arg$^8$]-vasopressin at $EC_{50}$ concentration is added. The resulting light signal is measured immediately in the luminometer.

Vasopressin V2 Receptor Cell Lines:

On the day before the assay, the cells are plated out in culture medium (DMEM/F12, 2% FCS, 2 mM glutamine, 10 mM HEPES) in 384-well microtiter plates and kept in a cell incubator (96% humidity, 5% v/v CO2, 37° C.). On the day of the assay, test compounds in various concentrations and the agonist [Arg$^8$]-vasopressin at $EC_{50}$ concentration are added together to the wells, and plates are incubated for 3 hours in a cell incubator. Upon addition of the cell lysis reagent Triton and the substrate luciferin, luminescence of firefly luciferase is measured in a luminometer.

Table 1A below lists individual $IC_{50}$ values for the compounds of the invention (including diastereomeric mixtures as well as separated, enantiopure diastereomers) that were obtained from cell lines transfected with the human V1a or V2 receptor:

TABLE 1A

| Example No. | $IC_{50}$ hV1a [µM] | $IC_{50}$ hV2 [µM] |
|---|---|---|
| 1 | 0.0060 | 0.0025 |
| 2 | 0.0050 | 0.0087 |
| 3 | 0.0010 | 0.0056 |
| 4 | 0.0004 | 0.0053 |
| 5 | 0.0004 | 0.0018 |
| 6 | 0.0106 | 0.0017 |
| 7 | 0.0076 | 0.0026 |
| 8 | 0.0012 | 0.0107 |
| 9 | 0.0004 | 0.0023 |
| 10 | 0.0014 | 0.0014 |
| 11 | 0.0004 | 0.0003 |
| 12 | 0.0013 | 0.0011 |
| 13 | 0.0062 | 0.0014 |
| 14 | 0.0013 | 0.0004 |
| 15 | 0.0384 | 0.0041 |
| 16 | 0.0031 | 0.0060 |
| 17 | 0.0027 | 0.0034 |
| 18 | 0.0141 | 0.0086 |
| 19 | 0.0124 | 0.0014 |
| 20 | 0.0038 | 0.0008 |
| 21 | 0.0578 | 0.0022 |
| 22 | 0.0244 | 0.0023 |
| 23 | 0.0122 | 0.0009 |
| 24 | 0.1200 | 0.0020 |
| 25 | 0.0072 | 0.0036 |
| 26 | 0.0031 | 0.0030 |
| 27 | 0.0437 | 0.0077 |
| 28 | 0.0013 | 0.0002 |
| 29 | 0.0029 | 0.0002 |
| 30 | 0.0716 | 0.0004 |
| 31 | 0.0016 | 0.0009 |
| 32 | 0.0009 | 0.0010 |
| 33 | 0.0016 | 0.0023 |
| 34 | 0.0004 | 0.0012 |
| 35 | 0.0005 | 0.0016 |
| 36 | 0.0008 | 0.0028 |
| 37 | 0.0005 | 0.0007 |
| 38 | 0.0006 | 0.0009 |
| 39 | 0.0015 | 0.0035 |
| 40 | 0.0015 | 0.0072 |
| 41 | 0.0018 | 0.0079 |
| 42 | 0.0051 | 0.0127 |
| 43 | 0.0062 | 0.0012 |
| 44 | 0.0061 | 0.0012 |
| 45 | 0.0921 | 0.0033 |
| 46 | 0.0063 | 0.0021 |
| 47 | 0.0189 | 0.0037 |
| 48 | 0.0032 | 0.0024 |
| 49 | 0.0018 | 0.0126 |
| 50 | 0.0013 | 0.0100 |
| 51 | 0.0030 | 0.0223 |
| 52 | 0.0039 | 0.0004 |
| 53 | 0.0079 | 0.0018 |
| 54 | 0.0397 | 0.0016 |
| 55 | 0.0148 | 0.0042 |
| 56 | 0.0024 | 0.0014 |
| 57 | 0.0382 | 0.0082 |
| 58 | 0.0002 | 0.0015 |
| 59 | 0.0005 | 0.0024 |
| 60 | 0.0005 | 0.0052 |
| 61 | 0.0032 | 0.0002 |

TABLE 1A-continued

| Example No. | IC$_{50}$ hV1a [µM] | IC$_{50}$ hV2 [µM] |
|---|---|---|
| 62 | 0.0078 | 0.0009 |
| 63 | 0.0516 | 0.0019 |
| 64 | 0.0081 | 0.0051 |
| 65 | 0.0025 | 0.0033 |
| 66 | 0.0040 | 0.0019 |
| 67 | 0.0021 | 0.0027 |
| 68 | 0.0033 | 0.0013 |
| 70 | 0.0005 | 0.0011 |
| 71 | 0.0006 | 0.0021 |
| 73 | 0.0011 | 0.0070 |
| 74 | 0.0022 | 0.0247 |
| 75 | 0.0029 | 0.0066 |
| 76 | 0.0025 | 0.0051 |
| 77 | 0.0125 | 0.0135 |
| 78 | 0.0104 | 0.0031 |
| 79 | 0.0036 | 0.0017 |
| 80 | 0.0463 | 0.0051 |
| 82 | 0.0007 | 0.0023 |
| 83 | 0.0010 | 0.0067 |

The IC$_{50}$ data listed in Table 1A demonstrate that the compounds of the present invention are acting as highly potent dual antagonists of vasopressin V1a and V2 receptors.

For comparative purposes, selected phenyl-triazole and imidazole derivatives that were regarded to be representative of closest prior art (cf. Int. Pat. Appl. WO 2011/104322-A1 and example compounds described therein) were also tested in the cellular V1a and V2 assays described above. IC$_{50}$ values for these compounds obtained from cell lines transfected with the human V1a or V2 receptor are listed in Table 1B below:

TABLE 1B

| Example No. WO 2011/104322 | IC$_{50}$ hV1a [µM] | IC$_{50}$ hV2 [µM] |
|---|---|---|
| 54 | 0.0166 | 0.0564 |
| 56 | 0.0013 | 0.0067 |
| 60 | 0.0542 | 0.0326 |
| 68 | 0.0060 | 0.0083 |
| 101 | 0.0422 | 0.0238 |
| 110 | 0.0152 | 0.0043 |

B-2. Radioactive Binding Assay

IC$_{50}$ and K, values were determined in a radioactive binding competition SPA assay using membrane fractions of recombinant CHO cell lines expressing the respective human, rat or dog vasopressin V1a and V2 receptors. These cells derive from a hamster's ovary epithelial cell (Chinese Hamster Ovary, CHO K1, ATCC: American Type Culture Collection, Manassas, Va. 20108, USA). In addition, the cells are stably transfected with the human, rat or dog V1a or V2 receptor. The membrane preparations were subjected to the radioactive receptor binding competition assay described below.

The respective vasopressin receptor-transfected CHO cells were grown in an appropriate quantity in T-175 flasks with DMEM/F12, 10% FCS, 15 mM HEPES, 1 mg/ml G418 and kept in a cell incubator (96% humidity, 5% v/v CO2, 37° C.). After reaching the appropriate confluency, cells were harvested for membrane preparation. Cells were scraped into PBS and pelleted by gentle centrifugation at 200×g for 5 min at room temperature. Pellets were re-suspended in PBS and again centrifugated. After repeating this step once more, the resulting pellets were shock-frozen at −80° C. for 30 min. Frozen pellets were re-suspended in ice-cold preparation buffer (50 mM TRIS, 2 mM EDTA, 2 mM DTT, cOmplete Protease Inhibitor Cocktail) and homogenized at 2000 rpm for 35 seconds (Polytron PT3000, Kinematica). The homogenate was cooled down for 2 min on ice, and the homogenization was repeated twice. The resulting homogenate was centrifugated at 500×g for 10 min at 4° C. Membranes were pelleted at 4500×g for 20 min at 4° C., re-suspended in storing buffer (7.5 mM TRIS, 12.5 mM MgCl$_2$, 0.3 mM EDTA, 250 mM sucrose, cOmplete Protease Inhibitor Cocktail) and homogenized at 2000 rpm for 2 seconds (Polytron PT3000, Kinematica). The protein concentration was determined by using the BCA Protein Assay (Thermo Scientific Pierce), and the membrane preparations were stored at −80° C. On the day of use, aliquots were thawed and briefly vortexed.

For the determination of the receptor binding affinity of test compounds, an SPA assay was set-up as follows. For each membrane preparation, K$_d$ and B$_{max}$ values were determined. From these data, the number of SPA beads (WGA PVT beads, PerkinElmer, 200 µg/well), the concentration of radioactive ligand ($^3$H-AVP, PerkinElmer, 2.431 TBq/mmol, f.c. 1-2×K$_d$) and the amount of the respective membrane preparation (10 µg protein/well) were matched to the assay volume (100 µl) in binding buffer (50 mM TRIS, 0.2% BSA) in a 96-well plate. The test compounds were diluted in binding buffer (f.c. 10$^{-4}$ M to 10$^{-12}$ M) and subjected to the assay. Plates were gently shaken for 1-3 hours at room temperature and further incubated for 1-2 hours. Signals generated by bound $^3$H-AVP were measured using a β-counter (1450 Microbeta Trilux). From these results, IC$_{50}$ and K, values for the tested compounds were calculated using GraphPad Prism.

B-3. Cellular in Vitro Assay for Detecting the Action of Vasopressin V1a Receptor Antagonists on the Regulation of Pro-Fibrotic Genes The cell line H9C2 (American Type Culture Collection No. CRL-1446), described as a cardiomyocyte type isolated from rat cardiac tissue, endogenously expresses the vasopressin V1A receptor AVPR1A in high copy number, whereas AVPR2 expression cannot be detected. For cell assays for the inhibition of AVPR1A receptor-dependent regulation of gene expression by receptor antagonists, the procedure is as follows:

H9C2 cells are seeded in 6-well microtiter plates for cell culture at a cell density of 50 000 cells/well in 2.0 ml of Opti-MEM medium (Invitrogen Corp., Carlsbad, Calif., USA, Cat. No. 11058-021) and held in a cell incubator (96% humidity, 8% v/v CO2, 37° C.). After 24 hours, sets of three wells (triplicate) are charged with vehicle solution (negative control) and vasopressin solution ([Arg$^8$]-vasopressin acetate, Sigma, Cat. No. V9879), or test compound (dissolved in vehicle: water with 20% v/v ethanol) and vasopressin solution. In the cell culture, the final vasopressin concentration is 1 nM. The test compound solution is added to the cell culture in small volumes, so that a final concentration of 0.03% of ethanol in the cell assay is not exceeded. After an incubation time of 5 hours, the culture supernatant is drawn off under suction, the adherent cells are lysed in 350 µl of RLT buffer (Qiagen, Cat. No. 79216), and the RNA is isolated from the lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and RTPCR (pPCR MasterMix RT-QP2X-03-075, Eurogentec, Seraing, Belgium). All procedures take place in accordance with the working protocols of the test reagents' manufacturers. The primer sets for the RTPCR are selected on the basis of the mRNA gene sequences (NCBI GenBank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 384-well microtiter plate format in accordance with the instrument operating instructions. The relative gene expression is represented by the delta-delta Ct value [Applied Biosystems, User Bulletin No. 2 ABI Prism 7700 SDS, Dec. 11, 1997 (updated 10/2001)] with reference to the level of expression of the ribosomal protein L-32 gene (GenBank Acc. No. NM_013226) and the threshold Ct value of Ct=35.

B-4. In Vivo Assay for Detecting Cardiovascular Effects: Blood Pressure Measurement in Anaesthetized Rats (Vasopressin 'Challenge' model)

In male Sprague-Dawley rats (250-350 g body weight) under ketamine/xylazine/pentobarbital injection anaesthesia, polyethylene tubes (PE-50, Intramedic®), which are prefilled with heparin-containing (500 IU/ml) isotonic sodium chloride solution, are introduced into the jugular vein and the femoral vein and then tied in. Via one venous access, with the aid of a syringe, Arg-vasopressin is injected; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment, the experimental animal is administered 3-4 successive bolus injections at intervals of 10-15 min with a defined amount of Arg-vasopressin (30 ng/kg) in isotonic sodium chloride solution. When the blood pressure has reached initial levels again, the test substance is administered as a bolus, with subsequent continuous infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of Arg-vasopressin. Control animals only receive solvent instead of the test substance.

Following intravenous administration, the compounds of the invention, in comparison to the solvent controls, bring about an inhibition of the blood pressure increase caused by Arg-vasopressin.

B-5. In Vivo Assay for Detecting Cardiovascular Effects: Diuresis Investigations in Conscious Rats Kept in Metabolism Cages Wistar rats (220-450 g body weight) are kept with free access to feed (Altromin) and drinking water. During the experiment, the animals are kept with free access to drinking water for 4 to 8 or up to 24 hours individually in metabolism cages suitable for rats of this weight class (Tecniplast Deutschland GmbH, D-82383 HohenpeiBenberg). At the beginning of the experiment, the animals are administered the test substance in a volume of 1 to 3 ml/kg body weight of a suitable solvent by means of gavage into the stomach. Control animals only receive solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per time unit is determined separately for each animal, and the concentration of urinary electrolytes is measured by standard methods of flame photometry. Before the beginning of the experiment, the body weight of the individual animals is determined.

Following oral administration, in comparison with the solvent control applications, the compounds of the invention bring about an increased excretion of urine, which is based essentially on an increased excretion of water (aquaresis).

Table 2A below shows observed changes in urinary excretion relative to solvent control (=100%) for exemplary compounds of the invention at two different dosages:

TABLE 2A

| Example No. | Dosage p.o. [mg/kg] | Urinary volume [% vs. control = 100%] | Dosage p.o. [mg/kg] | Urinary volume [% vs. control = 100%] |
|---|---|---|---|---|
| 1 | 0.3 | 194 | 3.0 | 588 |
| 2 | 0.3 | 194 | 3.0 | 588 |
| 3 | 0.3 | 89 | 3.0 | 450 |
| 4 | 0.3 | 91 | 1.0 | 190 |
| 5 | 0.3 | 166 | 1.0 | 438 |
| 6 | 0.3 | 132 | 1.0 | 439 |
| 11 | 0.3 | 159 | 3.0 | 443 |
| 12 | 0.3 | 96 | 3.0 | 323 |
| 14 | — | — | 1.0 | 753 |
| 15 | 0.3 | 412 | 3.0 | 1085 |
| 17 | 0.3 | 404 | 1.0 | 819 |
| 29 | 0.3 | 404 | 1.0 | 983 |
| 70 | 0.3 | 139 | 3.0 | 595 |
| 76 | 0.3 | 350 | 3.0 | 1257 |
| 79 | 0.3 | 612 | 3.0 | 1312 |
| 82 | 0.3 | 220 | 3.0 | 828 |
| 83 | 0.3 | 279 | 3.0 | 1094 |

For comparative purposes, selected phenyl-triazole and imidazole derivatives that were regarded to be representative of closest prior art (cf. Int. Pat. Appl. WO 2011/104322-A1 and example compounds described therein) were also tested for diuretic effect in this assay. Observed changes in urinary excretion relative to solvent control (=100%) at two different dosages are shown in Table 2B below:

TABLE 2B

| Example No. WO 2011/104322 | Dosage p.o. [mg/kg] | Urinary volume [% vs. control = 100%] | Dosage p.o. [mg/kg] | Urinary volume [% vs. control = 100%] |
|---|---|---|---|---|
| 54 | 0.3 | 85 | 3.0 | 188 |
| 56 | 0.3 | 128 | 3.0 | 85 |
| 60 | 0.3 | 96 | 3.0 | 84 |
| 68 | 0.3 | 87 | 3.0 | 121 |
| 101 | 0.3 | 111 | 3.0 | 255 |
| 110 | 0.3 | 114 | 3.0 | 274 |

The results shown in Table 2A and 2B demonstrate that the compounds of the present invention are significantly more potent in vivo: Tested examples of the present invention gave rise to more than a threefold, in some cases to more than a tenfold increase in urinary volume versus the vehicle control group at a p.o. dose of 3 mg/kg, and most examples exhibited substantial aquaretic activity already at p.o. doses of 0.3 mg/kg or 1 mg/kg. This is in contrast to the phenyl-triazole and imidazole derivatives regarded to be representative of closest prior art which were not active at p.o. doses below 3 mg/kg and slightly active at 3 mg/kg.

B-6. In Vivo Assay for Detecting Cardiovascular Effects: Hemodynamic Investigations in Anaesthetized Dogs Male beagle dogs (Beagle, Marshall BioResources) with a weight of between 10 and 15 kg are anaesthetized with pentobarbital (30 mg/kg i.v., Narcoren®, Merial, Germany)

for the surgical interventions and hemodynamic and functional examinations. Pancuronium bromide (2 mg/animal i.v., Ratiopharm, Germany) serves additionally as a muscle relaxant. The dogs are intubated and ventilated with an oxygen/ambient air mixture (40/60%, about 3-4 L/min) Ventilation is carried out using a ventilator from GE Healthcare (Avance) and is monitored using an analyzer (Datex-Ohmeda, GE). Anaesthesia is maintained by continuous infusion of pentobarbital (50 µg/kg/min); fentanyl is used as an analgesic (10-40 µg/kg/h). An alternative to pentobarbital is to use isoflurane (1-2% by volume).

In preparatory interventions, the dogs are fitted with a cardiac pacemaker. At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with transillumination, into the right ventricle. Thereafter all of the accesses are removed, and the dog wakes spontaneously from the anaesthesia. After a further 7 days (i.e. 14 days before the first drug testing), the above-described pacemaker is activated, and the heart is stimulated at a frequency of 220 beats per minute.

The actual substance testing experiments are carried out 14 and 28 days after the beginning of pacemaker stimulation, using the following instrumentation:

- introduction of a bladder catheter for bladder relief and for measuring the flow of urine;
- attachment of ECG leads to the extremities for ECG measurement;
- introduction of a Fluidmedic PE 300 tube filled with sodium chloride solution into the femoral artery; this tube is connected to a pressure sensor (Braun Melsungen, Germany) for measuring systemic blood pressure;
- introduction of a Millar Tip catheter (type 350 PC, Millar Instruments, Houston, USA) through the left atrium or through a port secured in the carotid artery, for measuring cardiac hemodynamics;
- introduction of a Swan-Ganz catheter (CCOmbo 7.5F, Edwards, Irvine, USA) via the jugular vein into the pulmonary artery, for measuring cardiac output, oxygen saturation, pulmonary arterial pressures and central venous pressure;
- siting of a venous catheter in the cephalic vein, for infusing pentobarbital, for liquid replacement and for blood sampling (determination of plasma levels of the test substance or of other clinical blood values);
- siting of a venous catheter in the saphenous vein, for infusing fentanyl and for administration of the test substance;
- continuous infusion of vasopressin (Sigma, 4 mU/kg/min); test compounds are then administered and evaluated at different dosages under this vasopressin infusion.

The primary signals are amplified if necessary (ACQ 7700 amplifier, DataSciences Inc., Minneapolis, USA, or Edwards-Vigilance-Monitor, Edwards, Irvine, USA) and subsequently fed into the Ponemah system (DataSciences Inc., Minneapolis, USA) for evaluation. The signals are recorded continuously throughout the experimental period, and are further processed digitally by the software and averaged over 30 seconds.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. Examples Relating To Pharmaceutical Compositions

Pharmaceutical compositions according to the present invention can be illustrated as follows:

Sterile i.v. Solution:

A 5 mg/mL solution of the desired compound of the invention can be made using sterile, injectable water, and the pH is adjusted if necessary. The solution is diluted for administration to 1-2 mg/mL with sterile 5% dextrose and is administered as an i.v. infusion over about 60 minutes.

Lyophilized Powder for i.v Administration:

A sterile preparation can be prepared with (i) 100-1000 mg of the desired compound of the invention as a lyophilized powder, (ii) 32-327 mg/mL sodium citrate, and (iii) 300-3000 mg Dextran 40. The formulation is reconstituted with sterile, injectable saline or 5% dextrose to a concentration of 10 to 20 mg/mL, which is further diluted with saline or 5% dextrose to 0.2 to 0.4 mg/mL, and is administered either as i.v. bolus or by i.v. infusion over 15-60 minutes.

Intramuscular Suspension:

The following solution or suspension can be prepared for intramuscular injection:

50 mg/mL of the desired, water-insoluble compound of the invention; 5 mg/mL sodium carboxymethylcellulose; 4 mg/mL Tween 80; 9 mg/mL sodium chloride; 9 mg/mL benzyl alcohol.

Hard Shell Capsules:

A large number of unit capsules are prepared by filling standard two-piece hard gelatin capsules each with 100 mg of the desired, powdered compound of the invention, 150 mg of lactose, 50 mg of cellulose and 6 mg of magnesium stearate.

Soft Gelatin Capsules:

A mixture of the desired compound of the invention in a digestible oil, such as soybean oil, cottonseed oil or olive oil, is prepared and injected by means of a positive displacement pump into molten gelatin to form soft gelatin capsules containing 100 mg of the active ingredient. The capsules are washed and dried. The desired compound of the invention can be dissolved in a mixture of polyethylene glycol, glycerin and sorbitol to prepare a water-miscible medicine mix.

Tablets:

A large number of tablets are prepared by conventional procedures so that the dosage unit is 100 mg of the desired compound of the invention, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:
1. A compound of formula (I)

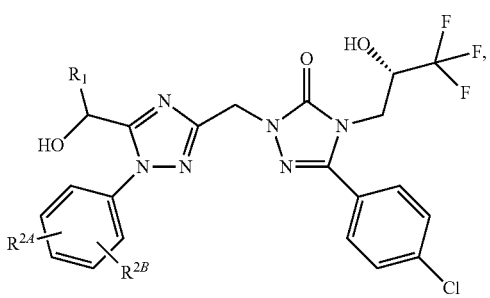

wherein
R¹ is hydrogen or methyl,
and
R²ᴬ and R²ᴮ are independently selected from the group consisting of hydrogen, fluoro, chloro, cyano, methyl, fluoromethyl, difluoromethyl, trifluoromethyl, ethyl, methoxy, difluoromethoxy and trifluoromethoxy,
or a pharmaceutically acceptable salt, hydrate and/or solvate thereof.

2. The compound of claim 1, wherein
R¹ is hydrogen or methyl,
and
R²ᴬ and R²ᴮ are independently selected from the group consisting of hydrogen, fluoro, chloro, methyl and methoxy, wherein at least one of R²ᴬ and R²ᴮ is other than hydrogen,
or a pharmaceutically acceptable salt, hydrate and/or solvate thereof.

3. The compound of claim 1, wherein the compound is selected from the group consisting of
5-(4-chlorophenyl)-2-{[1-(3-chlorophenyl)-5-(hydroxymethyl)-1H-1,2,4-triazol-3-yl]-methyl-}-4-[(2S)-3,3,3-trifluoro-2-hydroxypropyl]-2,4-dihydro-3H-1,2,4-triazol-3-one;
5-(4-chlorophenyl)-2-{[1-(3-fluorophenyl)-5-(hydroxymethyl)-1H-1,2,4-triazol-3-yl]-methyl-}-4-[(2S)-3,3,3-trifluoro-2-hydroxypropyl]-2,4-dihydro-3H-1,2,4-triazol-3-one;
5-(4-chlorophenyl)-2-{[5-(hydroxymethyl)-1-(2-methylphenyl)-1H-1,2,4-triazol-3-yl]-methyl-}-4-[(2S)-3,3,3-trifluoro-2-hydroxypropyl]-2,4-dihydro-3H-1,2,4-triazol-3-one;
2-({1-(2-chloro-4-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one;
2-{[1-(2-chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one(diastereomer 1);
2-{[1-(2-chloro-4-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one(diastereomer 2);
2-({1-(2-chloro-5-fluorophenyl)-5-[(1RS)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one;
2-{[1-(2-chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one(diastereomer 1);
2-{[1-(2-chloro-5-fluorophenyl)-5-(1-hydroxyethyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one(diastereomer 2);
5-(4-chlorophenyl)-2-({1-(3-fluorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-fluorophenyl)-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-fluorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-chlorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-chlorophenyl)-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(2-chlorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(2-chlorophenyl)-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
and
5-(4-chlorophenyl)-2-({1-(2-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
or a pharmaceutically acceptable salt, hydrate and/or solvate thereof.

4. The compound of claim 1, wherein the compound is selected from the group consisting of
5-(4-chlorophenyl)-2-({1-(3-fluorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-fluorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-chlorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;
5-(4-chlorophenyl)-2-({1-(2-chlorophenyl)-5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

and
5-(4-chlorophenyl)-2-({1-(2-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one;

or a pharmaceutically acceptable salt, hydrate and/or solvate thereof.

5. 5-(4-Chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one, a compound having the following formula

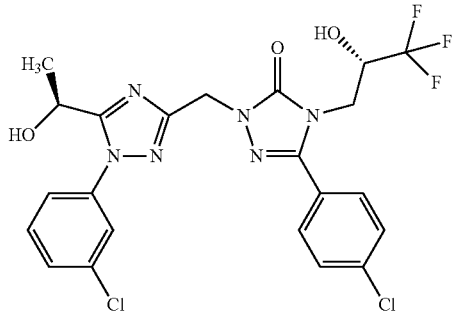 [SMILES: C[C@H](O)c1nc(Cn2nc(-c3ccc(Cl)cc3)n(C[C@H](O)C(F)(F)F)c2=O)nn1-c1cccc(Cl)c1]

or a pharmaceutically acceptable salt, hydrate and/or solvate thereof.

6. The compound of claim 5, wherein the compound is 5-(4-Chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one having the following formula

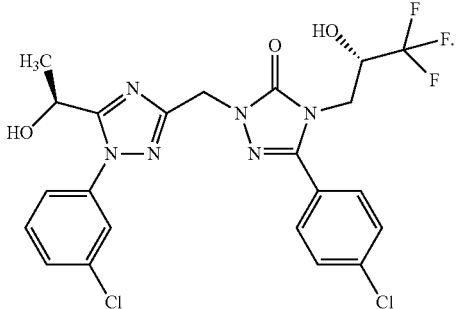 [SMILES: C[C@H](O)c1nc(Cn2nc(-c3ccc(Cl)cc3)n(C[C@H](O)C(F)(F)F)c2=O)nn1-c1cccc(Cl)c1]

7. A process for preparing a compound of claim 1, comprising:
reacting a compound of formula (II)

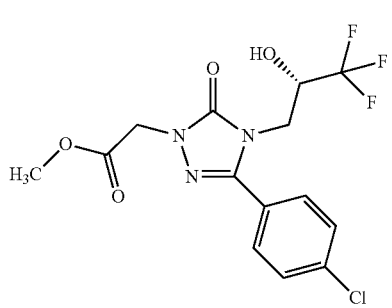

is with hydrazine to give the hydrazide of formula (III)

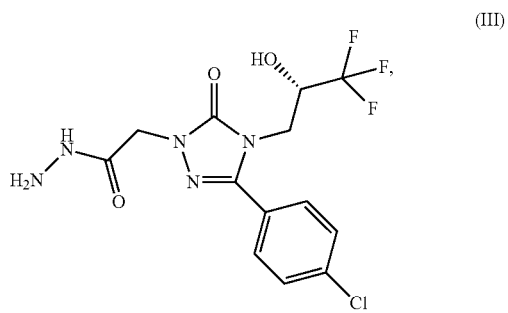 [SMILES: NNC(=O)Cn1nc(-c2ccc(Cl)cc2)n(C[C@H](O)C(F)(F)F)c1=O]

condensing the hydrazide of formula (III) with an amidine of formula (IV)

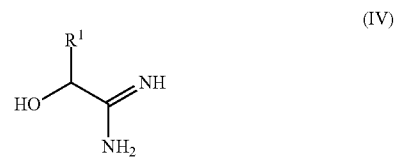

or a salt thereof,
wherein $R^1$ has the meaning indicated in claim 1,
in the presence of a base to give a 1,2,4-triazole derivative of formula (V)

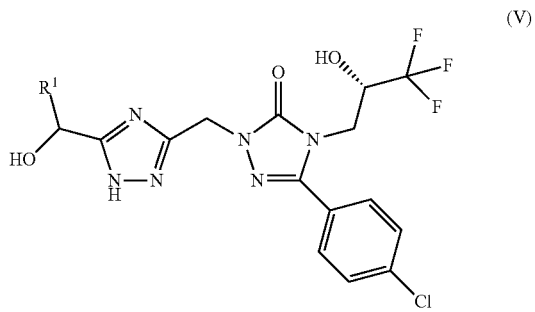

and/or a tautomer thereof,
wherein $R^1$ has the meaning indicated in claim 1,
and coupling the 1,2,4-triazole derivative of formula (V) and/or tautomer thereof with a phenylboronic acid of formula (VI)

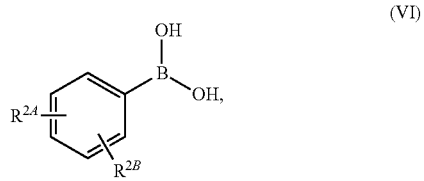

wherein $R^{2A}$ and $R^{2B}$ have the meanings indicated in claim 1,
in the presence of a copper catalyst and an amine base to yield a compound of formula (I)

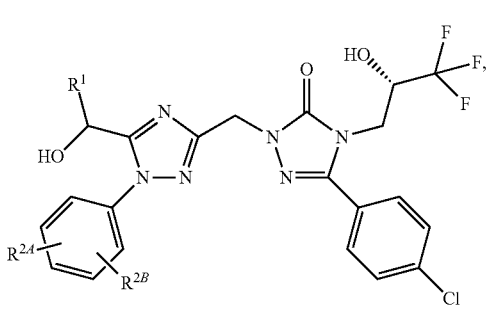

(I)

wherein $R^1$, $R^{2A}$ and $R^{2B}$ have the meanings indicated in claim 1, and when more than one diastereomer, hydrate, solvate, salt, or hydrate or solvate of the salt of the compound of formula (I) is produced they are optionally separated into their respective diastereomers, and/or converted into their respective hydrates, solvates, salts and/or hydrates or solvates of the salts by treatment with the corresponding solvents and/or acids or bases.

8. A pharmaceutical composition comprising a compound of claim 1 and at least one pharmaceutically acceptable excipient.

9. The pharmaceutical composition of claim 8 further comprising at least one therapeutic agent selected from the group consisting of a diuretic, an angiotensin AII antagonist, an ACE inhibitor, a beta-receptor blocker, a mineralocorticoid receptor antagonist, an organic nitrate, an NO donor, an activator of soluble guanylate cyclase, a stimulator of soluble guanylate cyclase, and a positive-inotropic agent.

10. A method of inhibiting the action of vasopressin in a human or other animal comprising administering to the human or the other mammal in need thereof a therapeutically effective amount of at least one compound of claim 1.

11. A method of inhibiting the action of vasopressin in a human or other animal comprising administering to the human or the other mammal in need thereof a therapeutically effective amount of the pharmaceutical composition of claim 8.

12. A method for the treatment of acute and chronic heart failure, comprising administering to a human or other mammal in need thereof a therapeutically effective amount of at least one compound of claim 1.

13. A method for the treatment of acute and chronic heart failure, comprising administering to a human or other mammal in need thereof a therapeutically effective amount of the pharmaceutical composition of claim 8.

14. A method for treatment of acute and chronic heart failure, comprising administering to a human or other mammal in need thereof a therapeutically effective amount of 5-(4-Chlorophenyl)-2-({1-(3-chlorophenyl)-5-[(1S)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one, a compound having the following formula

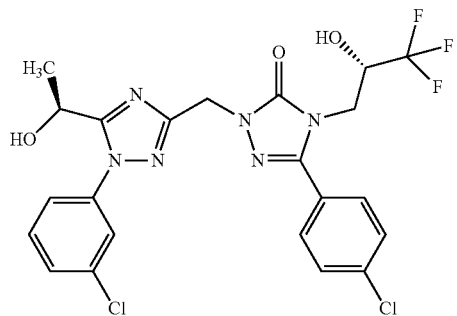 [SMILES: C[C@H](O)c1nc(Cn2nc(-c3ccc(Cl)cc3)n(C[C@H](O)C(F)(F)F)c2=O)nn1-c1cccc(Cl)c1]

or a pharmaceutically acceptable salt, hydrate and/or solvate thereof.

15. The method of claim 14, comprising administering the compound, having the following formula

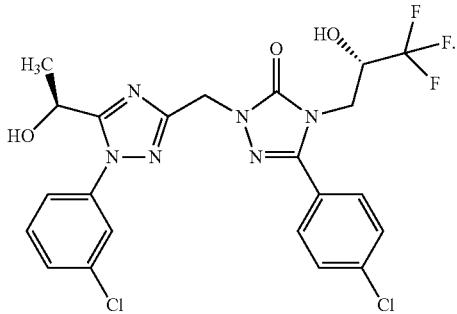 [SMILES: C[C@H](O)c1nc(Cn2nc(-c3ccc(Cl)cc3)n(C[C@H](O)C(F)(F)F)c2=O)nn1-c1cccc(Cl)c1]

* * * * *